(12) United States Patent
Hatfield et al.

(10) Patent No.: US 11,446,165 B2
(45) Date of Patent: Sep. 20, 2022

(54) TRACTION SYSTEM FOR AN AMBULATORY SUPPORT

(71) Applicant: NIKE, Inc., Beaverton, OR (US)

(72) Inventors: Tobie D. Hatfield, Lake Oswego, OR (US); Austin J. Orand, Portland, OR (US); George A. Xanthos, Beaverton, OR (US); Aron Kristbjorn Albertsson, Hafnarfjordur (IS); Bjarni Andresson, Seltjarnarnes (IS); Arinbjorn Viggo Clausen, Reykjavik (IS); Christophe Guy Lecomte, Reykjavik (IS); Sindri Pall Sigurdsson, Reykjavik (IS); Maria Gudrun Sveinbjornsdottir, Mosfellsbaer (IS)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 17/198,190

(22) Filed: Mar. 10, 2021

(65) Prior Publication Data

US 2021/0307935 A1    Oct. 7, 2021

Related U.S. Application Data

(60) Provisional application No. 63/004,698, filed on Apr. 3, 2020.

(51) Int. Cl.
*A61F 2/66*    (2006.01)
*A61H 3/02*    (2006.01)
*A61F 2/50*    (2006.01)

(52) U.S. Cl.
CPC ............. *A61F 2/66* (2013.01); *A61H 3/0288* (2013.01); *A61F 2002/503* (2013.01);
(Continued)

(58) Field of Classification Search
CPC ........ A61F 2/66; A61F 2/78; A61F 2002/503; A61F 2002/5038; A61F 2002/5072;
(Continued)

(56) References Cited

U.S. PATENT DOCUMENTS 2,322,497 A   6/1943 Weinaug
2,622,889 A   12/1952 De Place
(Continued)

FOREIGN PATENT DOCUMENTS

CA    894375 A    2/1972
DE    2652654 A1    5/1978
(Continued)

OTHER PUBLICATIONS

Unveiling the Nike Sole, Nike News, Feb. 2, 2012, https://news.nike.com/news/unveiling-the-nike-sole-for-amputee-athletes.

*Primary Examiner* — Bruce E Snow
(74) *Attorney, Agent, or Firm* — Quinn IP Law

(57) ABSTRACT

A traction system for an ambulatory support such as a prosthetic foot blade or a crutch includes a sole plate, a latch assembly, and a strap. The sole plate is couplable to a distal end of the ambulatory support to extend under a bottom side of the ambulatory support and a latch assembly. The latch assembly includes a front catch and a rear catch both fixable at a top side of the ambulatory support with the front catch nearer to the distal end of the ambulatory support than the rear catch, and a lever having a front end and a rear end, the front end releasably latchable to the front catch and the rear end releasably latchable to the rear catch when the lever is pivoted about the latched front end. The strap is secured to the lever and to the sole plate.

20 Claims, 43 Drawing Sheets

(52) U.S. Cl.
CPC .............. *A61F 2002/5038* (2013.01); *A61F 2002/5072* (2013.01); *A61F 2002/5081* (2013.01); *A61F 2002/665* (2013.01); *A61F 2002/6657* (2013.01); *A61H 2003/0211* (2013.01)

(58) Field of Classification Search
CPC ........ A61F 2002/5081; A61F 2002/665; A61F 2002/6657; A61F 2002/7862
See application file for complete search history.

(56) References Cited

U.S. PATENT DOCUMENTS

| | | | |
|---|---|---|---|
| 4,802,290 A * | 2/1989 | Marega | A43C 11/1473 36/117.7 |
| 6,228,124 B1 | 5/2001 | Slemker et al. | |
| 6,231,618 B1 | 5/2001 | Schall et al. | |
| 7,124,476 B2 * | 10/2006 | Garofalo | A44B 11/125 24/71 SK |
| 7,526,881 B2 | 5/2009 | Jones et al. | |
| 8,535,390 B1 | 9/2013 | Lecomte et al. | |
| 10,064,781 B2 | 9/2018 | Clausen et al. | |
| 10,117,758 B2 | 11/2018 | Clausen et al. | |
| 2005/0119763 A1 | 6/2005 | Christensen | |
| 2011/0099846 A1 * | 5/2011 | Fischer | A43C 11/146 36/117.1 |
| 2012/0271434 A1 * | 10/2012 | Friesen | A61F 2/66 623/55 |
| 2016/0008147 A1 | 1/2016 | Marlin | |
| 2016/0045337 A1 | 2/2016 | Mackiewicz et al. | |
| 2017/0105351 A1 | 4/2017 | Matway et al. | |
| 2017/0281371 A1 | 10/2017 | Green et al. | |
| 2021/0127781 A1 | 5/2021 | Xanthos | |

FOREIGN PATENT DOCUMENTS

| | | |
|---|---|---|
| EP | 0612484 A1 | 8/1994 |
| GB | 978586 A | 12/1964 |
| WO | 9840038 A1 | 9/1998 |
| WO | 9918895 A1 | 4/1999 |
| WO | 2016132927 A1 | 8/2016 |
| WO | 2017173200 A1 | 10/2017 |

* cited by examiner

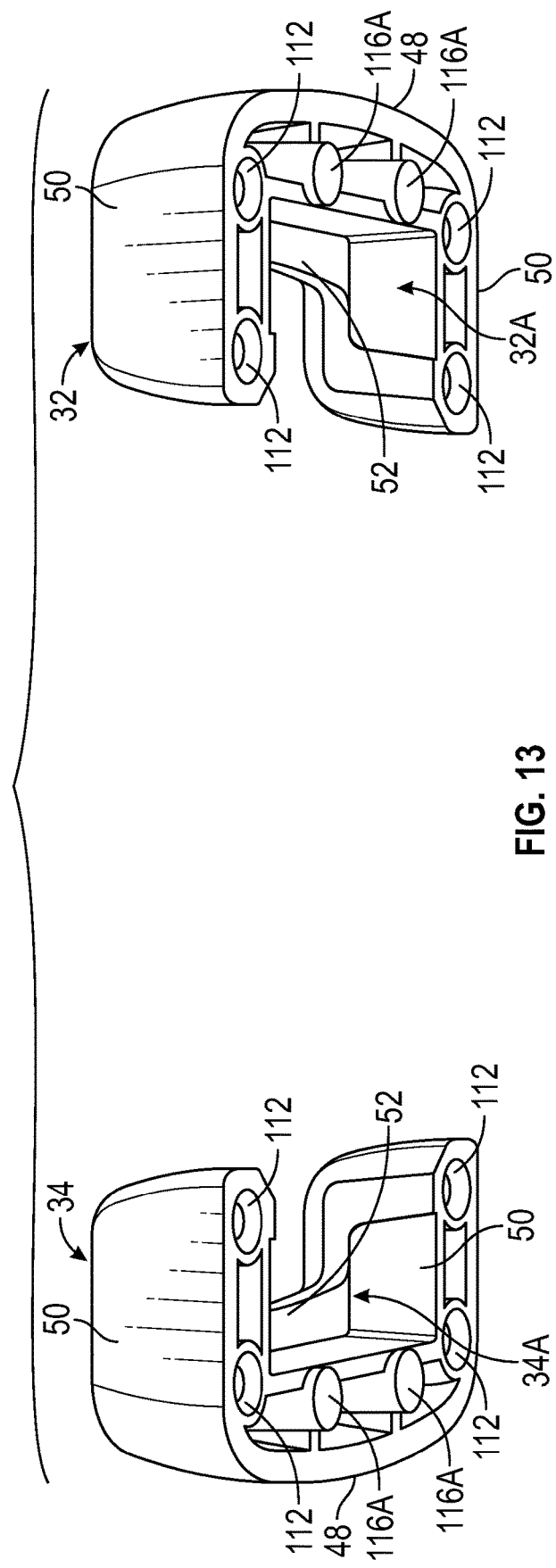
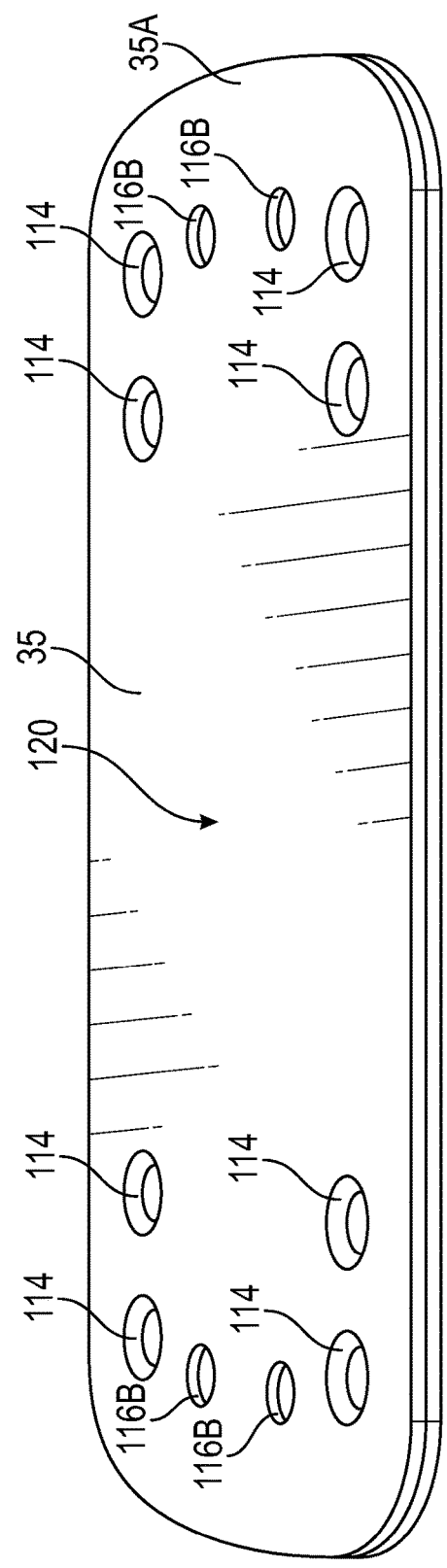
FIG. 13
FIG. 14

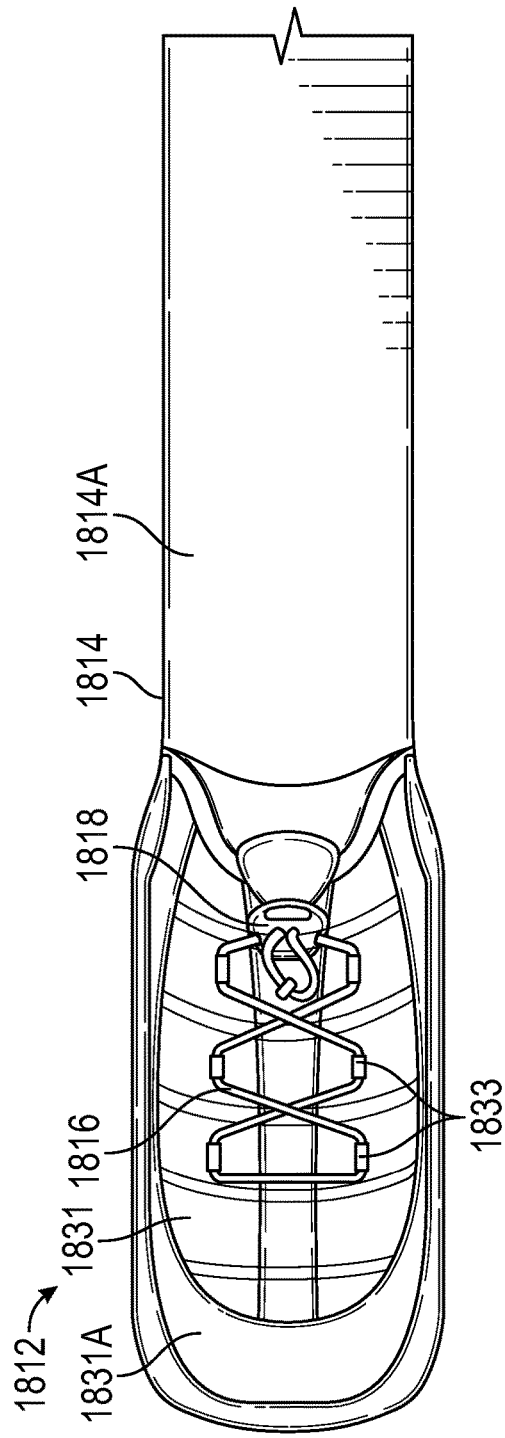
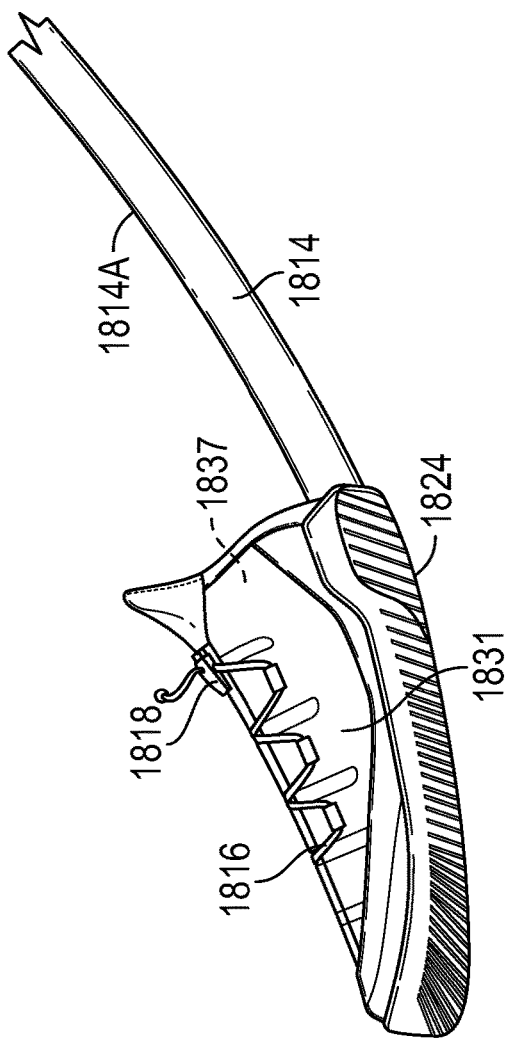

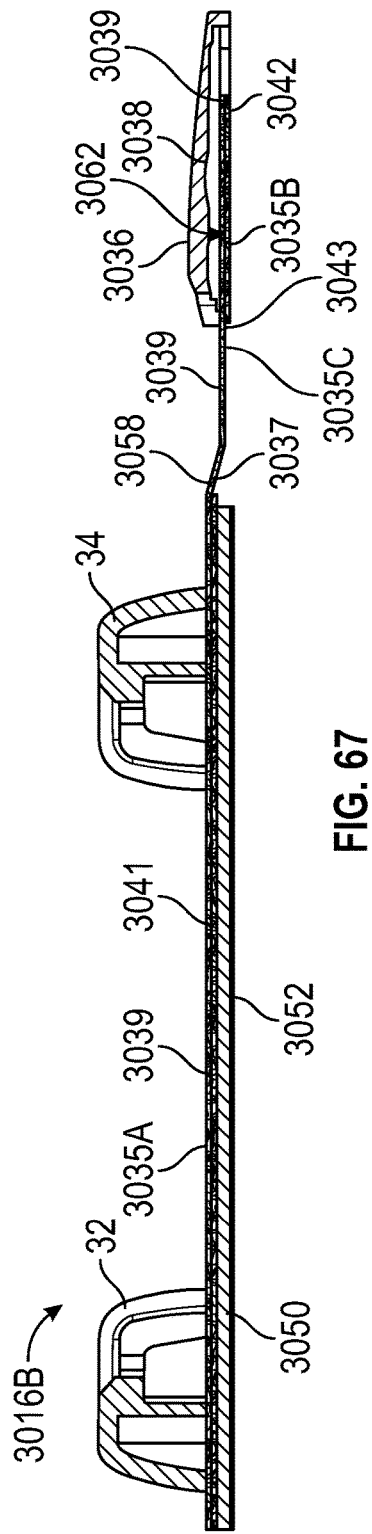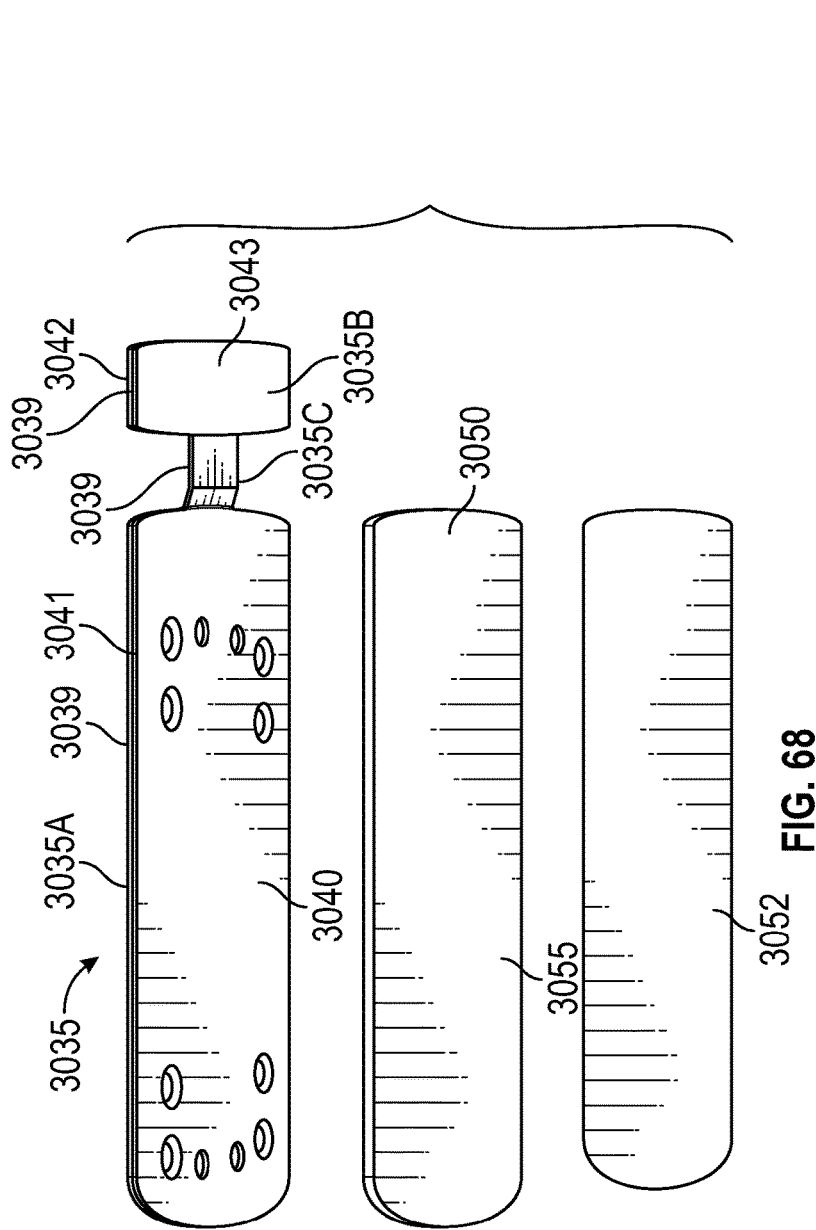
FIG. 67
FIG. 68

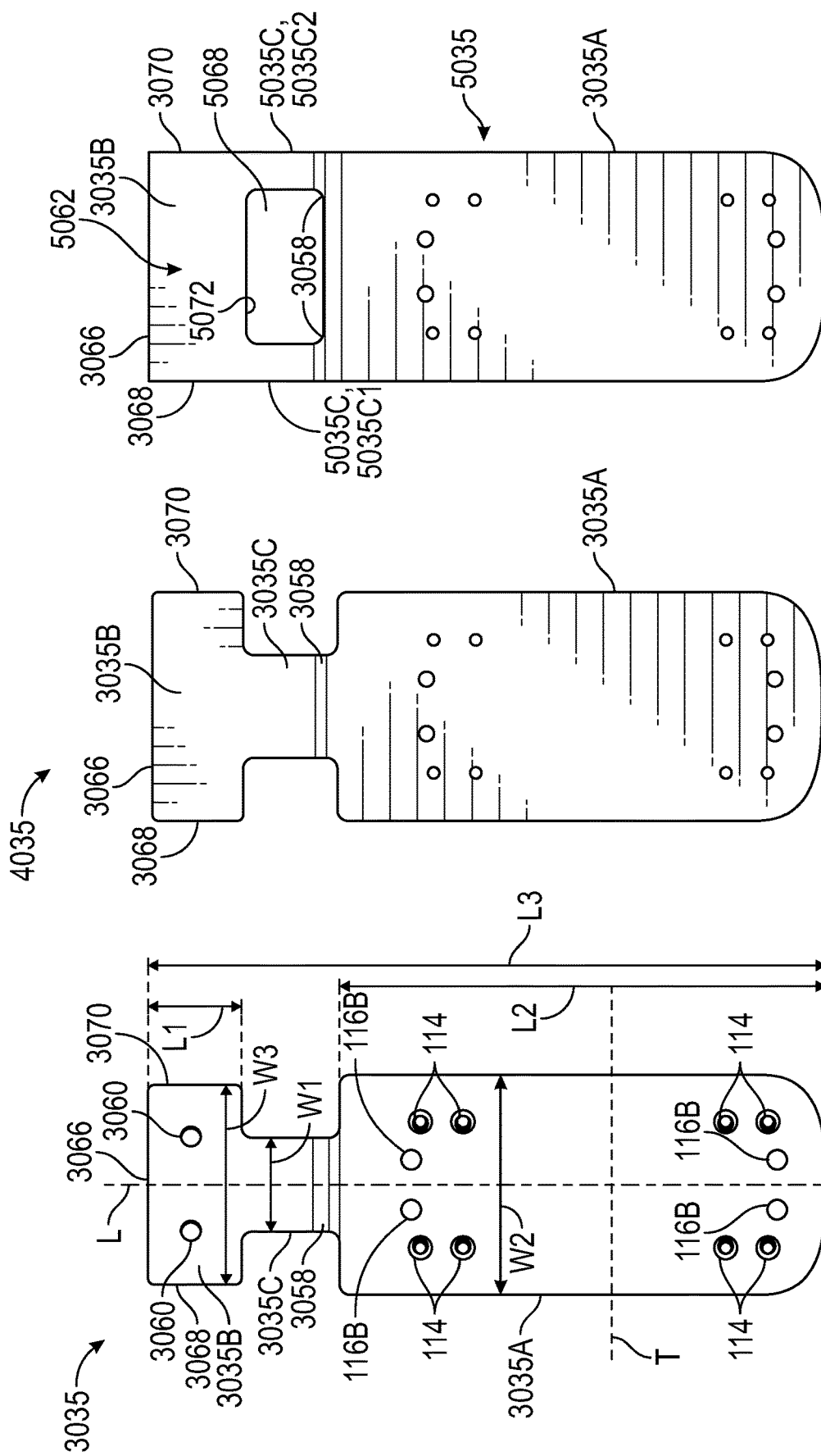

TRACTION SYSTEM FOR AN AMBULATORY SUPPORT

CROSS-REFERENCE TO RELATED APPLICATIONS

This application claims the benefit of priority to U.S. Provisional Application No. 63/004,698 filed Apr. 3, 2020, which is hereby incorporated by reference in its entirety.

TECHNICAL FIELD

The present disclosure generally relates to a traction system for an ambulatory support such as a prosthetic foot blade or a crutch.

BACKGROUND

Ambulatory supports such as crutches and prosthetic legs and feet are used to provide support, stability and mobility. Prosthetic foot blades are a particular prosthesis that can be connected to a prosthetic leg and are typically elongated with a curved profile that terminates at a distal portion that functions as a foot. Athletes in particular use prosthetic foot blades configured to resiliently bend and flex during running, for example. Similarly, some crutches have distal portions that function as feet. The traction and cushioning requirements for different terrain, walking, or running surfaces vary. Additionally, traction and cushioning requirements may vary according to running distance.

BRIEF DESCRIPTION OF THE DRAWINGS

The drawings described herein are for illustrative purposes only, are schematic in nature, and are intended to be exemplary rather than to limit the scope of the disclosure.

FIG. 13 is a bottom perspective view of front and rear catches of the latch assembly.

FIG. 14 is a perspective view of the bottom of a latch base of the latch assembly.

FIG. 53 is a top fragmentary view of an alternative sole plate for the prosthetic foot blade of FIG. 52.

FIG. 54 is a fragmentary side view of the sole plate of FIG. 53.

FIG. 67 is a cross-sectional view of the latch mount of FIG. 64 taken at lines 67-67 in FIG. 64.

FIG. 68 is an exploded view of the latch base, a compressible layer, and double-sided adhesive tape included in the latch mount of FIG. 67.

FIG. 69 is a plan view of the latch base of FIG. 68.

FIG. 70 is a plan view of an alternative latch base.

FIG. 71 is a plan view of an alternative latch base.

DESCRIPTION

Figure 1:
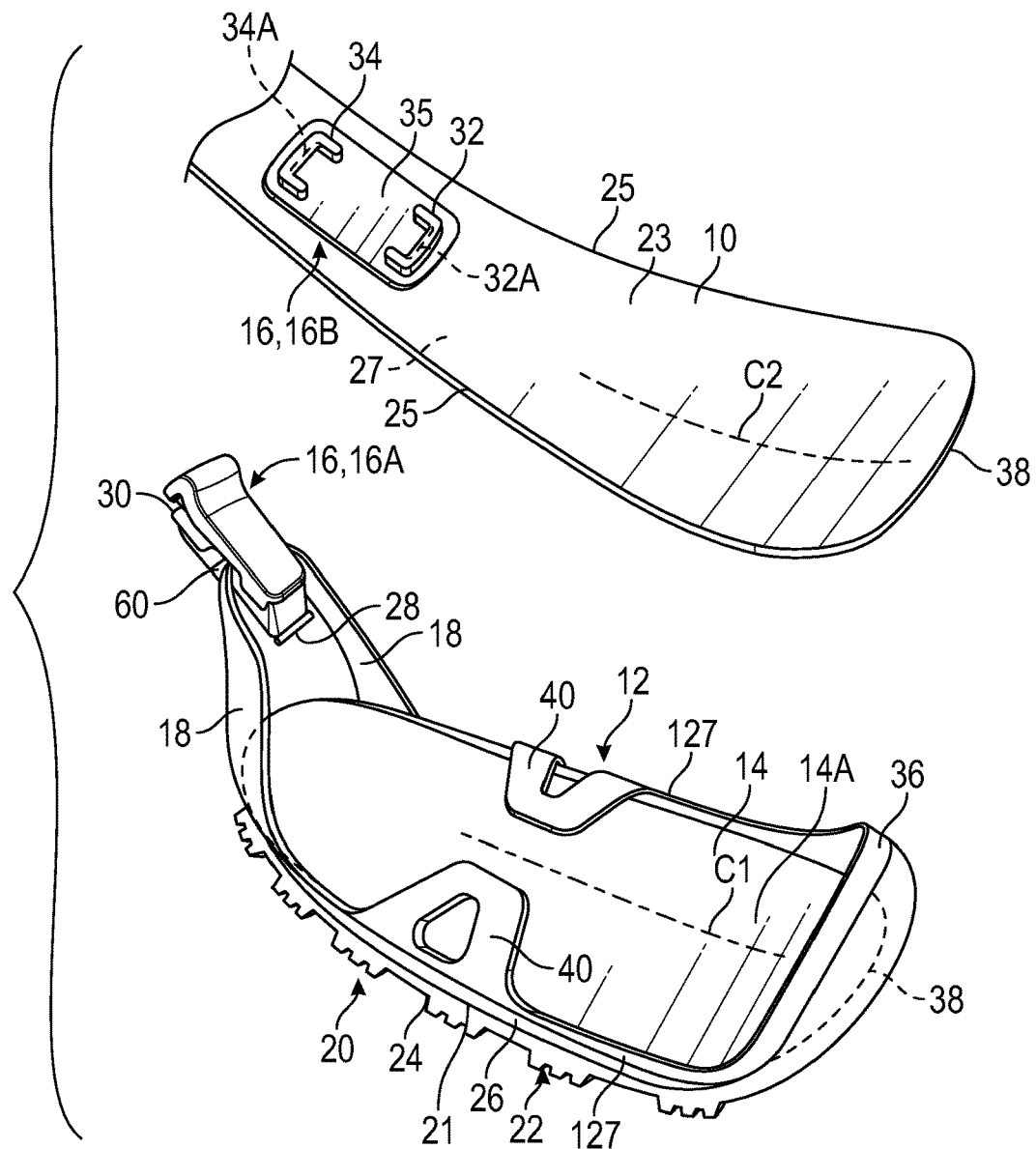
FIG. 1 is a fragmentary perspective partially exploded view of a prosthetic foot blade and a traction system for the prosthetic foot blade, including a sole plate, a strap, and a latch assembly, with the latch assembly in an unlatched state.

The present disclosure generally relates to traction systems for ambulatory supports such as prosthetic foot blades and crutches. More particularly, traction systems disclosed herein are releasably attachable to ambulatory supports to enable both secure retention to the ambulatory support during use and relatively easy and quick removal to allow, for example, the use of different traction systems for different activities or on different ground surfaces.

In an example traction system for an ambulatory support, the traction system may include a sole plate couplable to a distal end of the ambulatory support to extend under a bottom side of the ambulatory support. The traction system may further include a latch assembly that has a front catch and a rear catch both fixable at a top side of the ambulatory support with the front catch nearer to the distal end of the ambulatory support than the rear catch. The latch assembly may include a lever having a front end and a rear end, the front end releasably latchable to the front catch and the rear end releasably latchable to the rear catch when the lever is pivoted about the latched front end. Such a latch assembly may be referred to as an off-center draw latch. The traction system may include a strap secured to the lever and to the sole plate and placed in tension when the sole plate is coupled to the distal end of the ambulatory support and the lever is latched at the front end and the rear end. The strap pulls the sole plate against the distal end and the bottom side of the ambulatory support. Other sole layers may be secured to the sole plate to provide a ground-engaging surface or the sole plate itself may provide the ground-engaging surface. Particular ambulatory supports with which any of the traction systems disclosed herein may be implemented include prosthetic foot blades and certain crutches (e.g., crutches having an elongate member with a curved distal portion having a distal end and serving as a foot portion).

Other example features of an ambulatory support traction system disclosed herein may include the strap extending through the lever between the front end and the rear end. For example, the lever may have opposing side walls each having an aperture disposed between the front end and the rear end. The strap may extend through the lever at the apertures. In a different example latch assembly, a ring may be secured to the lever rearward of the front end, and the strap may extend through the ring. In another example, the strap may be secured to the bottom side of the sole plate between the sole plate and at least one sole layer (such as a midsole and/or an outsole) that is also secured at the bottom side of the sole plate and includes a ground-engaging traction surface.

The sole plate may include certain features, such as a front wall disposed forward of the distal end of the ambulatory support and a toe cap extending rearward from the front wall over the top side of the ambulatory support when the sole plate is secured to the ambulatory support. The front wall and toe cap act as a forward end barrier to properly locate the ambulatory support on the sole plate during the attachment process. Additionally, a bottom wall of the sole plate may be sufficiently flexible to move from a relatively flat state to a relatively curved state to conform with a curvature of the bottom side of the ambulatory support when the strap is placed in tension. The sole plate will thus be placed in tension when the traction assembly is latched to the ambulatory support, decreasing the likelihood of any jiggling of the sole plate against the ambulatory support and associated rattle. The sole plate may also include integral side clamps that extend around opposing sides of the ambulatory support and over the top side of the ambulatory support when the sole plate is coupled to the ambulatory support. The side clamps may provide sufficient clamping force to retain the sole plate on the ambulatory support even when the latch assembly is unlatched. The bottom of the sole plate may also include recesses at which the strap is secured to the sole plate so that the strap is partially housed in the recesses.

In another aspect, the latch assembly may include a latch base fixable to the top side of the ambulatory support with the front and rear catches secured to the latch base. The latch base may be adhered or otherwise secured to the ambulatory support, and the catches may be fastened to the latch base. The latch base may be relatively thin to enable some flexing with the underlying ambulatory support and to avoid adding stiffness to the ambulatory support. In some examples, the latch base may be configured as a plate, such as a composite plate. Additionally, the latch base may have a larger surface area than if the catches were directly attached to the ambulatory support, providing a greater bonding surface area to widely disperse pulling forces of the strap. For example, a portion of the latch base may extend forward of the front catch along the top side of the ambulatory support. The latch base may also extend further rearward than the rear catch, and transversely outward of the catches.

Because the top side of the ambulatory support experiences compressive stress during dynamic loading of the ambulatory support, such as when a wearer is moving forward with the ambulatory support in contact with a ground surface, the latch base may be configured to reduce resulting compressive stress and shear stress on the latch base in comparison to a latch base of uniform width and/or flexibility along its length. In an example, the latch base may include a plate portion, an anchor portion, and a hinge portion flexibly connecting the plate portion and the anchor portion. The front and rear catches may be secured to the plate portion. The anchor portion may be fixed relative to the top side of the ambulatory support and the hinge portion may be disposed above and unfixed to the top side of the ambulatory support when the latch base is secured to the ambulatory support. For example, the hinge portion may be relatively flexible and/or soft.

Because the latch base is disposed on the top side of the ambulatory support, it will experience compression during longitudinal bending of the ambulatory support, such as when loaded by a wearer during use. This configuration of a latch base more easily compresses because the hinge portion is unfixed to (e.g., floats over) the top side of the ambulatory support, as the ambulatory support flexes during use (e.g., bends along its length). The hinge portion can easily flex in response, reducing the resistance to compression and associated shear forces on the latch base in comparison to a latch base configured as a flat plate along its entire length (e.g., without a hinge portion).

The hinge portion may be at least partially spaced apart from the top side of the ambulatory support when the ambulatory support is in a relatively unloaded state. In an example, the hinge portion may be sufficiently flexible so that it moves from a spaced apart position into contact with the top side of the ambulatory support.

In an example, the hinge portion may be either or both of narrower and thinner than the plate portion and the anchor portion. Additionally, the anchor portion may be shorter than the plate portion. These features promote flexibility and reduce compressive stress experienced by the latch base. The relatively narrow hinge portion (i.e., in transverse width along the width of the ambulatory support) promotes flexibility and relative movement of the plate portion and the anchor portion.

The hinge portion may include only a single strip connecting the plate portion and the anchor portion, or may include two or more strips spaced transversely apart from one another and connecting the plate portion and the anchor portion.

The latch base may comprise a composite material, such as at least one of a carbon fiber composite or a glass fiber composite. In an example, the latch base comprises layers of composite material, with fewer layers at the hinge portion, resulting in its greater flexibility. For example, the latch base may comprise at least one layer of composite sheet material at the hinge portion, and a greater number of layers of composite sheet material at the anchor portion and at the plate portion.

The hinge portion may extend rearward from the plate portion over the top side of the ambulatory support, and the anchor portion may be disposed rearward of the hinge portion when the latch base is secured to the ambulatory support.

In an implementation, a compressible layer may be secured to the bottom side of the plate portion and disposed at the top side of the ambulatory support plate when the latch base is secured to the ambulatory support. For example, the compressible layer may comprise foam. The compressible layer allows the plate portion to effectively float above the top side of the ambulatory support as the compressible layer can resiliently compress during longitudinal bending of the ambulatory support, minimizing the compressive force of the ambulatory support transferred to the plate portion.

In an implementation, the compressible layer may be unfixed to the top side of the ambulatory support and held against the top side of the ambulatory support by tension in the strap when the lever is latched. For example, there may be no adhesive, fasteners, or other securing features securing the compressible layer to the top side, with only the tensioned strap holding the compressible layer against the top side. Alternatively, the compressible layer may be secured to the top side of the ambulatory support to further secure the latch base to the ambulatory support. In one example, a double-sided adhesive layer may be disposed between the compressible layer and the top side of the ambulatory support when the latch base is secured to the ambulatory support.

In an aspect, the mount may have through holes extending through the latch base, and adhesive may extend through the through holes, and over at least a portion of a top surface of latch base when the latch base is secured to the ambulatory support. The adhesive may extend on the bottom side of the latch base, such as between the latch base and the top side of the ambulatory support. With the adhesive extending not only between the bottom side of the latch base and the top side of the ambulatory support, but also through the latch base and onto the top surface of the latch base, the adhesive, when cured or otherwise in a final state, has a structure that serves as a mechanical attachment, such as a fastener or an end stop.

In a configuration of the latch base having the anchor portion, for example, the through holes may extend through the anchor portion. In another aspect, adhesive may extend between the anchor portion and the top side of the ambulatory support, and around an outer edge of the anchor portion when the latch base is secured to the ambulatory support. For example, the adhesive may thus serve as a mechanical end stop at the outer edge of the anchor portion. The outer edge may include a top edge and side edges, and the adhesive therefore forming a three-sided or T-stop. In some examples, a cover may be secured over the anchor portion. The cover may serve to improve aesthetics, such as by covering the adhesive.

In an example, the latch base may be a flat plate along its entire length, or may be the latch base with the flexible hinge portion as described, and at least some of the through holes may be disposed forward of the front catch and/or at least some of the through holes may be disposed rearward of the rear catch. Similar to the through holes in an anchor portion as described, the through holes disposed in these positions enable the adhesive to act as a mechanical stop. In an aspect, adhesive may be disposed along a front edge of the latch base forward of the front catch and/or along a rear edge of the latch base rearward of the rear catch when the latch base is secured to the ambulatory support.

In an implementation, the latch base may include a front section and a rear section with a rear edge of the front section split from a front edge of the rear section. Sectioning the latch base with such a transverse split lessens the length along the ambulatory support that each section of the latch base divided by the split extends. For example, sectioning the latch base effectively splits the latch base from a configuration as a relatively long plate to two or more shorter plates. This reduces the compressive forces on each such section of the latch base during dynamic loading of the ambulatory support, for example.

A traction system for an ambulatory support may include a latch assembly operable to latch a sole plate to a distal end of the ambulatory support. The latch assembly may include a latch base fixable at a top side of the ambulatory support. The latch base may include a plate portion, an anchor portion, and a hinge portion flexibly connecting the plate portion and the anchor portion. The anchor portion may be fixable relative to the top side of the ambulatory support and the hinge portion may be disposed above and unfixed to the top side of the ambulatory support when the latch base is secured to the ambulatory support.

Various latch assemblies are disclosed herein. In one example, latch assembly, the front catch may define a front pocket opening toward the rear catch and the rear catch may define a rear pocket opening toward the front catch. The front end of the lever may include a front lip captured in the front pocket when the front end latches to the front catch and the rear end of the lever may include a rear lip captured in the rear pocket when the rear end latches to the rear catch. The latch assembly may bias the front and rear end apart from one another (e.g., biased apart along the length of the ambulatory support), to help maintain the ends in the respective catches when latched. For example, the lever may include a first latch body that includes the front end of the lever and a second latch body coupled to the first latch body and that includes the rear end of the lever. The second latch body may cover a substantial portion of the first latch body, and so may be referred to as a latch cover. A biasing member such as a compression spring may engage the first latch body and the second latch body and bias the front end apart from the rear end, with the front end movable toward the rear end to release the lever from the rear catch under an applied force (e.g., a force applied by the user) opposing a force of the biasing member. Such a latch assembly may be referred to as a spring-loaded, off-center draw latch. The lever may include a grip protruding at the rear end to help facilitate release of the lever.

In one implementation, the first latch body may include an intermediate wall disposed rearward of the front end, the second latch body may include a protrusion disposed between the front end and the intermediate wall, and the biasing member may be disposed between the rear end and the intermediate wall, biasing the intermediate wall against the protrusion. To further interconnect the first and second latch bodies, the first latch body may have side walls and the second latch body may have side walls disposed adjacent to (e.g., outward of) the side walls of the first latch body. The side walls of one of the first latch body and the second latch body may include flanges, and the side walls of the other of the first latch body and the second latch body may include slots, with the flanges fitting within the slots.

The strap may be relatively inelastic in order to promote strong tensile forces in the strap that pull the sole plate firmly against the bottom side of the ambulatory support. In order to fine tune the tension in the strap, the traction system may include an adjustment screw extending longitudinally within the lever and interfacing with the strap. A position of the adjustment screw may be adjustable to adjust tension in the strap.

A further example traction system for an ambulatory support includes a sole plate couplable to a distal end of the ambulatory support to extend under a bottom side of the ambulatory support, an off-center draw latch assembly having a catch securable at a top side of the ambulatory support and having a lever releasably latchable to the catch, and a strap secured to the lever and to the sole plate and placed in tension when the sole plate is coupled to the distal end of the ambulatory support and the lever is latched to the catch, the strap pulling the sole plate against the distal end and the bottom side of the ambulatory support.

Other example ambulatory support traction systems use attachment systems other than latches. For example, a traction system for an ambulatory support may include a sole plate couplable to a distal end of the ambulatory support to extend under a bottom side of the ambulatory support, and may further include an attachment system that includes a threaded post extending from the sole plate and a knob securable to an end of the threaded post. The ambulatory support may define a through hole extending through the ambulatory support from the bottom side to a top side of the ambulatory support. The threaded post may extend through the through hole when the sole plate is coupled to the distal end of the ambulatory support, and the sole plate is retained against the bottom side of the ambulatory support when the knob is secured to the threaded post. In an example, a boss may extend from the top side of the ambulatory support, the through hole may extend through the boss with a longitudinal axis of the through hole at an acute angle to the top side of the ambulatory support.

For convenience, the traction system may include various features to retain the knob to the ambulatory support even when the knob is not secured to the threaded post. For example, the traction system may include a tether secured to the knob and securable to the top side of the ambulatory support to secure the knob to the ambulatory support. In another example, the traction system is configured so that the knob is a captive knob. A boss may extend from the top side of the ambulatory support and the through hole may extend through the boss. The knob may be retained by the boss regardless of whether the knob is secured to the end of the threaded post. For example, the knob may fit through the through hole but a shank portion of the knob may have a flange larger than the through hole to retain the knob to the boss.

The above features and advantages and other features and advantages of the present teachings are readily apparent from the following detailed description of the modes for carrying out the present teachings when taken in connection with the accompanying drawings. It should be understood that even though in the following Figures embodiments may be separately described, single features thereof may be combined to additional embodiments.

Referring to the drawings, wherein like reference numerals refer to like components, FIG. 1 shows an ambulatory support 10 and a traction system 12 shown detached from the ambulatory support 10. In the example shown, the ambulatory support 10 particularly is a prosthetic foot blade 10 and is referred to herein as such. It should be appreciated that any of the traction systems herein that are disclosed herein for use with a prosthetic foot blade are equally applicable for use with a crutch having an elongate member with a distal portion, such as crutch 10A in FIG. 6.

The traction system 12 includes a sole plate 14, at least one latch assembly 16, and at least one strap 18. The sole plate 14 may also be referred to as a base or a tray, and forms a portion of a sole structure 20. The strap 18 is secured to the latch assembly 16 and to the sole plate 14 as discussed herein.

The latch assembly 16 is particularly configured as a spring-biased, over-center draw latch and has a lever 16A shown detached from the prosthetic foot blade 10 in FIG. 1, and a latch mount 16B secured to the top side 23 of the prosthetic foot blade 10 even when the traction system 12 is detached with the latch assembly 16 in the unlatched state of FIG. 1.

Figure 3:
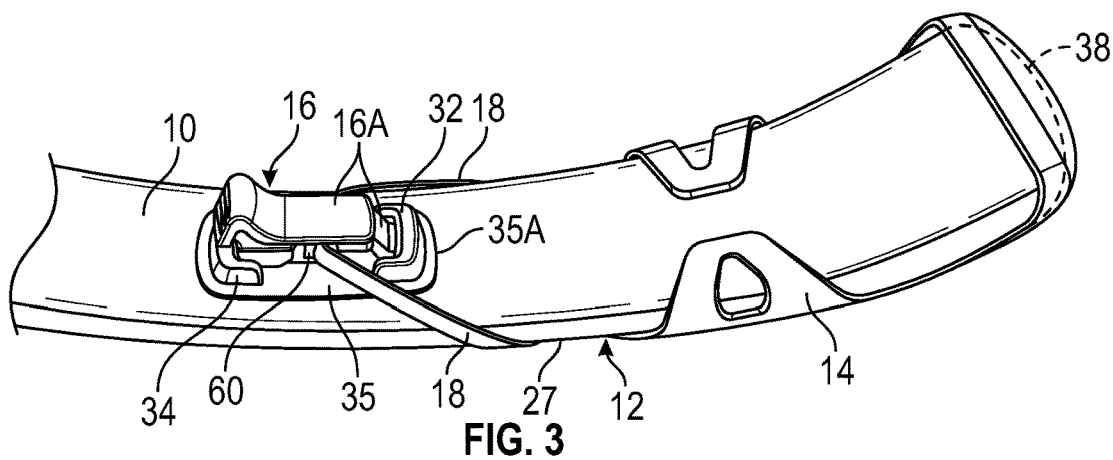
FIG. 3 is a perspective view of the traction system coupled to the prosthetic foot blade, shown in fragmentary view, with the latch assembly in a latched state.
Figure 4:
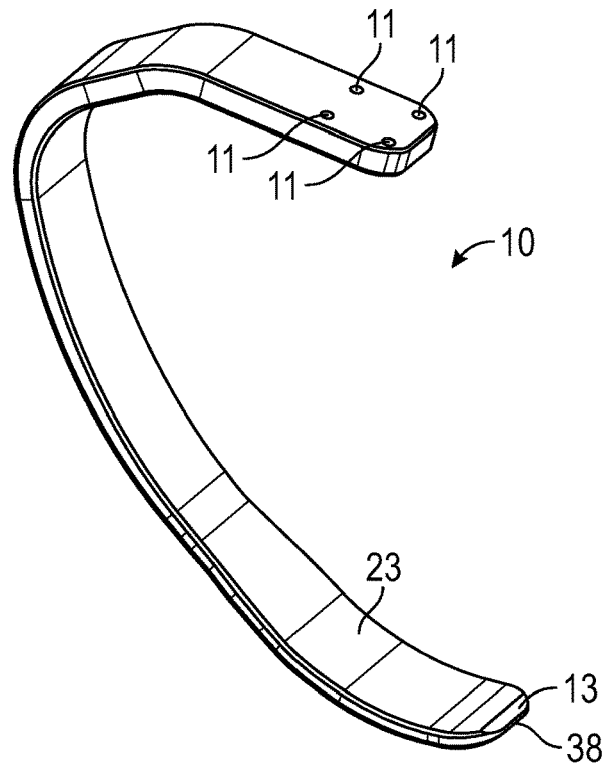
FIG. 4 is a perspective view of the prosthetic foot blade.

The strap 18 is placed or is placeable in tension as discussed herein when the sole plate 14 is fitted to the prosthetic foot blade 10 and the latch assembly 16 is latched to couple the sole plate 14 to the prosthetic foot blade 10, as shown in FIG. 3. Because the traction system 12 is configured to be easily and quickly secured to and removed from the prosthetic foot blade 10, the wearer can utilize different traction systems for different uses and activities when wearing the prosthetic foot blade 10. Only a portion of the prosthetic foot blade 10 is shown near its distal end 38 (e.g., the portion that interacts with the ground). The entire foot blade 10, including a proximal end of the prosthetic foot blade 10, is shown in FIG. 4. The proximal end is configured to secure to a prosthetic leg by any mounting mechanism, such as by a fastener that secures through one or more apertures 11 at the proximal end.

The traction system 12 may further include at least one sole layer secured or securable at the bottom side 21 of the sole plate 14 and at least partially establishing a ground-engaging surface 22 of the traction system 12. The traction system 12 of FIG. 1 particularly includes two or more sole layers secured or securable at the bottom side 21 (also referred to as the second side) of the sole plate 14: an outsole 24 establishing the ground-engaging surface 22, and a midsole 26 secured or securable to the outsole and to the bottom side 21 of the sole plate 14. Additionally, in some implementations of any of the traction systems disclosed herein, an interface layer particularly configured to enhance grip and reduce slip may be provided at a top side of the sole plate 14 to interface with the bottom side 27 of the prosthetic foot blade 10. For example, in the traction system 12, an interface layer may be secured on the top side 14A of the sole plate 14, and may be a material such as a thermoplastic polyurethane. Other traction systems that may be alternately attached to the prosthetic foot blade 10 as disclosed herein include traction systems with a spiked plate, or with different outsole tread patterns, etc.

First and second ends (particularly being front and rear ends 28, 30, respectively, and referred to herein as such) of the lever 16A latch to respective first and second catches (particularly being front and rear catches 32, 34, and referred to herein as such) of the latch mount 16B, retained at pockets 32A, 34A of the catches 32, 34 as further discussed herein.

The catches 32, 34 are secured or securable to a latch base 35, also referred to herein as a latch base 35, that is fixed to the top side 23 of the prosthetic foot blade 10. Additional features of the sole plate 14 that help retain it to the prosthetic foot blade 10 particularly include a toe cap 36 that at least partly fits over a distal end 38 of the prosthetic foot blade 10, and/or one or more integral side clamps 40 that are arranged at (particularly extend around) lateral sides (particularly substantially opposing sides) 25 of the prosthetic foot blade 10 and/or over the top side 23 of the prosthetic foot blade 10.

The sole plate 14 is coupled to the prosthetic foot blade 10 by sliding the prosthetic foot blade 10 under the clamps 40 and substantially toward the toe cap 36 so that the sole plate 14 is at the bottom side 27 of the prosthetic foot blade 10 with the toe cap 36 over the distal end 38. The chamfer 13 of the prosthetic foot blade 10 shown in FIG. 5 and discussed herein particularly provides a lead in for the prosthetic foot blade 10 in interfacing with the clamps 40, easing the forward sliding of the prosthetic foot blade 10 relative to the sole plate 14 during securement of the sole plate 14 to the prosthetic foot blade 10. The prosthetic foot blade 10 slides between the clamps 40 and the top side 23 (also referred to as a first side) of the sole plate 14.

The sole plate 14 has a front wall 33 (see FIG. 5) substantially disposed forward of the distal end 38 of the prosthetic foot blade 10 and the toe cap 36 substantially extending rearward from the front wall 33 over the top side 23 of the prosthetic foot blade 10 when the sole plate 14 is secured to the prosthetic foot blade 10. The front wall 33 and/or the toe cap 36 act as a forward end barrier, stopping the forward slide of the prosthetic foot blade 10 on the sole plate 14 to properly locate the prosthetic foot blade 10 on the sole plate 14 during the attachment process.

Figure 5:
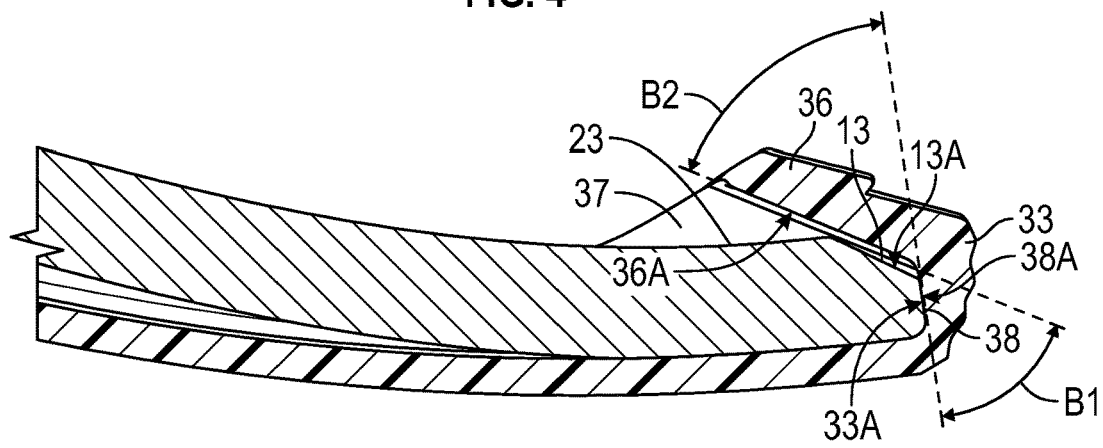
FIG. 5 is a fragmentary cross-sectional view of the sole plate secured to the prosthetic foot blade, taken at lines 5-5 in FIG. 2.

Referring to FIG. 4, the top side 23 of the prosthetic foot blade 10 includes the chamfer 13 at the distal end 38. As shown in FIG. 5, an angle B1 between a surface 13A of the chamfer 13 and a surface 38A of the distal end 38 is equal to or substantially equal to an angle B2 between an inner surface 36A of the toe cap 36 and an inner surface 33A of the front wall 33 of the sole plate 14. By way of non-limiting example, the angle B1 could be from about 30 degrees to about 60 degrees. In the example shown, the angle B1 is 60 degrees and the angle B2 is 60 degrees.

As shown, the toe cap 36 and front wall 33 define a cavity 37 into which the distal end 38 of the prosthetic foot blade 10 fits. The chamfer 13 of the prosthetic foot blade 10 and the corresponding angle B2 of the inner surface 36A to the inner surface 33A particularly contribute to a wedging of the prosthetic foot blade 10 to the sole plate 14 when tension is applied to the strap 18 as discussed herein, advantageously eliminating play that could be associated with a variation in a thickness of the prosthetic foot blade 10 or a variation in dimension of the sole plate 14 at the cavity 37. Accordingly, the chamfer 13 of the blade interfitting with the sole plate 14 at the cavity 37 creates a mechanical lock of the sole plate 14 to the prosthetic foot blade 10 when tension is applied due to the strap 18 and the latch assembly 16.

Referring to FIG. 1, when not secured to the prosthetic foot blade 10, the sole plate 14 may have only a slight curvature C1 or may be relatively flat at its top side 14A in the longitudinal direction in comparison to a greater curvature C2 of the prosthetic foot blade 10 near the distal end 38 when the prosthetic foot blade 10 is not under dynamic compression. The sole plate 14 is sufficiently flexible to adopt to the curvature C2 of the prosthetic foot blade 10 when disposed thereon and latched thereto via the strap 18 and latch assembly 16, decreasing any likelihood of relative movement and associated rattle. For example, the sole plate 14 may be plastic. Alternatively, the curvature C1 of the sole plate 14 may substantially match the curvature C2 of the prosthetic foot blade 10 even when not secured to the prosthetic foot blade 10. Moreover, the flexibility of the sole plate 14 allows it to flex with the prosthetic foot blade 10 during dynamic loading of the prosthetic foot blade 10 (e.g., with an increased curvature of the prosthetic foot blade 10 during dorsiflexion and toe-off, such as when a wearer is moving forward with the prosthetic foot blade 10 in contact with a ground surface).

Figure 2:
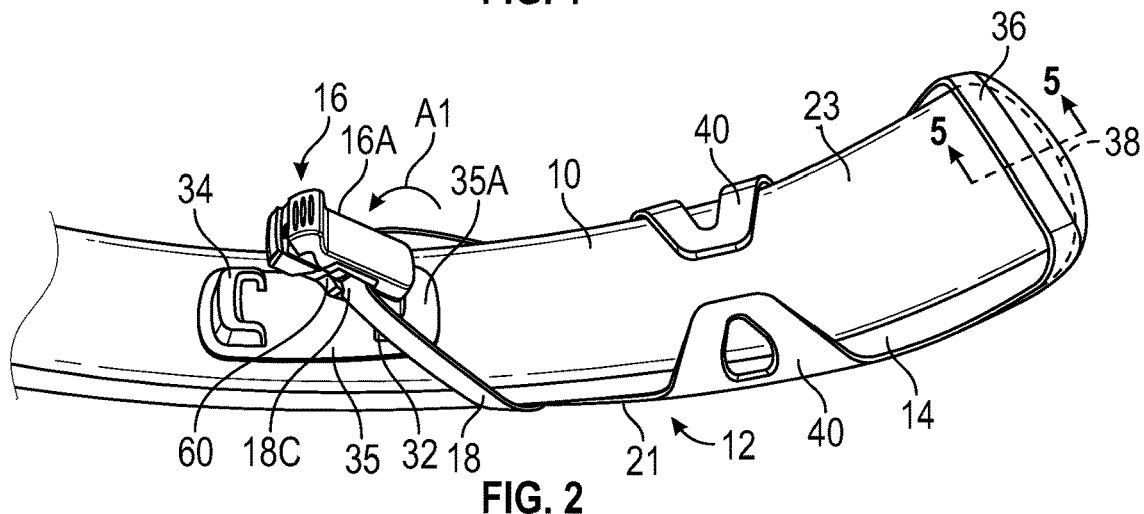
FIG. 2 is a perspective view of the traction system coupled to the prosthetic foot blade, shown in fragmentary view, with the latch assembly in a partially latched state.

FIG. 2 shows the sole plate 14 fitted on the prosthetic foot blade 10 with the latch assembly 16 in a partially latched state. The first (front) end 28 (see FIG. 1) of the lever 16A has been latched to the first (front) catch 32 and the lever 16A is being pivoted particularly rearward about its front end 28 (e.g., in the direction of arrow A1) using the front catch 32 as a hinge joint. FIG. 3 shows the lever 16A in a fully latched state, tensioning the strap 18 which pulls the sole plate 14 against the distal end 38 and against the bottom side 27 of the prosthetic foot blade 10. The outsole 24 and the midsole 26 are not shown on the sole plate 14 in FIG. 3.

Figure 6:
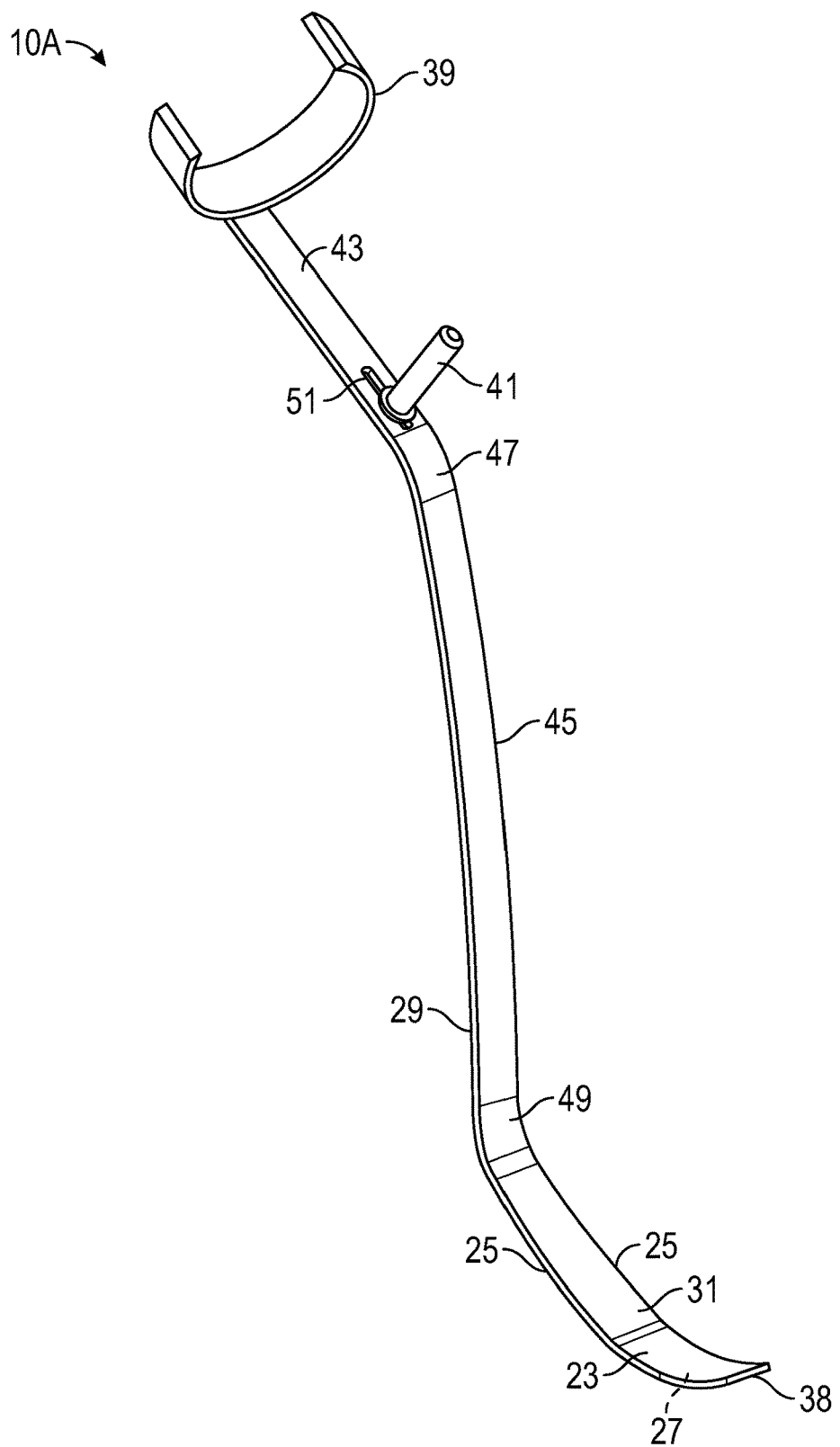
FIG. 6 is a perspective view of a crutch for use with any of the traction systems herein.

FIG. 6 shows an ambulatory support that particularly is a crutch 10A. The crutch 10A includes an elongate member 29 that has a distal portion 31 (e.g., a foot portion) with a distal end 38, a top side 23, a bottom side 27, and opposing sides 25 as described with respect to the same features of the prosthetic foot blade 10 that are referred to with like reference numbers. Any of the traction systems described herein can be used with a crutch in like manner as described with respect to a prosthetic foot blade having the same features. As described with respect to like crutch 100 in U.S. Pat. No. 10,064,781 issued Sep. 4, 2018 to Clausen et al., and which is hereby incorporated by reference in its entirety, crutch 10A is configured to provide energy storage and return to a user during ambulation. The crutch 10A is designed to efficiently store and release energy produced during ambulation to improve crutch assistance and ease of use. Additional crutches are also disclosed in U.S. Pat. No. 10,064,781 and may be used with the traction systems described herein.

The crutch 10A includes the elongate member 29, an arm cuff 39 and a hand grip 41. The elongate member 29 particularly includes a proximal portion 43, a central portion 45 distally connected to the proximal portion 43 via a first transition section 47 and extending at an angle relative to the central portion 45, and a curved distal portion 31 distally connected to the central portion 45 via a second transition section 49. The arm cuff 39 is shown for use with a left arm, but a like crutch 10A could have an arm cuff configured for use with a right arm. Any or all of the proximal portion 43, central portion 45, and the curved distal portion 31 can be identical whether the crutch 10A is for a right arm or a left arm, or these components could be oriented medially or laterally, respectively, to aid in ambulation.

According to some aspects, the elongate member 29 can be a single, shaped member. For example, the first and second transition sections 47, 49 can include bends in the elongate member 29. In some aspects, the elongate member 29 can be a combination of two or more attached portions. For example, the elongate member 29 can include one or more joints that can connect one or more portions of the elongate member 29.

The arm cuff 39 is proximately attached to the proximal portion 43 and can couple to an arm of a user or below the user's elbow. The hand grip 41 is attached to and extends outwardly from the proximal portion 43 at a location distal of the arm cuff 39. In some examples, the hand grip 41 can be attached to the first transition section 47 and/or the central portion 45. In some instances, a hand grip is not included in the crutch 10A but may be an optional attachment. The crutch 10A can include an aperture 51 disposed within the proximal portion 43 where the position of the hand grip 41 is slidably adjustable along the aperture 51. In some examples, the hand grip 41 can be locked into position after an adjustment is made.

The curved distal portion 31 can have an overall curved profile and can advantageously absorb and release energy to assist in propelling the user forward during use, thereby improving user performance. For example, responsive to vertical forces generated during ambulation, the curved distal portion 31 can flex and provide energy return to the user at push-off. In some examples, substantially vertical forces generated at the start of ambulation are stored and at least partly translated into a linear motion. This action reduces the need for the user to actively push his or her body forward using the crutch 10A and also can equalize stride length. In addition, it can provide for a more natural gait and reduced crutching and/or walking effort.

The elongate member 29 can be made of a composite material (such as a carbon fiber composite, a glass fiber composite, or a carbon-glass fiber composite). In some examples, the elongate member 29 can be made of other suitable materials (e.g., metals, such as aluminum, steel, or titanium).

Figure 7:
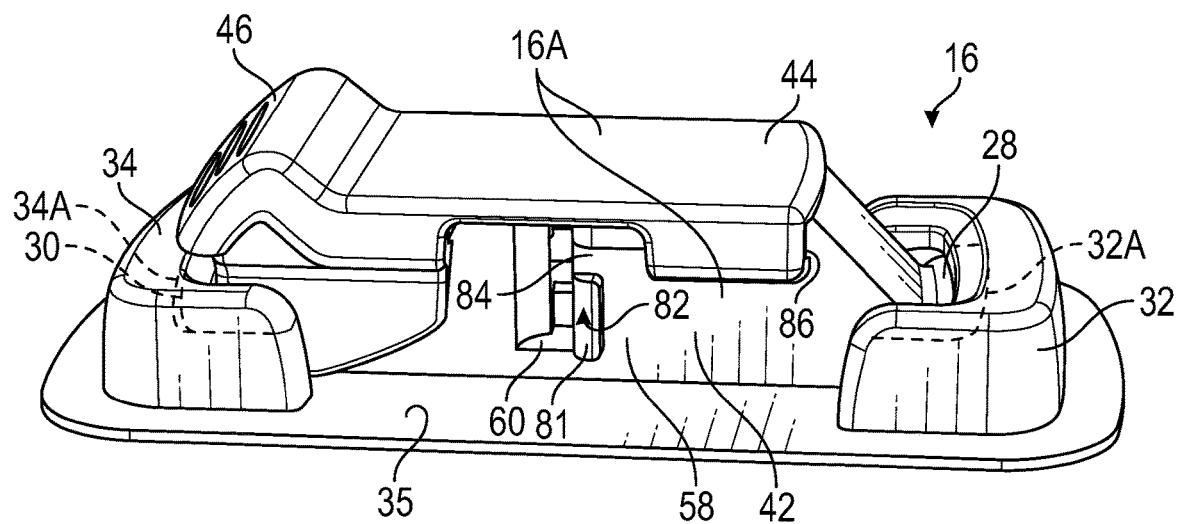
FIG. 7 is a perspective side view of the latch assembly.

FIG. 7 is a perspective side view of the latch assembly 16. The lever 16A includes a first latch body 42 and a second latch body 44 coupled to the first latch body 42. The first latch body 42 particularly includes the front end 28 of the lever 16A. The first latch body 42 may be a single (one-piece) body that forms the front end 28. Because the lever 16A is pivoted under tension at the front end 28 during latching, the first latch body 42 may be made of a sufficiently strong material such as but not limited to steel or aluminum.

Specifically, the second latch body 44 partly covers the first latch body 42 when coupled to the first latch body 42, defining most of the top surface of the lever 16A. Accordingly, the second latch body 44 may be referred to as a latch cover. The second latch body 44 includes the rear end 30 of the lever 16A (best shown in FIG. 10), and includes a grip 46 protruding at the rear end 30 when the lever 16A is latched at the rear end 30.

A biasing member (such as a spring) 88 disposed between the latch bodies 42, 44 (shown in FIG. 12) biases the front end 28 away from the rear end 30 along the longitudinal axis L (see FIG. 8) of the latch base 35 and of the prosthetic foot blade 10 to which the latch base 35 is secured. Stated differently, the biasing member (spring 88) biases the ends 38, 30 into the respective pockets 32A, 34A which captures the ends in the catches 32, 34 (see FIG. 7).

The grip 46 may be held such as by the wearer of the prosthetic foot blade 10, and pushed toward the front end 28 to apply a compressive force to the biasing member (spring 88), moving the rear end 30 closer to the front end 28 to enable the lip 56 (see FIGS. 7 and 10) to clear the rear catch 34 and move into the pocket 34A during latching, and, during unlatching, to move out of the pocket 34A. To unlatch, the rear end 30 of the lever 16A may then be pivoted forwardly about the front end 28 in a direction opposite to arrow A1. When sufficiently pivoted, a pulling force of the strap 18 on the lever 16A between the front and rear ends 28, 30 helps to move the front end 28, e.g., rearward, and out of the pocket 32A, allowing the front lip 54 (see FIG. 7) to clear of the front catch 32 to unlatch the lever 16A.

Figure 8:
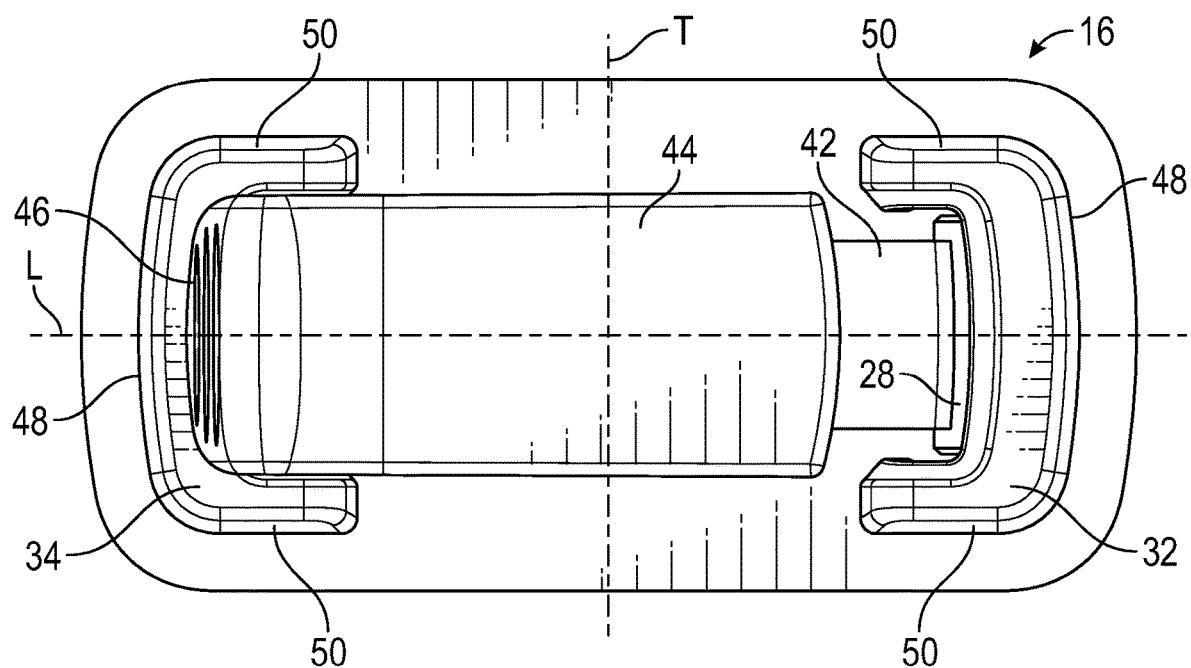
FIG. 8 is a plan view of the latch assembly.

FIG. 8 is a plan view of the latch assembly 16 and best shows that the latch assembly 16 particularly is symmetrical about its longitudinal axis L. The latch base 35 and catches 32, 34 fixed thereon particularly are symmetrical about one or both of the longitudinal axis L and a transverse axis T perpendicular to the longitudinal axis L (shown symmetrical about both the longitudinal axis L and the transverse axis T).

With reference to FIG. 13, the front catch 32 defines the front pocket 32A which opens toward the rear catch 34, and the rear catch 34 defines the rear pocket 34A which opens toward the front catch 32. Each of the front catch 32 and the rear catch 34 particularly are three-sided, with a transverse wall 48, two side walls 50, and a partial hood 52 that together form the pocket 32A or 34A. The side walls 50 of the front catch 32 particularly extend away from the transverse wall 48 toward the rear catch 34 so that the front pocket 32A opens toward the rear pocket 34A. The side walls 50 of the rear catch 34 similarly extend away from the transverse wall 48 of the rear catch 34 toward the front catch 32.

Figure 9:
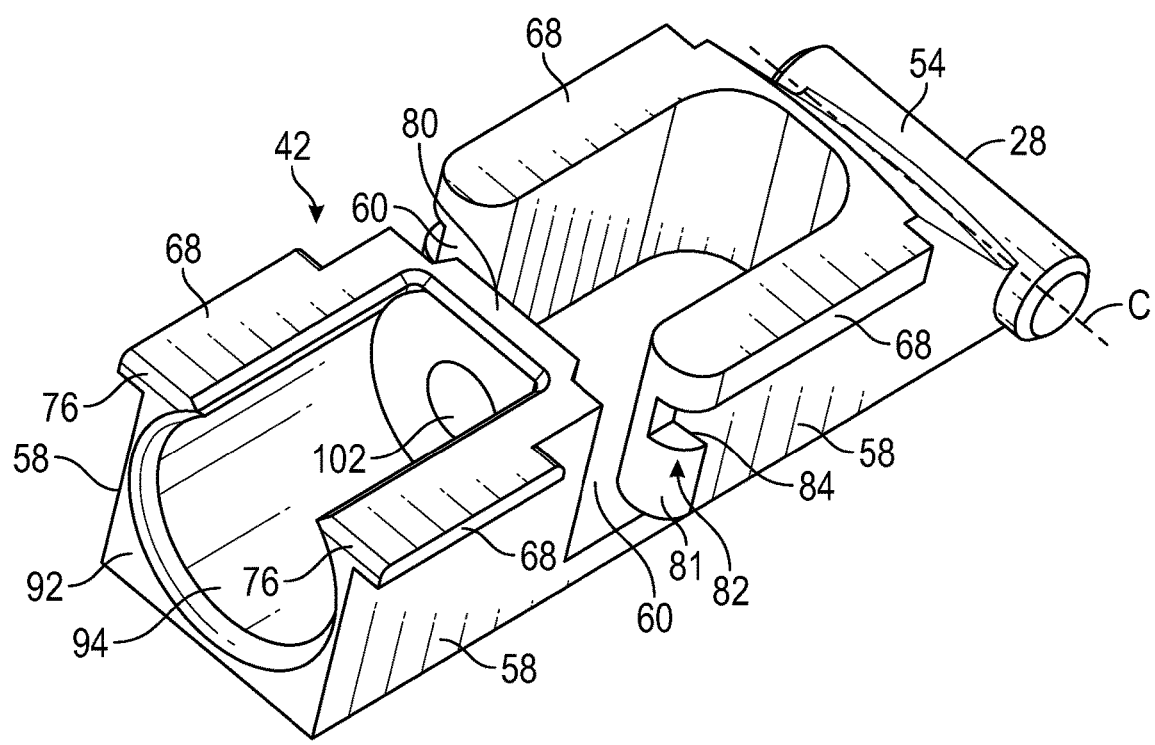
FIG. 9 is a rear perspective view of a first latch body of the latch assembly.

As best shown in FIG. 9, the front end 28 of the first latch body 42 includes a first lip (particularly front lip 54, and referred to herein as such) that is shaped and sized to be captured in the front pocket 32A of FIG. 13 so that the front end 28 latches to the front catch 32. Similarly, the rear end 30 of the second latch body 44 (also referred to as the latch cover) includes a second lip (particularly rear lip 56, and referred to herein as such) (see FIG. 10) that is shaped and sized to be captured in the rear pocket 34A of FIG. 13 so that the rear end 30 latches to the rear catch 34. The front lip 54 has a cylindrical shape to function as a pivot pin, with a center axis C that serves as the pivot axis of the lever 16A during latching and unlatching.

Figure 10:
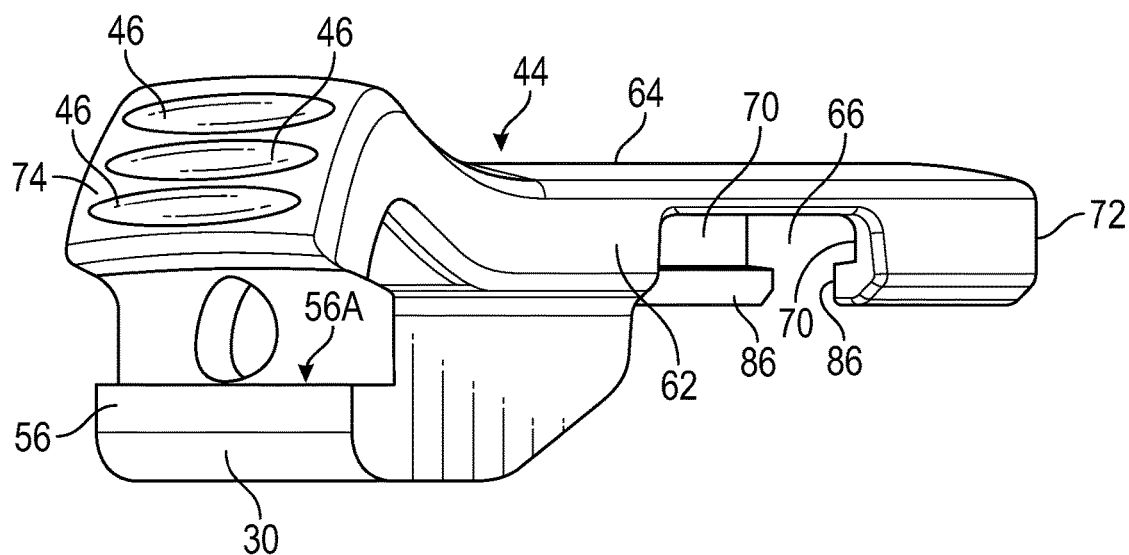
FIG. 10 is a rear perspective view of a second latch body of the latch assembly of FIG. 4, referred to as a latch cover.

As shown in FIG. 10, the rear lip 56 particularly has a flat upper surface 56A that forms a ledge that abuts the inner side of the hood 52 of the rear catch 34 shown in FIG. 13. The flat upper surface 56A particularly maximizes contact area between the rear lip 56 and the rear catch 34 to distribute forces and maintain the latched state.

Referring again to FIG. 9, the first latch body 42 has opposing side walls 58, each having an aperture 60 displaced from (e.g., disposed rearward of) the front end 28 and between the front end 28 and the rear end 30 of the assembled lever 16A (shown in FIG. 7). An intermediate wall 80 extends transversely between the side walls 58 rearward of the aperture 60. When the strap 18 is secured to the sole plate 14 and the lever 16A, the strap 18 extends through the lever 16A at the apertures 60 of the side walls 58 as shown, for example, in FIGS. 3 and 12. By configuring the lever 16A so that the strap 18 particularly applies force to the lever 16A approximately midway between the ends 28, 30, rather than at the rear end 30, the lever arm between the pivot axis at the front end 28 and the pulling force of the strap 18 is shorter, requiring less torque to manipulate the lever 16A during latching. Additionally, the proximity of the strap 18 to the front end 28 helps apply a forward and downward force of the strap 18 to wedge the front end 28 forward into the front catch 32 better than would a latch assembly example in which the strap attaches to the latch assembly nearer to the rear end and/or further above the prosthetic foot blade 10 in a latched position.

Figure 11:
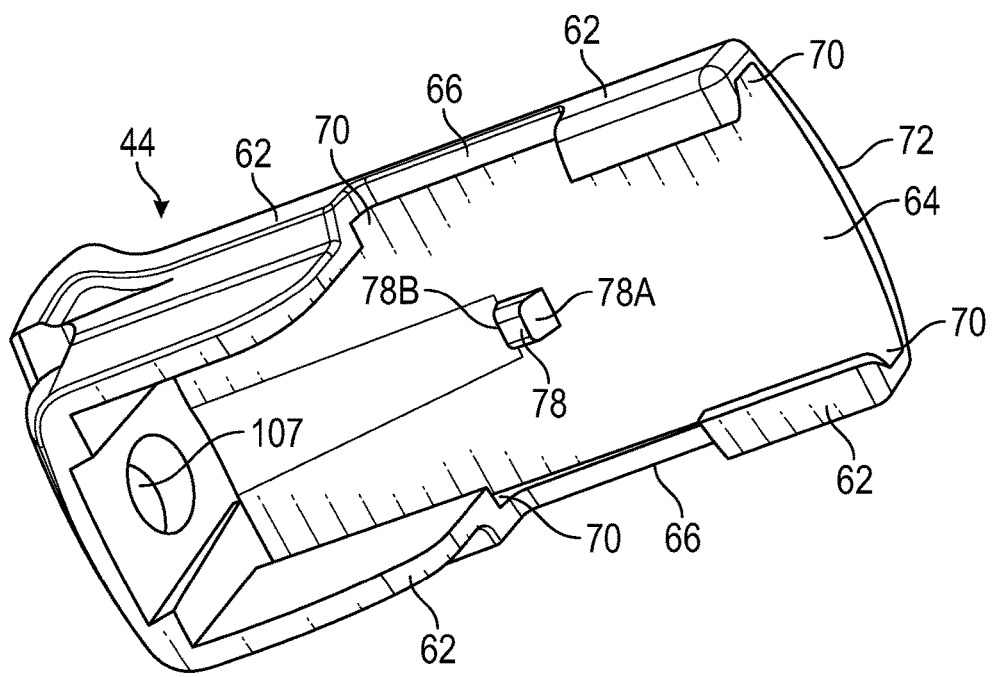
FIG. 11 is a bottom perspective view of the latch cover.

FIGS. 10 and 11 show that the second latch body 44 includes partial side walls 62 extending downward from a top wall 64. The side walls 62 have one or more notches 66 that align with the one or more apertures 60 in the side walls 58 of the first latch body 42 when the latch bodies 42, 44 are coupled to one another. This particularly allows the strap 18 to extend through the apertures 60 without interference from the second latch body 44. The side walls 62 are spaced slightly further apart from one another than are the side walls 58 so that the side walls 62 are disposed adjacent to and outward of the side walls 58 in the assembled lever 16A.

The side walls 58 of the first latch body 42 particularly include outwardly extending flanges 68 near an upper extent of the first latch body 42. The side walls 62 of the second latch body 44 form longitudinal slots 70 (e.g., open channels) at their inner sides. The slots 70 open at a forward edge 72 of the second latch body 44, and are closed by a rear wall 74 of the second latch body 44 near the rear end 30. The flanges 68 at least partly fit within the slots 70.

When the second latch body 44 is secured to the first latch body 42 during assembly of the lever 16A, the forward edge 72 is positioned at the rear end 76 of the flanges 68, and the second latch body 44 is slid forward along the flanges 68 at least until a protrusion 78 on the bottom side of the top wall 64 (see FIG. 11) passes over an intermediate wall 80 of the first latch body 42.

The intermediate wall 80 is disposed rearward of the front end 28 and forward of the rear end 30. The protrusion 78 particularly has an angled forward surface 78A that allows it to pass over the intermediate wall 80 during assembly, but an orthogonal back surface 78B of the protrusion 78 prevents backward travel of the protrusion 78 over the intermediate wall 80.

The side walls 58 particularly have a protrusion 81 (best seen in FIG. 7) with a rounded surface 82 where the strap 18 interfaces with and pulls forward against the lever 16A to strengthen the side walls and avoid sharp corners at the interface with the strap 18. Additionally, each side wall 58 particularly defines a notch 84 between the flange 68 and the protrusion 81 through which a lower inner rim 86 of the side walls 62 of the second latch body 44 (see FIG. 10) passes during assembly of the second latch body 44 to the first latch body 42.

Figure 12:
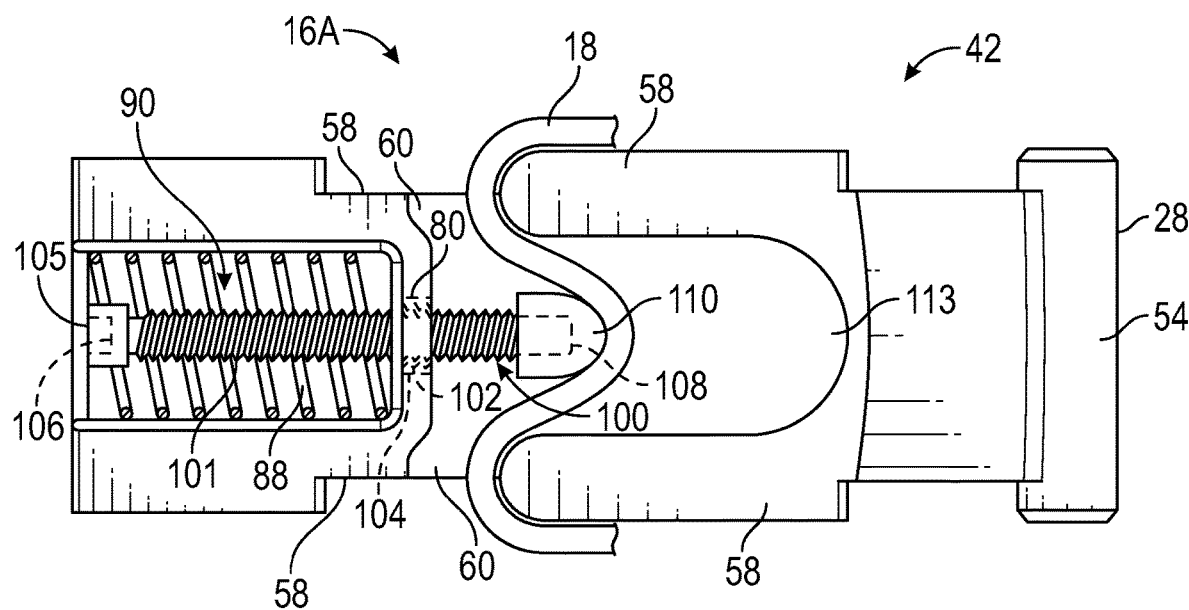
FIG. 12 is a plan view of the first latch body, showing a biasing member in cross-sectional view, and a tension adjustment device for the strap.

FIG. 12 is a plan view of the first latch body 42 with the strap 18 extending through the side walls 58 at the apertures 60. A biasing member 88 is shown that biases the front end 28 away from the rear end 30 in the assembled lever 16A. The biasing member 88 particularly is shown and referred to as a compression spring 88 and, more particularly, as a compression-type coil spring. It should be understood that other biasing member(s) may instead or in addition be used such as a resilient rod, spring member, or the like. The coil spring 88 is disposed in a chamber 90 of the first latch body 42 formed between the side walls 58 and rearward of the intermediate wall 80.

The chamber 90 is partially cylindrical, with an open top. As best shown in FIG. 9, the rear wall 92 of the first latch body 42 has an opening 94 in the shape of a partial circle. The diameter of the coil spring 88 is smaller than the diameter of the opening 94.

Once inserted in the chamber 90, a rear of the coil spring 88 particularly interfaces with the inner side of the rear wall 74 of the second latch body 44, and a front of the coil spring 88 interfaces with the rear face of the intermediate wall 80 of the first latch body 42. In this manner, the front end 28 of the lever 16A is biased apart from the rear end 30 to help maintain the ends 28, 30 in the respective pockets 32A, 34A in the latched position.

In the latched position, the rear wall 74 of the second latch body 44 is particularly spaced apart from the rear wall 92 of the first latch body 42 by the coil spring 88. The coil spring 88 also forces a forward face of the intermediate wall 80 against the back surface 78B of the protrusion 78 so that the protrusion 78 limits the longitudinal separation of the front end 28 and the rear end 30.

To unlatch the lever 16A from the rear catch 34, a force on the grip 46 toward the front catch 32 (e.g., in the forward direction) opposes the biasing force of the spring 88 against the rear wall 74 and, if of sufficient magnitude, can overcome the biasing force of the spring, compressing the spring 88 and sliding the second latch body 44 along the flanges 68 so that the rear wall 74 is closer to the rear wall 92, shortening the distance between the ends 28, 30 to release the lever 16A from the rear catch 34.

Referring to FIG. 12, the latch assembly 16 particularly includes a tension adjustment device 100 for the strap 18. The tension adjustment device 100 includes an adjustment screw 101 extending longitudinally within the lever 16A and interfacing with the strap 18. The adjustment screw 101 extends longitudinally in the chamber 90 and through a threaded opening 102 in the intermediate wall 80. The intermediate wall 80 itself may be threaded at the opening 102, or an internally threaded ring 104 may be set in the opening 102 as indicated in FIG. 12 (the ring 104 is not shown in FIG. 9).

At least a portion of the adjustment screw 101 has external threads that engage the threaded opening 102. A rear end 105 of the screw 101 has a socket 106 at which the adjustment screw 101 may be engaged, e.g., with a tool to move the screw fore and aft along the longitudinal axis of the lever 16A. As shown in FIG. 11, the second latch body 44 has a rear window 107 through which the socket 106 may be accessed.

A first end of the screw 101 (particularly being a front end 108, and referred to herein as such) is at least partly covered by a plunger tip 110 that contacts the strap 18. By adjusting the screw 101, a midportion of the strap 18 is pushed fore or aft in a forward chamber 113 of the first latch body 42 at the plunger tip 110.

Because ends of the strap 18 particularly are fixed to the sole plate 14 as further discussed herein, moving the midportion of the strap 18 with the adjustment screw 101 adjusts the tension in the strap 18. For example, moving the plunger tip 110 forward into the strap 18 pushes the midportion of the strap 18 forward, increasing tension. Moving the plunger tip 110 rearward allows the midportion of the strap 18 to also move rearward, decreasing tension. The magnitude of the adjustment may be relatively small. For example, the adjustment device 100 may be intended to overcome small variances in tension related to production tolerances in the length of the strap 18, a slight relaxing or deformation of the strap 18 over time effecting its length, variances in placement of the strap 18 on the sole plate 14 during assembly, or other production variances. The strap 18 may be particularly a relatively inelastic material, such as a tightly woven nylon webbing, plastic, a steel cable, or another material or combination of materials.

FIG. 13 is a bottom perspective view of the front and rear catches 32, 34 showing one or more fastener openings 112 sized and spaced to align with one or more fastener openings 114 in the latch base 35 of FIG. 14.

One or more alignment features 116A of the catches 32, 34 align with one or more corresponding alignment features 116B of the latch base 35 shown in FIG. 14 to position the catches 32, 34 prior to extending fasteners through the fastener openings 114 into the fastener openings 112.

FIG. 14 is a perspective view of the bottom surface 120 of the latch base 35 that faces away from the catches 32, 34 when assembled to the latch base 35. As shown in FIG. 14, the one or more fastener openings 114 particularly are beveled. This enables heads of the fasteners, such as screws, used to connect the catches 32, 34 to the latch base 35 to be recessed into the latch base 35, enabling the bottom surface 120 to present as flat at the top side of the prosthetic foot blade 10 when fixed to the top side 23 of the prosthetic foot blade 10, such as by adhesive bonding.

As is evident by the positions of the fastener openings 114 and the footprint of the catches 32, 34, the latch base 35 and its bottom surface 120 extends forward, rearward, and/or outward of the catches 32, 34. This provides a larger bonding surface and spreads forces of the tensioned strap 18 over a greater surface area than if the bottom surface 120 were smaller. For example, a portion 35A of the latch base 35, shown in FIG. 3, extends forward of the front catch 32 along the top side 23 of the prosthetic foot blade 10.

The latch base 35 may be relatively thin and flexible in order to flex with the underlying prosthetic blade 10. For example, the latch base 35 may be a carbon fiber material. Portions of the latch base 35 below the footprint of the catches 32, 34 and the lever 16A are substantially prevented from flexing during use due to the overlying structure. Because the prosthetic foot blade 10 flexes and changes in curvature during use, the portions of the latch base 35 that extend forward, rearward, and/or outward of the catches 32, 34, such as the forward portion 35A, that have no overlying structure can bend in conformity with the bending of the prosthetic foot blade 10 to better ensure the bonded bottom surface 120 will not separate from the prosthetic foot blade 10. By attaching the fasteners to the compliant latch base 35, components of the latch assembly 16 are able to move with the flexing foot blade 10 and vibrations in the latch assembly 16 are minimized.

Figure 15:
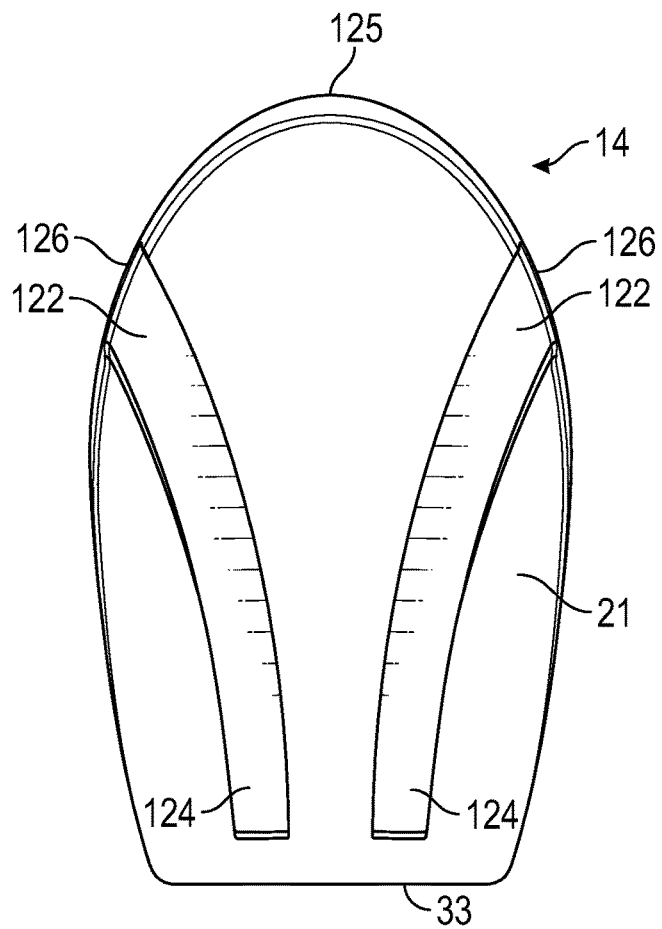
FIG. 15 is a bottom perspective view of the sole plate.

FIG. 15 is a bottom perspective view of the sole plate 14 showing recesses 122 formed or otherwise provided in the bottom side 21. The recesses 122 are of a depth and length to receive portions of the strap 18. More specifically, the strap 18 is adhered to the sole plate 14 in the recesses 122. Forward ends 124 of the recesses 122 are closer to the front wall 33 of the sole plate 14 than to a rear wall 125. The recesses 122 extend rearward and outward to side exits 126 at opposite sides of the sole plate 14 near the rear wall 125.

Figure 16:
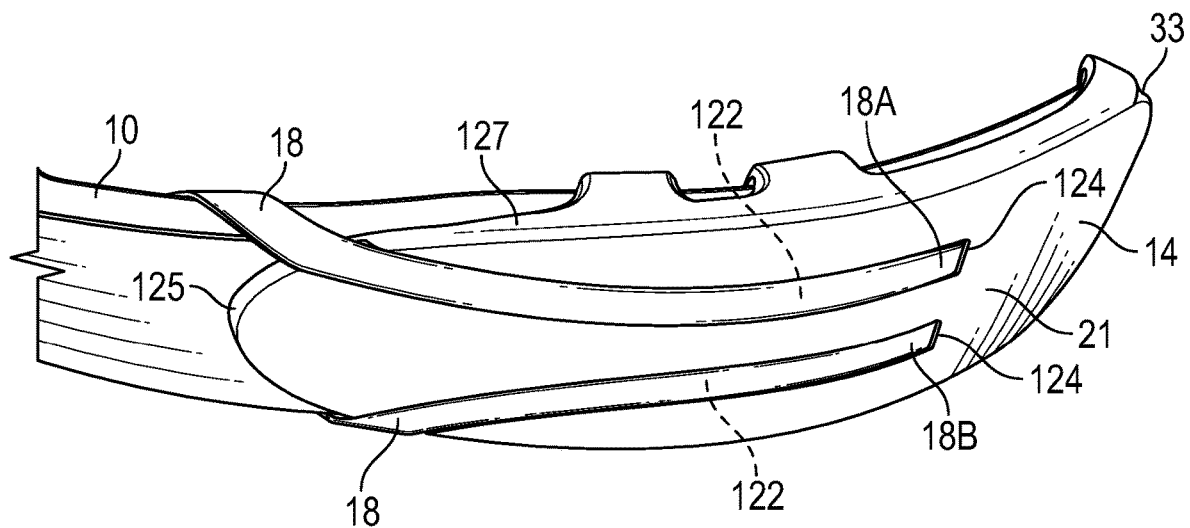
FIG. 16 is a bottom perspective view of the sole plate secured to the prosthetic foot blade shown in fragmentary view.

As shown in FIGS. 1 and 16, side walls 127 of the sole plate 14 reduce in height (e.g., taper) in the rearward direction until they end at the exits 126 as shown in FIG. 16. The side walls 127 increase in height in a forward direction from the exits 126 of the strap 18 toward the toe cap 36. The side walls 127 act as side barriers extending up outward of the sole plate 14 to help center the prosthetic foot blade 10 over the sole plate 14. The sole plate 14 shown is symmetrical about the longitudinal axis (e.g., an axis extending through the center of its front wall 33 to a center of the rear wall 125. Accordingly, the side wall 127 shown is identical to a side wall on the other side of the sole plate 14. With the front wall 33 and opposing side walls 127, the sole plate 14 functions as a three-sided tray.

As shown in FIG. 16, ends 18A, 18B of the strap 18 are disposed at the ends 124 of the recesses 122. A single strap 18 is used in FIGS. 1, 2, 12 and 15-16, with a midportion 18C of the strap 18 extending through the lever 16A in FIG. 2. Alternatively the strap 18 could be a loop, and the recess 122 could be continuous (e.g., without ends) at the bottom side 21 to accommodate the front of the loop. In yet another example, two straps could be used, each extending from its respective end 18A, 18B to a separate end that is secured to the lever 16A after extending into the lever through the respective aperture 60.

Figure 17:
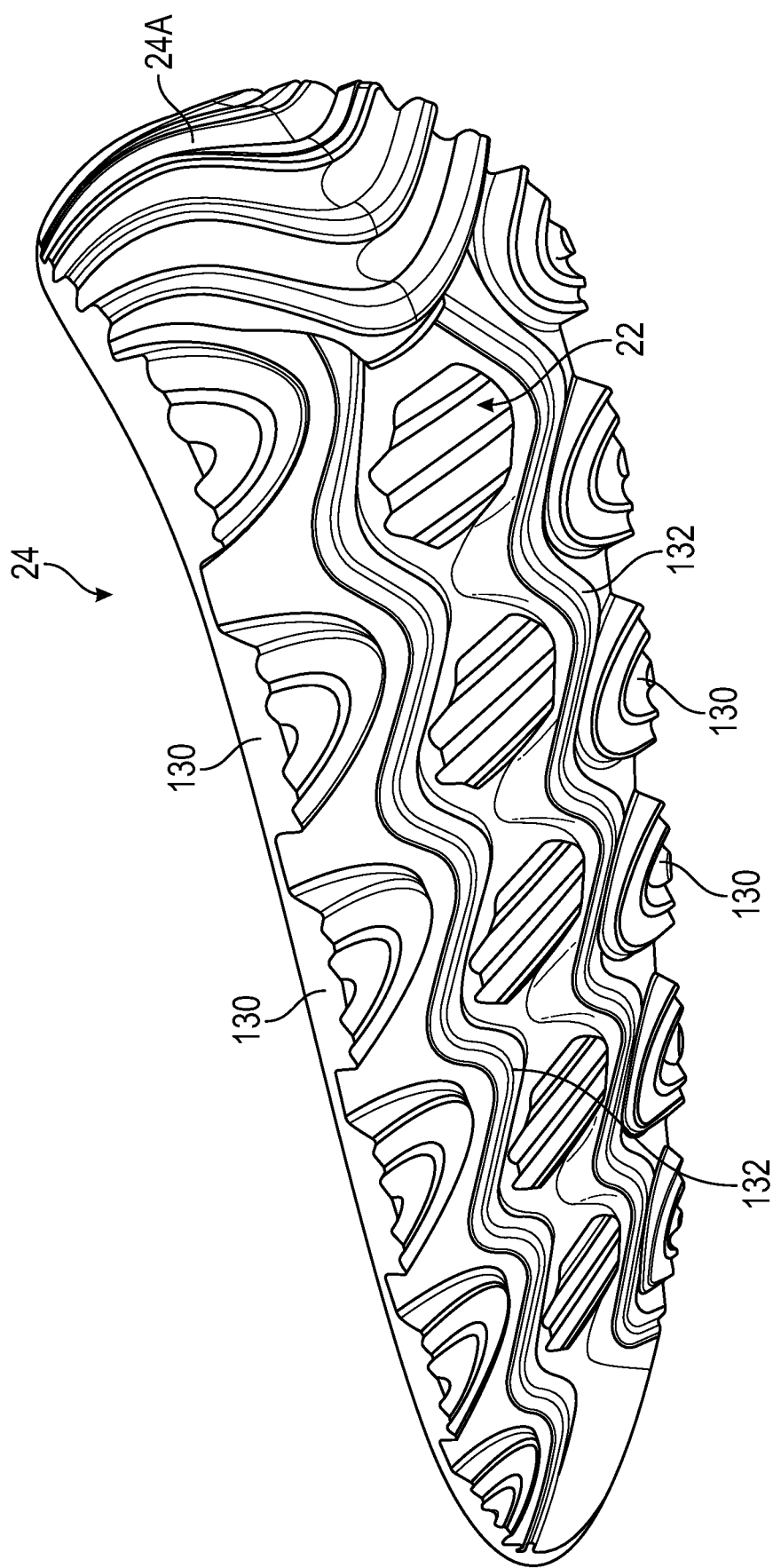
FIG. 17 is a bottom perspective of an outsole of the traction system of FIG. 1.

FIG. 17 is a bottom perspective of the outsole 24 of FIG. 1. The outsole 24 may be natural or artificial rubber or another flexible and durable material capable of providing traction. The outsole 24 particularly has a variety of protrusions 130 and channels 132 arranged in a pattern as shown to increase traction and durability of the traction system of FIG. 1. A forward portion 24A of the outsole 24 is shaped to extend over the front wall 33 of the sole plate 14.

When the midsole 26 (see FIG. 1) and the outsole 24 are secured at the bottom side 21 of the sole plate 14, the recesses 122 are covered and the portions of the strap 18 in the recesses 122 are sandwiched between the midsole 26 and the bottom side 21 of the sole plate 14, or, in examples without a midsole 26, between the outsole 24 and the bottom side 21 of the sole plate 14.

Figure 18:
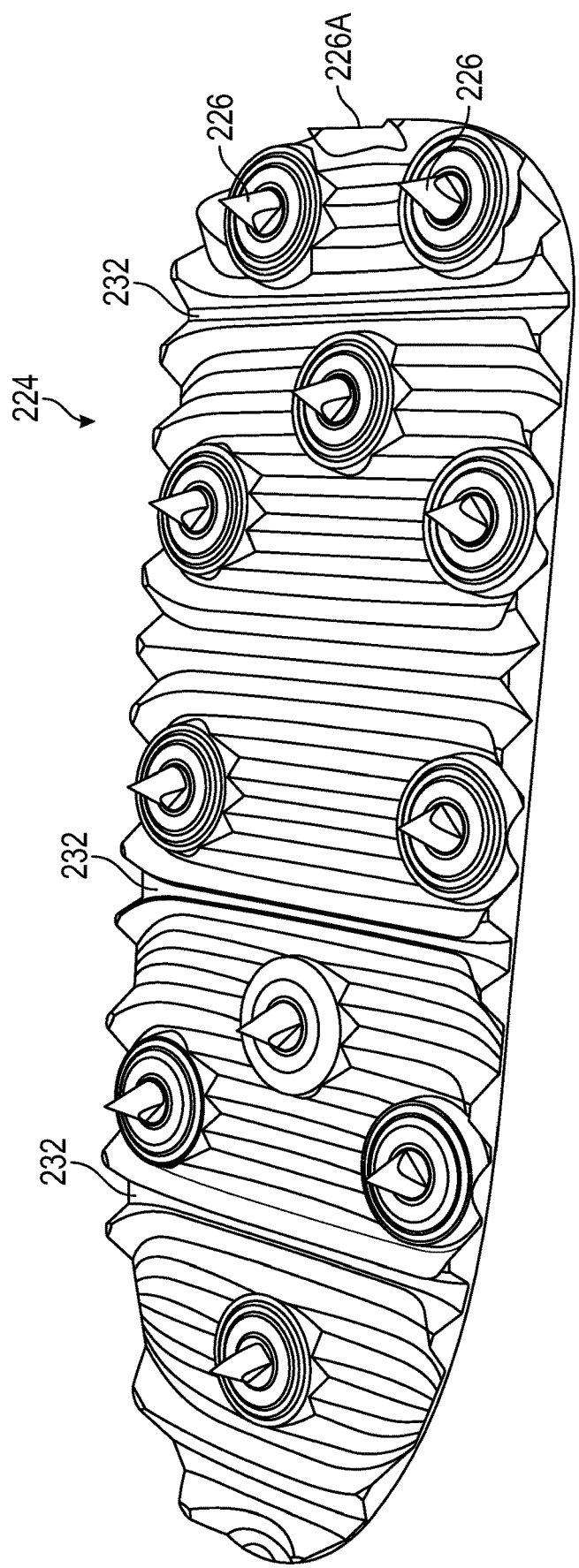
FIG. 18 is a bottom perspective view of a spike plate and spikes as an alternative to the outsole for the traction system of FIG. 1.

FIG. 18 is a bottom perspective view of a spike plate 224 with one or more spikes 226. Specifically, two or more of the spikes 226 are located at or near the forward extent 226A of the spike plate 224 and act to enhance traction during toe-off. One or more of the spikes 226 may be integrally formed with the plate, while another one or other ones of the spikes 226 may be fastenable to the spike plate 224. Alternatively, in some examples, all of the spikes 226 are integrally formed with the spike plate 224, or all of the spikes 226 are fastenable to the spike plate 224. The spike plate 224 may be secured directly to the bottom side 21 of the sole plate 14 or, in some examples, a sole layer, such as a cushioning midsole, may be disposed between the sole plate 14 and the spike plate 224. In still other examples, the spike plate 224 may be integrally formed as the bottom of the sole plate 14. The spike plate 224 particularly may be plastic, and/or may include one or more transversely-extending channels 232 that enable the spike plate 224 to bend with the prosthetic foot blade 10 during flexing of the prosthetic foot blade 10.

Figure 19:
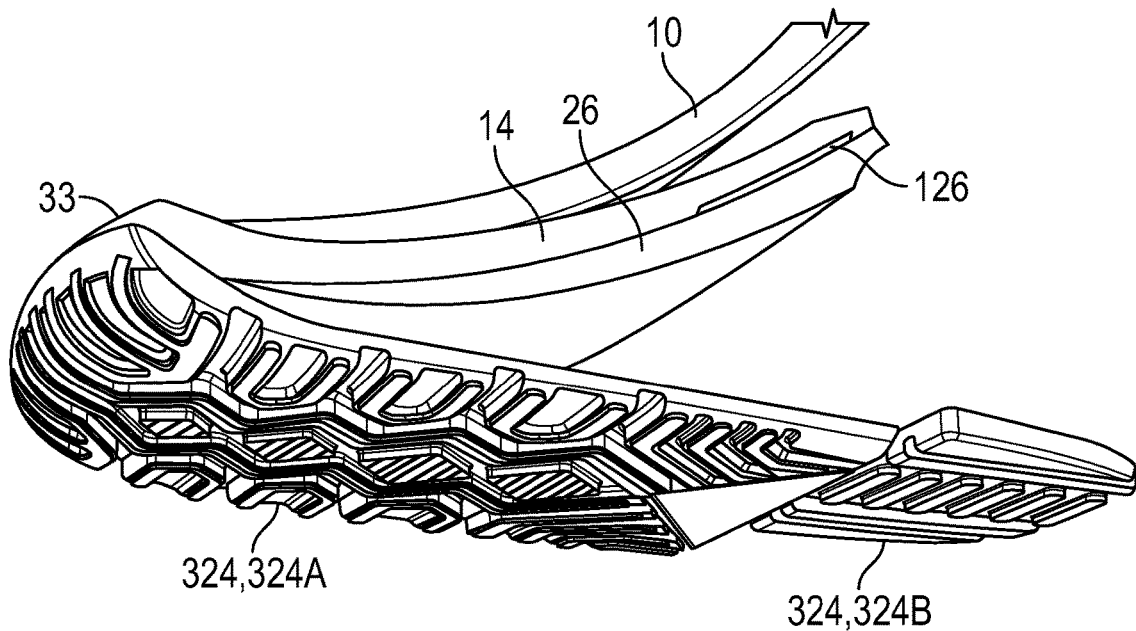
FIG. 19 is a fragmentary, partially exploded view of the prosthetic foot blade and sole structure of the traction system of FIG. 1 with an alternative outsole.

FIG. 19 is a fragmentary, partially exploded view of the prosthetic foot blade 10 and the sole plate 14 and midsole 26 of the sole structure 20 of FIG. 1 with an alternative outsole 324. The outsole 324 includes a first (front) outsole portion 324A, and separate second (rear) outsole portion 324B, both of which particularly may be a flexible and durable material, such as natural or artificial rubber. The front outsole portion 324A is particularly secured to a bottom surface of the midsole 26 and extends on and forward of the front wall 33 of the sole plate 14. The rear outsole portion 324B may be secured directly to the bottom side 27 of the prosthetic foot blade 10 so that it is disposed just rearward of the front outsole portion 324A when the traction assembly (particularly including the sole plate 14, midsole 26, front outsole portion 324A, and a strap 18 and latch assembly 16 or other latch assembly) is coupled to the prosthetic foot blade 10. Alternatively, the midsole 26 and sole plate 14 may be long enough that both the rear outsole portion 324B may be secured to the bottom surface of the midsole 26 just rearward of the front outsole portion 324A.

Figure 20:
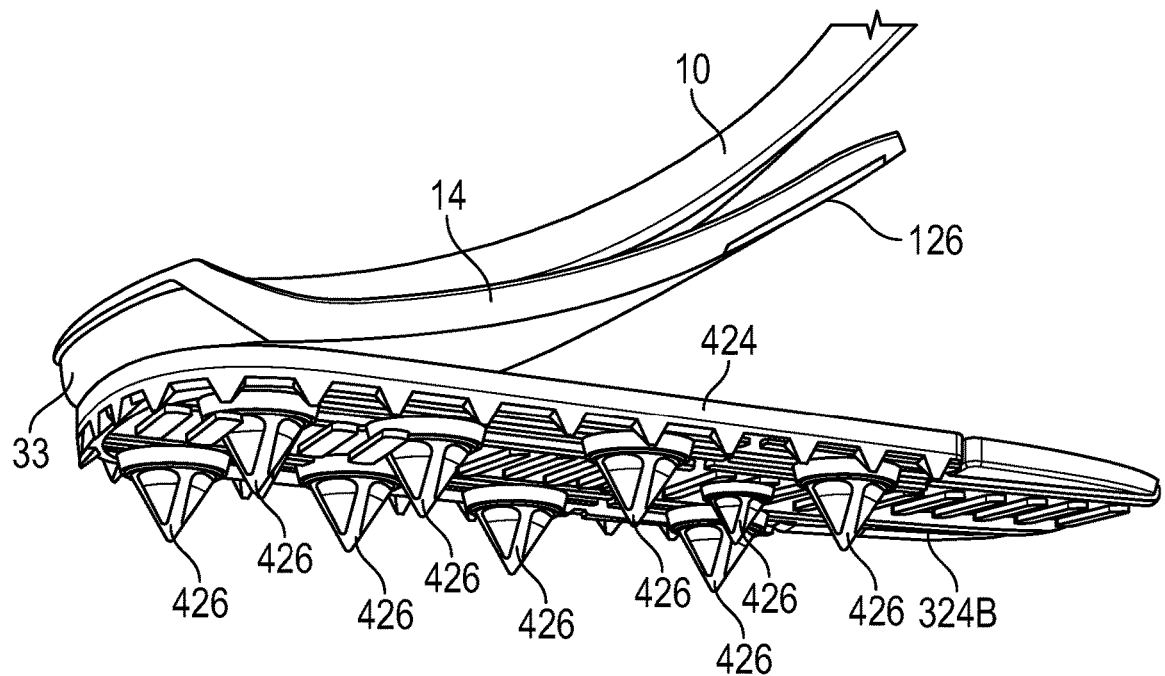
FIG. 20 is a fragmentary, partially exploded view of the prosthetic foot blade and sole structure of the traction system of FIG. 1 with a spike plate and spikes as an alternative to the midsole and outsole of FIG. 1.

FIG. 20 is a fragmentary, partially exploded view of the prosthetic foot blade 10 and the sole plate 14 of the sole structure 20 of FIG. 1 with a spike plate 424 and spikes 426 as an alternative to the midsole and outsole of FIG. 1. In comparison to FIG. 19, the spike plate 424 is used in lieu of the front outsole portion 324A, but the same or similar rear outsole portion 324B may be used. One or more of the spikes 426 may be fastenable to the spike plate 424 while another one or other ones od the spikes 426 may be integrally formed with the spike plate 424. The spike plate 424 is secured to a bottom surface of the midsole 26.

The spike plate 424 particularly may be less flexible than the front outsole portion 324A, and so may not extend upward along the front wall 33. The rear outsole portion 324B may be secured directly to the bottom side 27 of the prosthetic foot blade 10 so that it is disposed just rearward of the spike plate 424 when the traction assembly (particularly including the sole plate 14, spike plate 424, and/or a strap 18 and latch assembly 16 or other latch assembly) is coupled to the prosthetic foot blade 10. Alternatively, the sole plate 14 may be long enough that the rear outsole portion 324B may be secured to the bottom surface of the sole plate 14 just rearward of the spike plate 424.

Figure 21:
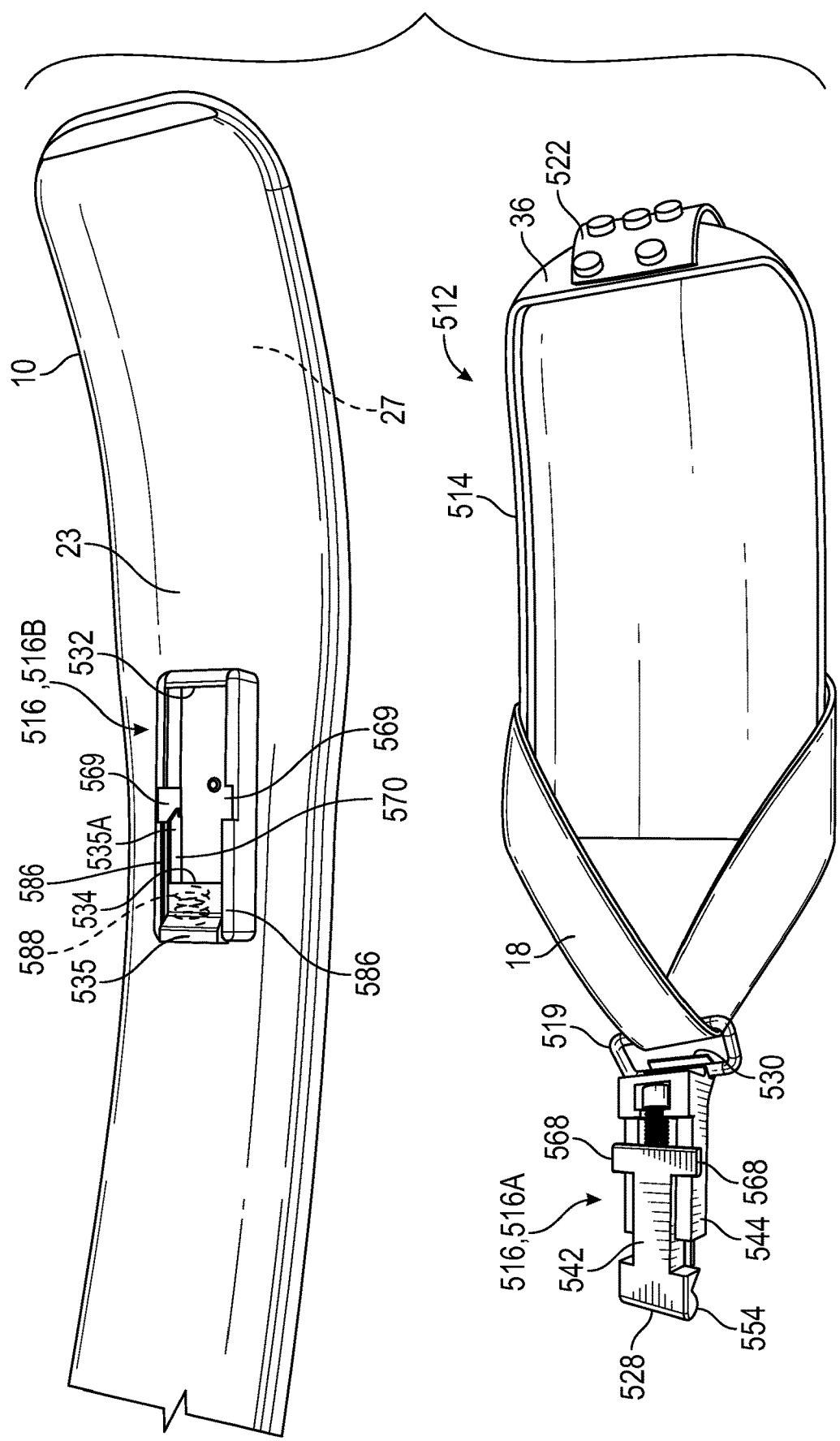
FIG. 21 is a fragmentary perspective exploded view of a prosthetic foot blade and an alternative traction system for the prosthetic foot blade, including a sole plate, a strap, and a latch assembly, with the latch assembly in an unlatched state.

FIG. 21 is a fragmentary perspective exploded view of the prosthetic foot blade 10 and an alternative traction system 512 for the prosthetic foot blade 10. The traction system 512 includes a sole plate 514, an outsole 522, the strap 18, and/or a latch assembly 516. The sole plate 514 is similar to the sole plate 14 and configured to couple to the distal end 38 of the prosthetic foot blade 10 to substantially extend under the bottom side 27, having a front wall 33 forward of the distal end 38, and a toe cap 36 extending from the front wall 33 rearward over the distal end 38.

The sole plate 514 particularly also has one or more recesses 122 as shown with respect to sole plate 14 in FIG. 15, and a strap 18 secured to the sole plate 514 in the recesses 122 and sandwiched between the sole plate 514 and one of more sole layers extending under a bottom side of the sole plate 514. For example, the traction system 512 includes the outsole 522 (only a portion of which is shown) that extends under the sole plate 514, establishing a ground-engaging surface.

Figure 24:
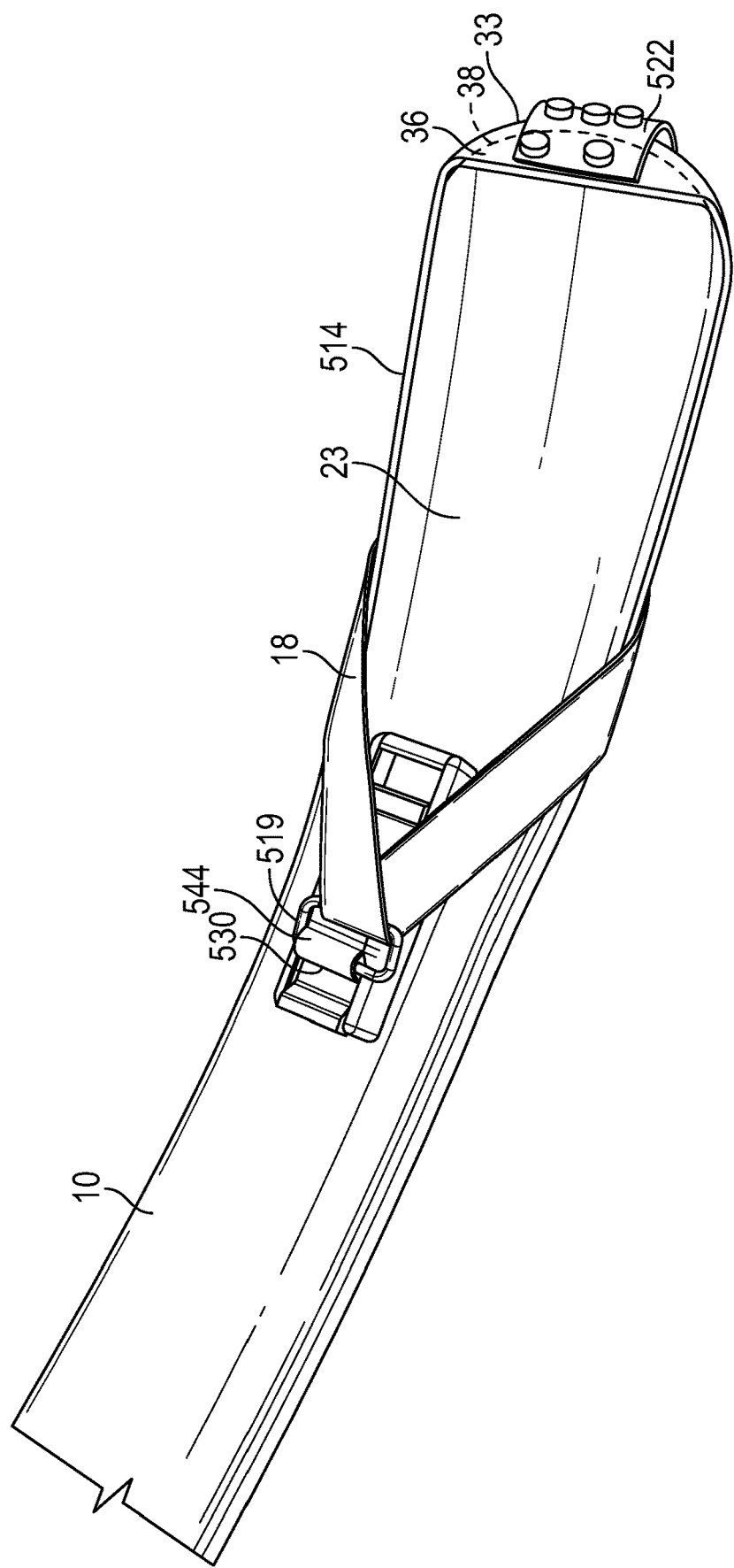
FIG. 24 is a perspective view of the traction system FIG. 21 coupled to the prosthetic foot blade shown in fragmentary view, with the latch assembly in a latched state.

The latch assembly 516 is shown in an unlatched state in FIG. 21, and is configured as an over-center draw latch. The latch assembly 516 has at least one lever 516A shown detached from the prosthetic foot blade 10 in FIG. 21, and at least one latch mount 516B secured to the top side 23 of the prosthetic foot blade 10 even when the traction system 512 is detached with the latch assembly 516 in the unlatched state. The strap 18 particularly is placed in tension as discussed herein when the sole plate 514 is fitted to the prosthetic foot blade 10 and the latch assembly 516 is latched to couple the sole plate 514 to the prosthetic foot blade 10, as shown in FIG. 24.

Figure 22:
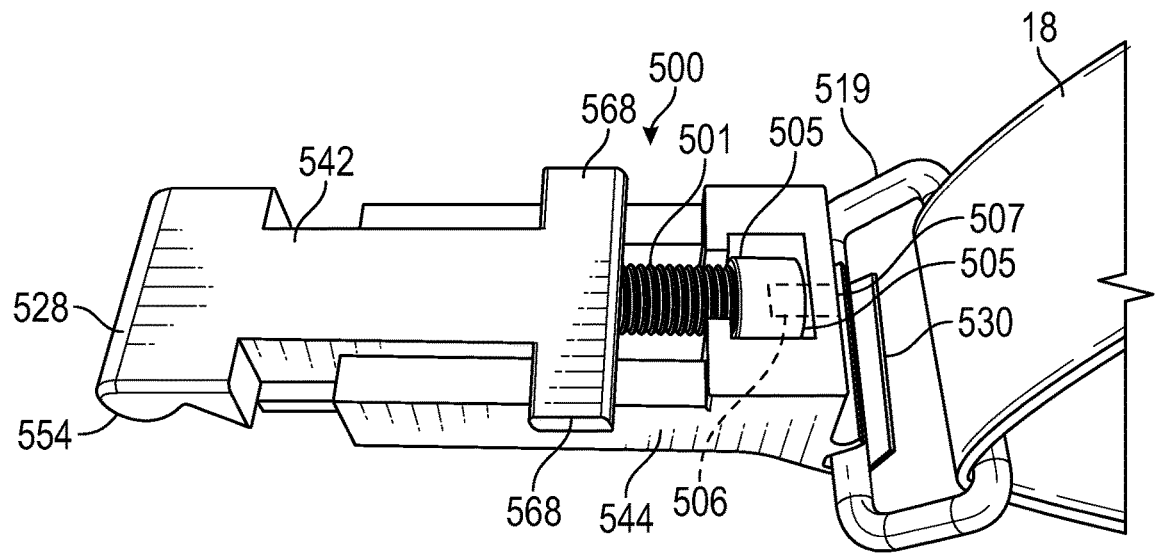
FIG. 22 is a perspective view of a lever of the latch assembly of FIG. 21, a connecting ring, and the strap shown in fragmentary view.
Figure 23:
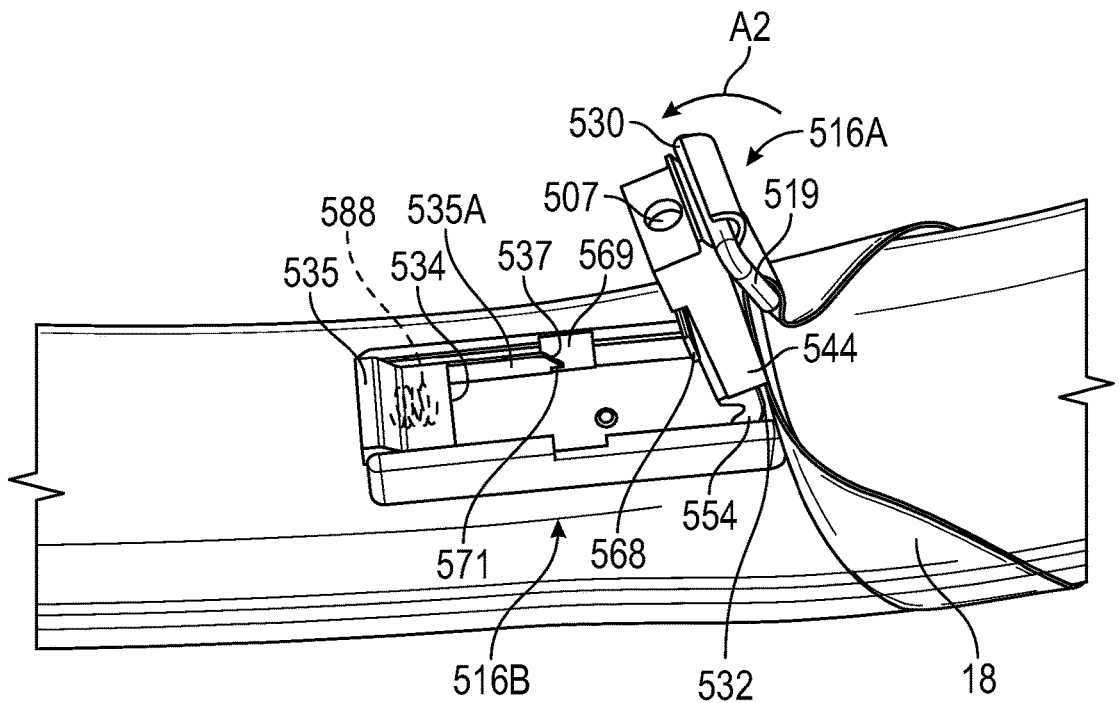
FIG. 23 is a fragmentary perspective view of the traction system of FIG. 21 coupled to the prosthetic foot blade, with the latch assembly in a partially latched state.

A first latch body 542 includes a first (front) end 528 of the lever 516A that is captured under and retained to front catch 532 of the latch mount 516B in the latched state. A second latch body 544 includes a second (rear) end 530 of the lever 516A. In FIGS. 21 and 22, a bottom side of the lever 516A is shown, and the lever is reversed from that position when latched, with the front end 528 disposed at the front catch 532 as shown in FIG. 23 and a rear end 530 near a front wall 534 of a spring-biased button 535. The lever 516A is then pivoted rearward about a front lip 554 in the direction of arrow A2.

One or more flanges 568 of the first latch body 542 fit through one or more notches 569 in the second latch body 544 and then interface with ramped surfaces 537 (see FIG. 23) of arms 535A of the spring-biased button 535. One arm 535A is shown in FIG. 21 extending under the notch 569, and a like arm is disposed on the substantially opposite side of the button 535 extending toward the other notch 569. The arms 535A are retained in channels 570 under a top rim 586 of the second latch mount 516B.

Under the force of the flanges 568 against the ramped surfaces 537, the arms 535A particularly slide rearward slightly with the button 535 against the biasing force of a biasing member (such as a spring 588) disposed in a channel in the button 535. The spring 588 biases the button 535 away from a rear end wall of the latch mount 516B. The flanges 568 particularly are then trapped under notches 571 (see FIG. 23) at the ends of the arms 535A when the lever 516A is completely pivoted and a manual force inserting the lever 516A is released. In this position, the strap 18 is tensioned as it is secured to the lever 516A via a ring 519 engaged with the second end 530.

To unlatch the latch assembly 516 in order to remove the traction system 512 from the prosthetic foot blade 10, the button 535 is pressed rearward against the force of the spring 588, causing the arms 535A to move rearward and the flanges 568 to no longer be disposed within the notches 571. The lever 516A can then be lifted at its rear end 530 and pivoted in a direction opposite A2 in FIG. 23, with the flanges 568 moving out through the notches 569. The front end 528 can then be slid out from (i.e., released from) the front catch 532.

The latch assembly 516 particularly also includes a tension adjustment device 500 (see FIG. 22) that adjusts tension in the strap 18 when the latch assembly 516 is latched. Unlike the traction system 12, the strap 18 does not extend through the latch bodies 542, 544, but instead extends through the ring 519 captured by the first latch body 542 near the rear end 530.

The tension adjustment device 500 particularly includes a threaded adjustment screw 501 substantially extending longitudinally within the lever 516A. Unlike adjustment screw 101 of FIG. 12, the adjustment screw 501 does not interface with the strap 18, but instead interfaces with an internal transverse wall of the first latch body 542 to adjust an overall distance between the front end 528 and the rear end 530 in the latched position. Because the strap 18 is connected to the first latch body 542 via the ring 519, tension in the strap 18 is increased or decreased via the tension adjustment device 500.

An end (rear end) 505 of the screw 501 particularly has a socket 506 at which the adjustment screw 501 may be engaged with a tool to move the screw fore and aft along the longitudinal axis of the lever 516A. As shown in FIGS. 22 and 23, the second latch body 544 has a window (rear window 507) through which the socket 506 may be accessed.

Figure 25:
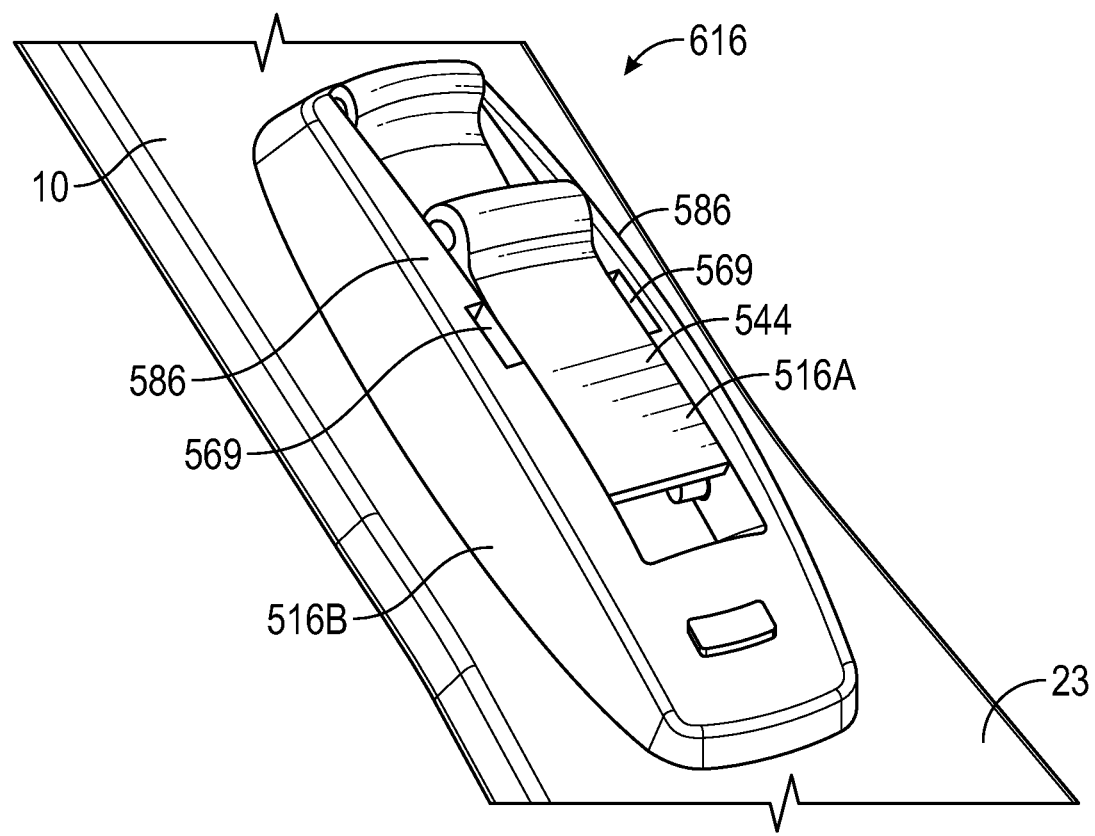
FIG. 25 is a perspective view of an alternative latch assembly for a traction system secured on a prosthetic foot blade shown in fragmentary view.

FIG. 25 is a perspective view of an alternative latch assembly 616 for a traction system and is shown latched to the top side 23 of the prosthetic foot blade 10, with the ring 519, strap 18, and sole plate 14 or 514 not shown. The latch assembly 616 functions as described with respect to latch assembly 516, and has slightly different styling of the outer walls of the latch mount 516B.

Figure 26:
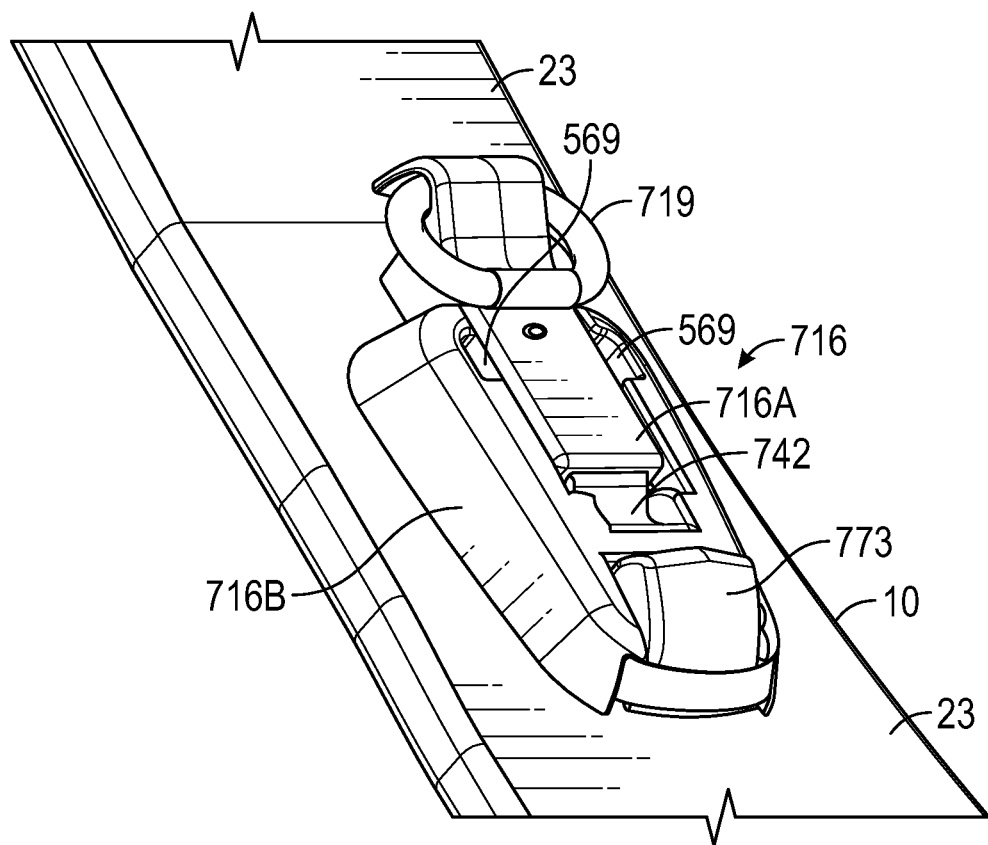
FIG. 26 is a perspective view of an alternative latch assembly for a traction system secured on a prosthetic foot blade shown in fragmentary view.

FIG. 26 is a perspective view of another alternative latch assembly 716 for a traction system and is shown latched to the top side 23 of the prosthetic foot blade 10, with a ring 719 for the strap 18, similar to ring 519, and/or with the strap 18 and the sole plate 14 or 514 not shown. The latch assembly 716 functions as described with respect to latch assembly 516, but with the notches 569 further toward the rear of the latch mount 716B, and/or with a release button 773 that overcomes a biasing member (such as a biasing spring) to release the flanges 568 from under arms of the button, enabling the flanges 568 to be pivoted through the notches 569, allowing unlatching of the lever 716A. The flanges 568 are not visible in FIG. 26 but extend from a first latch body 742 that includes the front end, similar to lever 516A.

Figure 27:
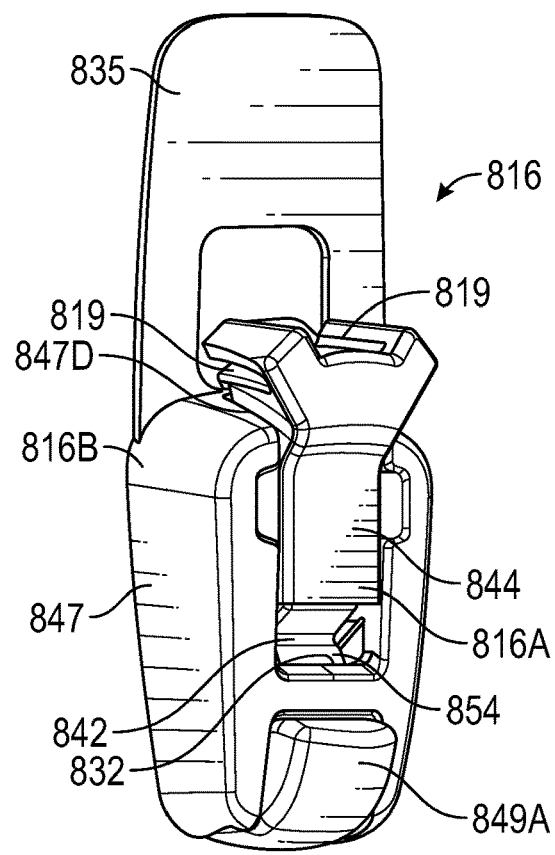
FIG. 27 is a perspective view of an alternative latch assembly for a prosthetic foot blade traction system.

FIG. 27 is a perspective view of an alternative latch assembly 816 for a prosthetic foot blade traction system. The latch assembly 816 is shown in a latched state in FIG. 27, and is configured as an over-center draw latch. The latch assembly 816 particularly has at least one lever 816A and at least one latch mount 816B to which the lever 816A is latchable. The latch mount 816B includes a latch base 835 and a mount body 847 fixable to the latch base 835, and the latch base 835 is securable to the top side 23 of the prosthetic foot blade 10 shown in FIG. 1 even when the traction system is detached with the latch assembly 816 in the unlatched state.

Figure 28:
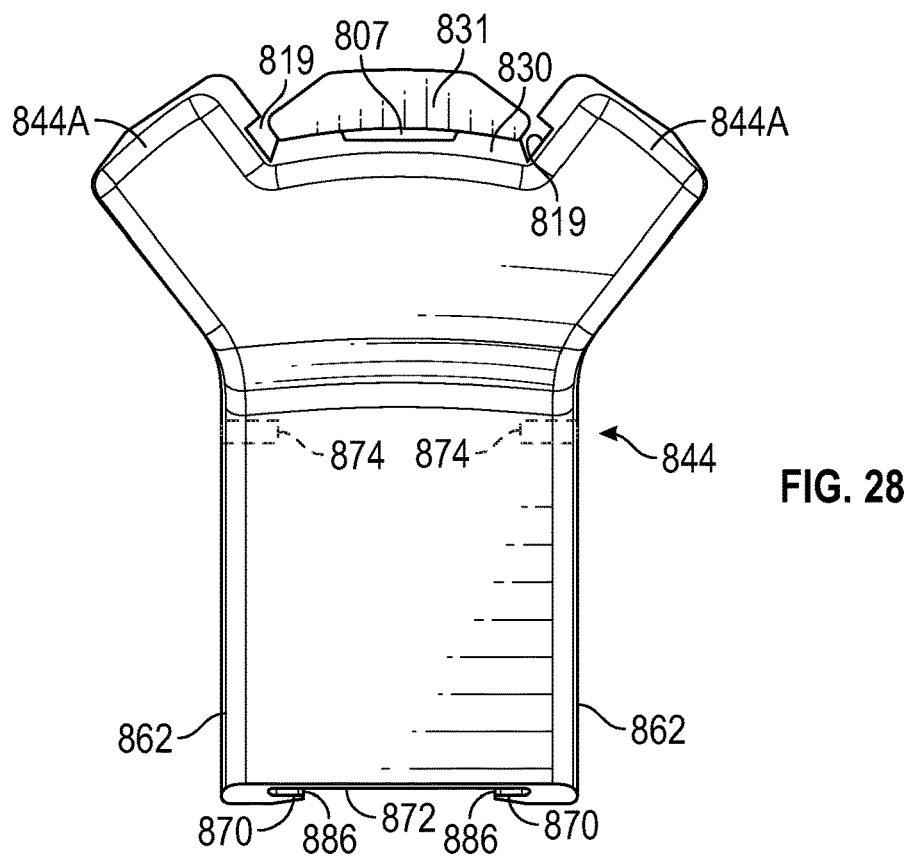
FIG. 28 is a plan view of a second latch body of a lever of the latch assembly of FIG. 27.

The lever 816A includes a first latch body 842 (best shown in FIG. 29) and a second latch body 844 (best shown in FIG. 28). The first latch body 842 includes a front lip 854 at a front end 828 configured to function in the same manner as lip 554 of the lever 516A. The first latch body 842 also includes spaced side walls 858 that have outwardly extending flanges 868 near an upper extent of the first latch body 842. The second latch body 844 has spaced side walls 862 that form longitudinal slots 870 (e.g., open channels) at their inner sides. The slots 870 open at a forward edge 872 of the second latch body 844, and are closed by an intermediate wall 874 extending inward from the side walls 862 between the forward edge 872 and a rear end 830 of the second latch body 844. The flanges 868 of the first latch body 842 particularly fit within the slots 870.

Figure 29:
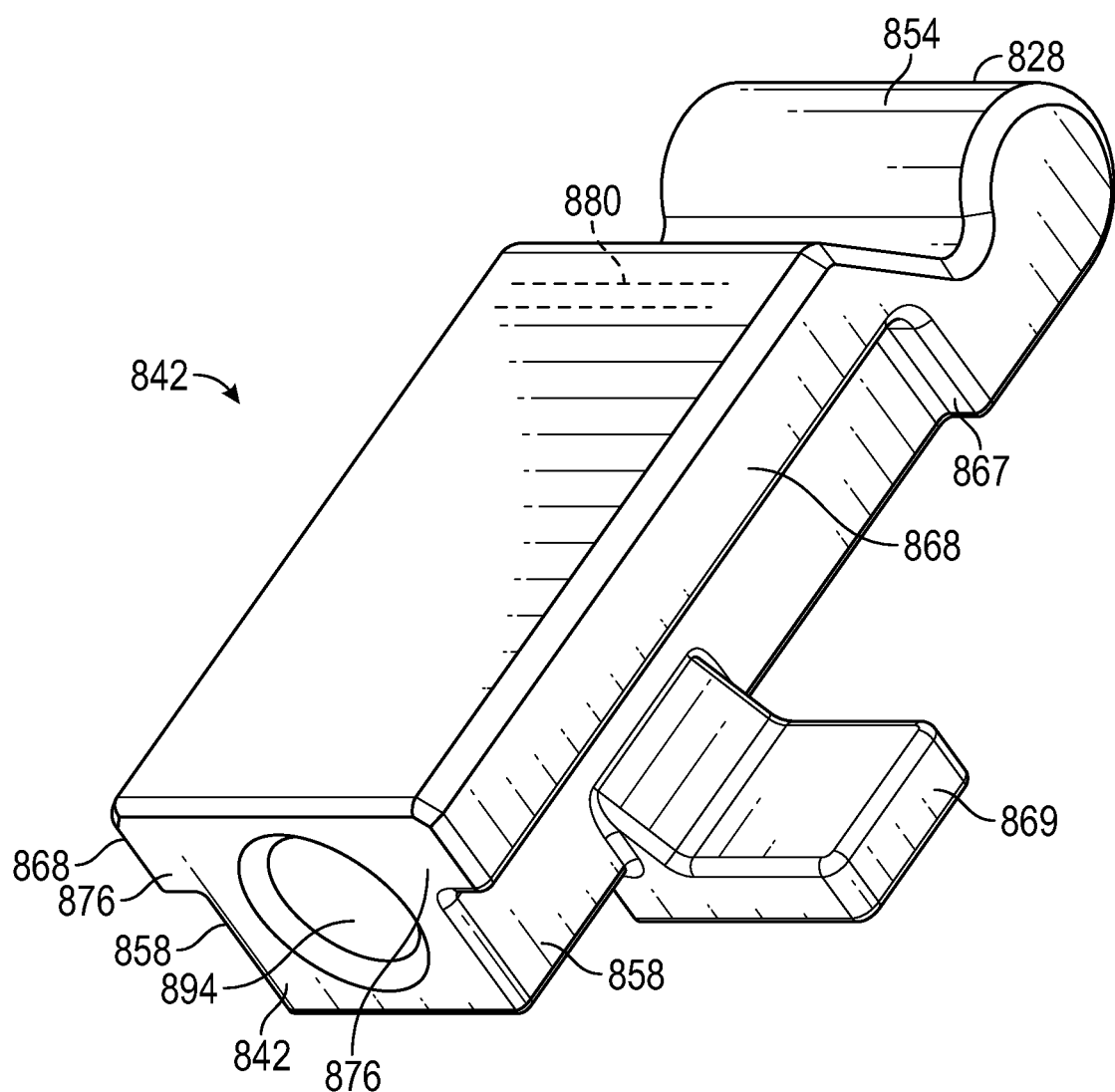
FIG. 29 is a perspective view of a first latch body of the lever of the latch assembly of FIG. 27.

When the second latch body 844 is secured to the first latch body 42 during assembly of the lever 516A, the forward edge 872 is positioned at the rear ends 876 of the flanges 868, and the second latch body 844 is slid forward along the flanges 868 at least until the forward edge 872 is stopped at shoulders 867 of each side wall 858. One shoulder 867 is shown in FIG. 29, and the first latch body 842 particularly is symmetrical about a longitudinal center axis of the first latch body 842. The first latch body 842 has transversely-extending arms 869 that are disposed under the flanges 868, forming a gap on either side of the first latch body 842 in which the inner rims 886 of the side walls 862 are disposed. The arms 869 are thus under the side walls 862.

Figure 30:
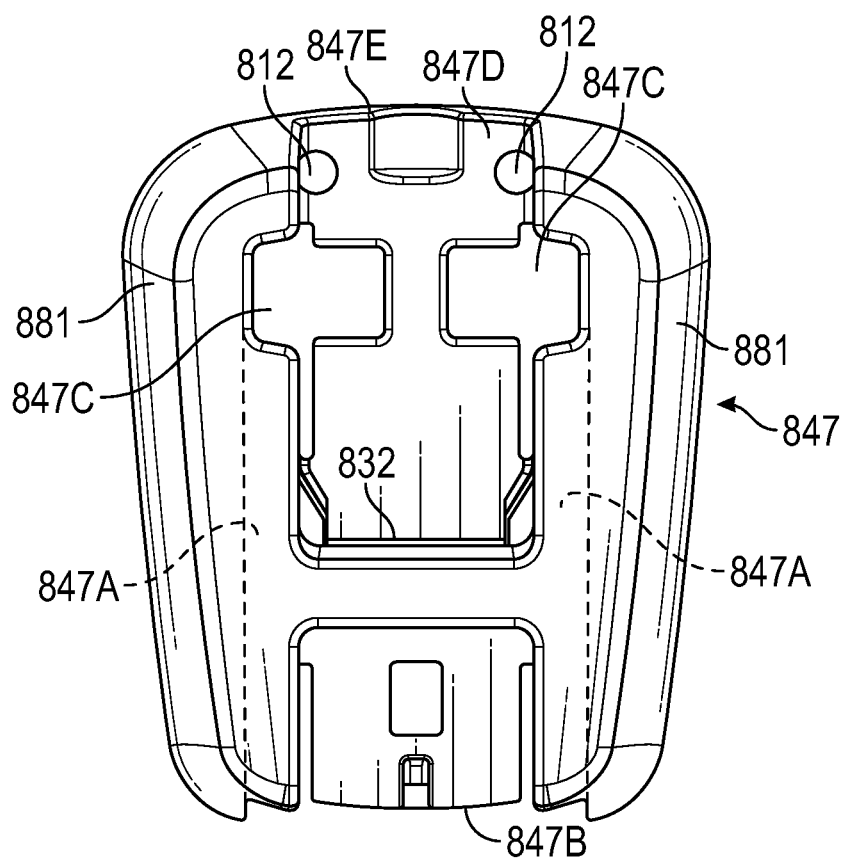
FIG. 30 is a plan view of a latch mount of the latch assembly of FIG. 27.

FIG. 30 shows the mount body 847 that is fixed or fixable to the latch base 835 in FIG. 27 such as by one or more fasteners (not shown) that extend through one or more fastener openings 812 spaced to align with one or more spaced fastener openings of the latch base 835 (the fastener openings of the latch base 835 are covered by the lever 816A in FIG. 27) Only two of the fastener openings 812 are shown, but there may be more in a bottom side of the mount body 847 under the side walls 881.

Figure 31:
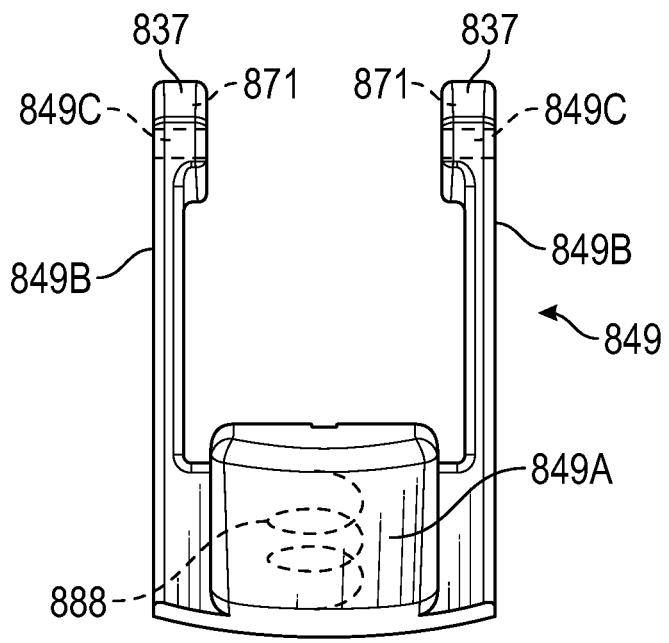
FIG. 31 is a plan view of a third latch body of the latch assembly of FIG. 27.

FIG. 31 is a plan view of a third latch body 849 of the latch assembly 816 of FIG. 27. The third latch body 849 particularly has a raised button 849A and spaced longitudinal button arms 849B extending rearward from the button 849A. Rear ends of the arms 849B have ramped surfaces 837 at their upper side, similar to ramp surfaces 537 of the latch assembly 516.

The underside of the arms 849B particularly have downwardly-extending protrusions 849C (e.g., protrusions going into the page in FIG. 31), creating a notch 871 at a forward end of each arm 849B (e.g., forward of the protrusion 849C and under the ramped surface 837). The mount body 847 particularly forms channels 847A extending from a front edge 847B to apertures 847C formed in the mount body 847. The longitudinal arms 849B at least partly fit within the channels 847A and can be slid rearward in the channels 847A from the front edge 847B so that the protrusions 849C extend downward in the apertures 847C. The mount body 847 forms a recess 847D extending from a rear edge 847E to a front catch 832 formed by the mount body 847.

When the lever 816A is being latched by placing the lip 854 of first latch body 842 in the catch 832 and pivoting the lever 816A rearward and downward about the lip 854, the lever 816A fits in the recess 847D with strap-connection arms 844A extending rearward of the recess 847D. Each of the strap-connection arms 844A defines a three-sided slot 819 that opens toward the latch base 835. The strap 18 is threaded through the slots 819 to extend through the lever 816A near a rear end 830 of the lever 816A.

A guide plate 831 particularly is secured to the second latch body 844 between the slots 819 to help guide the strap 18 between the slots 819. When the sole plate 14 with the strap 18 secured thereto is latched to the prosthetic foot blade 10 by the latch assembly 816, the tension of the strap 18 wedges the lip 854 into the front catch 832.

The ends of the arms 849B are disposed so that, during latching, the arms 869 of the first latch body 842 particularly slide on the ramped surfaces 837 and are captured in the notches 871 under the button arms 849B with the protrusions 849C interfacing with the forward faces of the arms 869 of the first latch body 842.

Additionally, a biasing member such as a compression spring 888 is disposed in a channel of the button 849A and/or is compressed between a wall of the button 849A and structure of the mount body 847 that extends into the channel of the button 849A when the button is pushed forward (e.g., downward in FIG. 27). The spring force of the spring 888 biases the arms 869 against the protrusions 849C of the arms 849B.

The button portion 849A particularly functions as a release button. When the button 849A is pushed forward (e.g., toward the distal end of the prosthetic foot blade 10 when the latch assembly 816 is secured to the prosthetic foot blade 10), the button arms 849B slide with the button 849A, releasing the arms 869 from the notches 871 which allows the lever 816A to be pivoted forward about the lip 854 and lifted away from the mount body 847 to unlatch the latch assembly 816.

Specifically, the latch assembly 816 includes a tension adjustment device like tension adjustment device 500 described with respect to latch assembly 516, including a threaded adjustment screw extending longitudinally within the lever 816A (e.g., within a channel 894 of the first latch body 842 shown in FIG. 29) and interfacing with an internal transverse wall 880 of the first latch body 842 (shown with hidden lines in FIG. 29) to adjust an overall distance between the front end 828 and the rear end 830 in the latched position. Because the strap 18 is connected to the second latch body 844 via the slots 819, tension in the strap 18 is increased or decreased via the tension adjustment device. A rear end of the screw has a socket at which the adjustment screw may be engaged with a tool to move the screw fore and aft along the longitudinal axis of the lever 816A. As shown in FIG. 28, the second latch body 844 has a rear window 807 through which the socket may be accessed.

Figure 32:
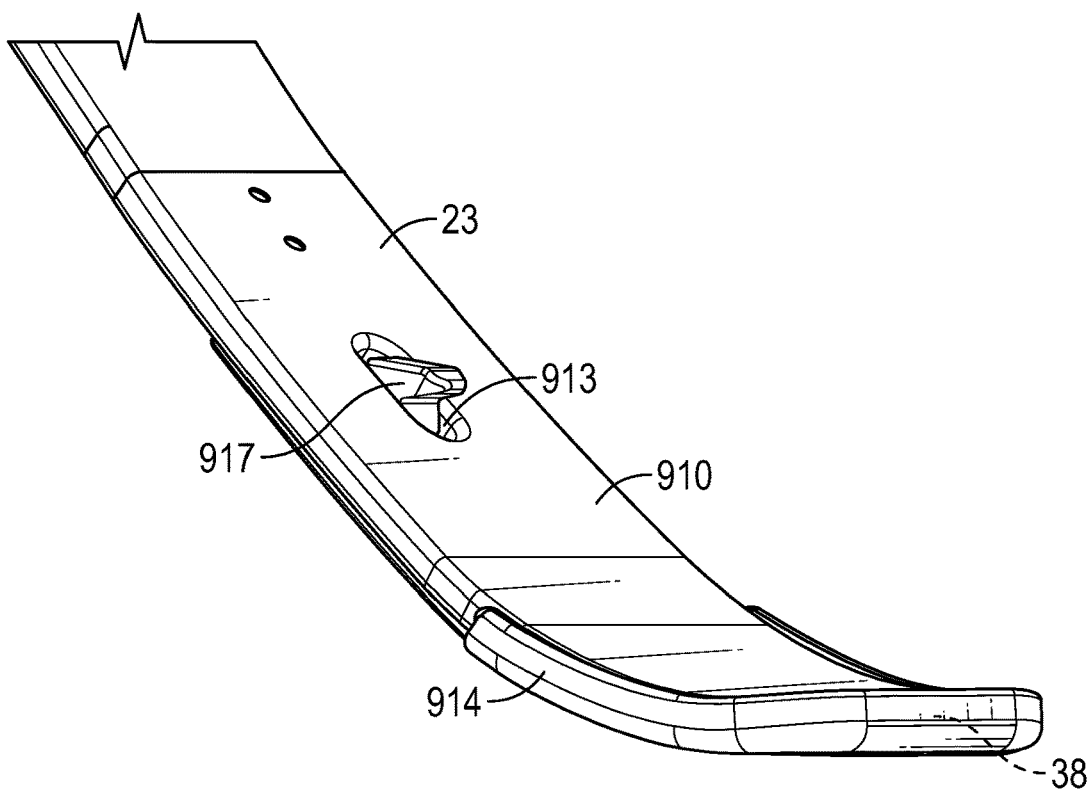
FIG. 32 is a top perspective and fragmentary view of a prosthetic foot blade, a sole plate of a traction system extending under the prosthetic foot blade, and a mount extending from the sole plate through an aperture in the prosthetic foot blade.

FIG. 32 is a top perspective and fragmentary view of an ambulatory support (particularly in the form of a prosthetic foot blade 910) and a sole plate 914 of a traction system extending under the prosthetic foot blade 910 and around and over a distal end 38 of the prosthetic foot blade 910.

Figure 33:
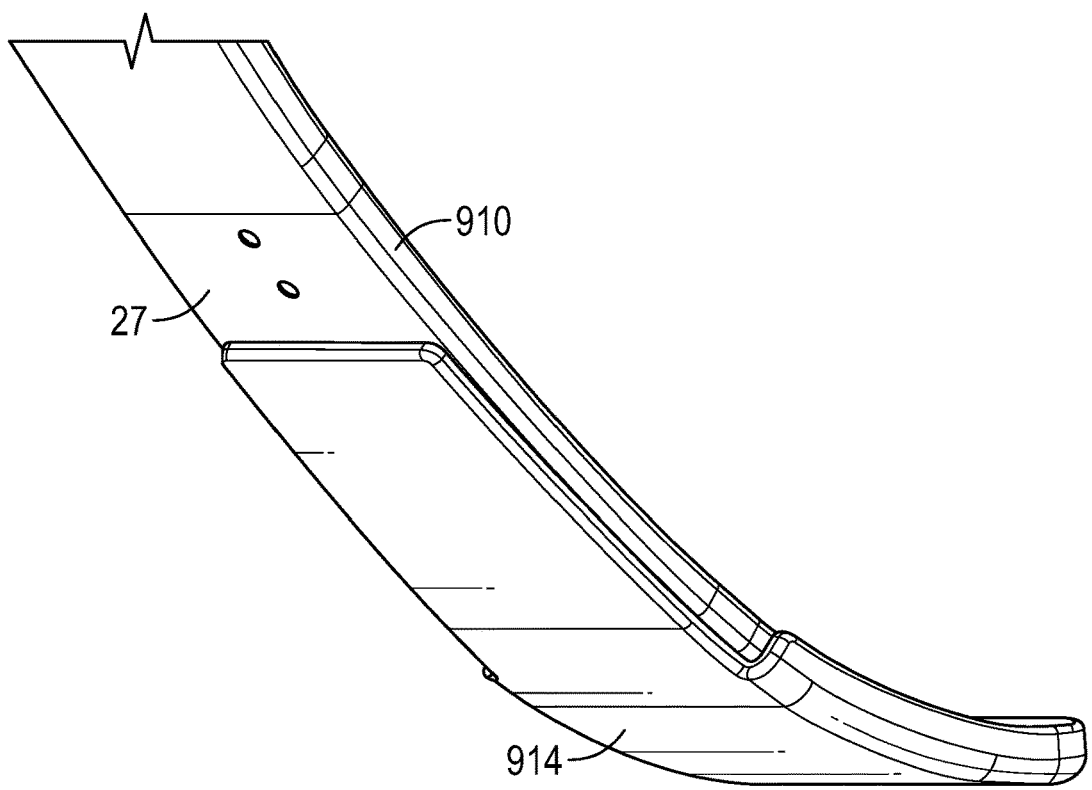
FIG. 33 is a bottom perspective and fragmentary view of the prosthetic foot blade and sole plate of FIG. 32.

FIG. 33 is a bottom perspective and fragmentary view of the prosthetic foot blade 910 and sole plate 914 of FIG. 32. The prosthetic foot blade 910 has a through hole 913 extending entirely through the prosthetic foot blade 910 from the bottom side 27 to the top side 23. The sole plate 914 has at least one mount 917 that extends from the top surface of the sole plate 914 through the through hole 913, with a portion of the mount 917 protruding above the sole plate 914.

The protruding portion of the mount 917 may be configured to connect to a latch assembly (not shown) to secure the latch assembly at the top side 23 of the prosthetic foot blade 910 with the strap 18 connected to the latch assembly and the sole plate 914. For example, a fastener opening may extend through the protruding portion to attach a latch assembly to the protruding portion. In this manner, different latch assemblies, such as different spring-biased draw latch assemblies, may be used with the prosthetic foot blade 910 and the sole plate 914 to tension the strap 18 and secure the sole plate 914 at the distal end 38 and the bottom side 27 of the prosthetic foot blade 910. Alternatively, in some implementations, the mount 917 could instead function as a strap mount, with a slot in the mount 917 configured to receive the strap 18 when the sole plate 914 is coupled to the prosthetic foot blade 910.

Figure 34:
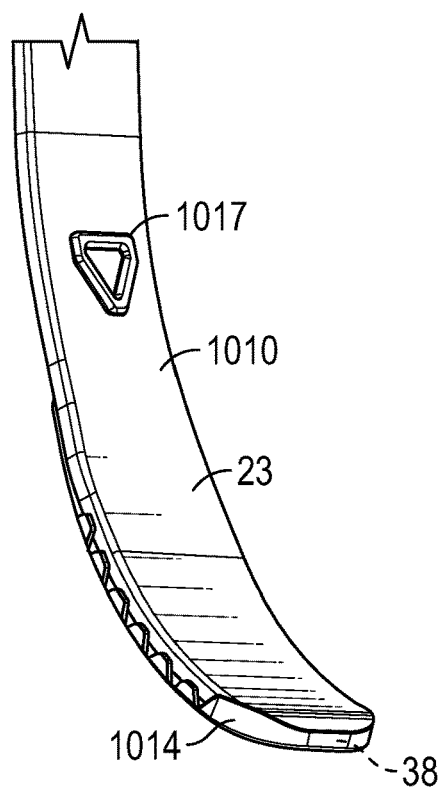
FIG. 34 is a top perspective and fragmentary view of a prosthetic foot blade, a sole plate of a traction system extending under the prosthetic foot blade, and a mount fixed to a top side of the prosthetic foot blade.
Figure 35:
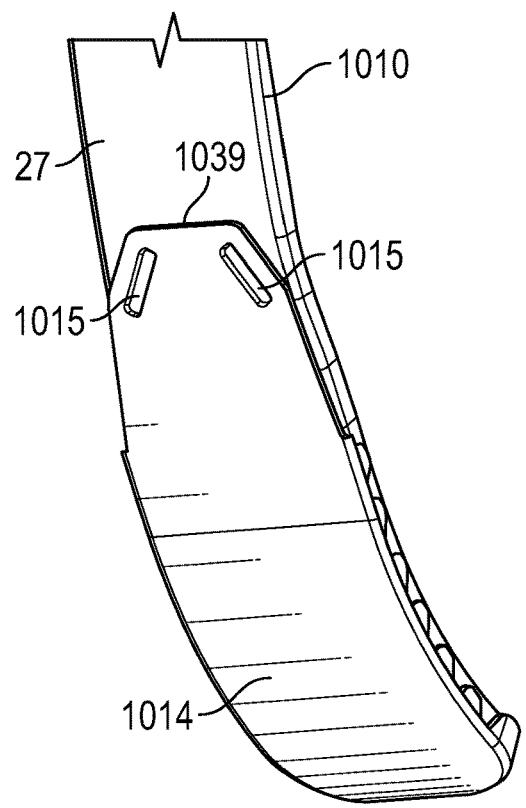
FIG. 35 is a bottom perspective and fragmentary view of a prosthetic foot blade and sole plate of FIG. 34.

FIG. 34 is a top perspective and fragmentary view of an ambulatory support (particularly in the form of a prosthetic foot blade 1010), a sole plate 1014 of a traction system extending under the prosthetic foot blade 1010, and a mount 1017 fixed to a top side 23 of the prosthetic foot blade 1010. The sole plate 1014 is shown extending under a bottom side 27 (see FIG. 35) of the prosthetic foot blade 1010 and around and over a distal end 38 of the prosthetic foot blade 1010. The sole plate 1014 has slots 1015 near opposite sides of the sole plate 1014 and near the proximal edge 1039 of the sole plate 1014 as shown in FIG. 35. A single strap 18 or two separate straps 18 may extend through the slots 1015 and under a protruding portion of the mount 1017 (e.g., between the mount 1017 and the top side 23 of the prosthetic foot blade 1010) to secure the sole plate 1014 to the prosthetic foot blade 1010. Alternatively, a latching assembly could be secured to the latch mount 1017 and the straps 18 could secure to the latching assembly.

Figure 36:
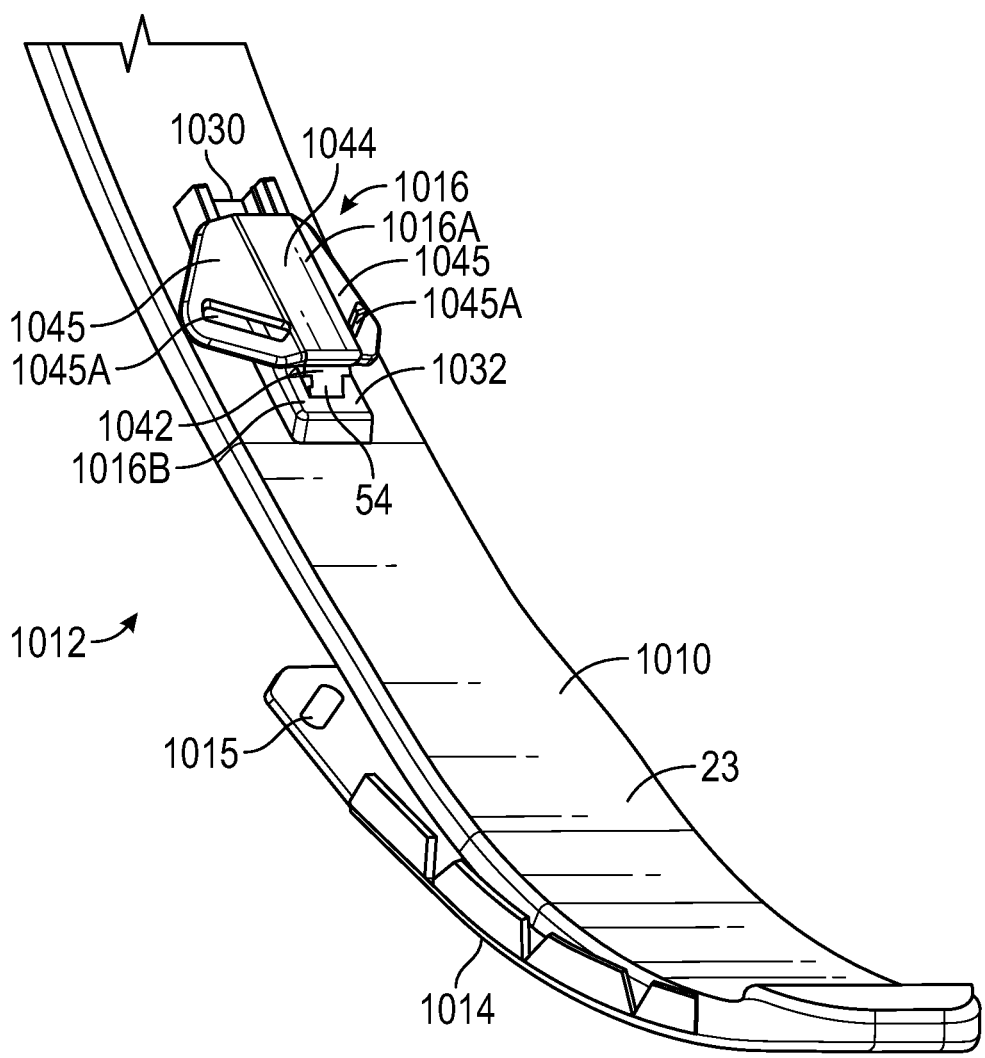
FIG. 36 is a top perspective and fragmentary view of a prosthetic foot blade, a sole plate of a traction system extending under the prosthetic foot blade, and a latching assembly including a latch mount fixed to a top side of the prosthetic foot blade and a lever latched to the latch mount.

FIG. 36 is a top perspective and fragmentary view of the prosthetic foot blade 1010, with a traction system 1012 that includes the sole plate 1014 (shown only partially secured to the prosthetic foot blade 1010) and a latch assembly 1016. The latch assembly 1016 includes a latch mount 1016B fixed to a top side 23 of the prosthetic foot blade 1010 and a lever 1016A latched to the latch mount 1016B. More specifically, a front lip 54 of a first latch body 1042 of the lever 1016A is captured in a front catch 1032 similar to front catch 32 capturing the lip 54 of the lever 16A.

A second latch body 1044 is secured to the first latch body 1042 according to any manner discussed with respect to the first latch body secured to the second latch body of any of the latch assemblies configured as spring-biased draw latches as discussed herein, and has a rear end 1030 biased apart from the front end 28 by a biasing member such as any of the springs discussed herein. The second latch body 1044 has lateral wings 1045 each having a slot-like through hole 1045A extending therethrough. The strap 18 (not shown in FIG. 36) may extend from the slots 1015 of the sole plate 1014 and through the through holes 1045A of the second latch body 1044, which will pull the sole plate 1014 against the bottom side of the prosthetic foot blade 1010. Securing the latch assembly 1016 thus tensions the strap 18.

Figure 37:
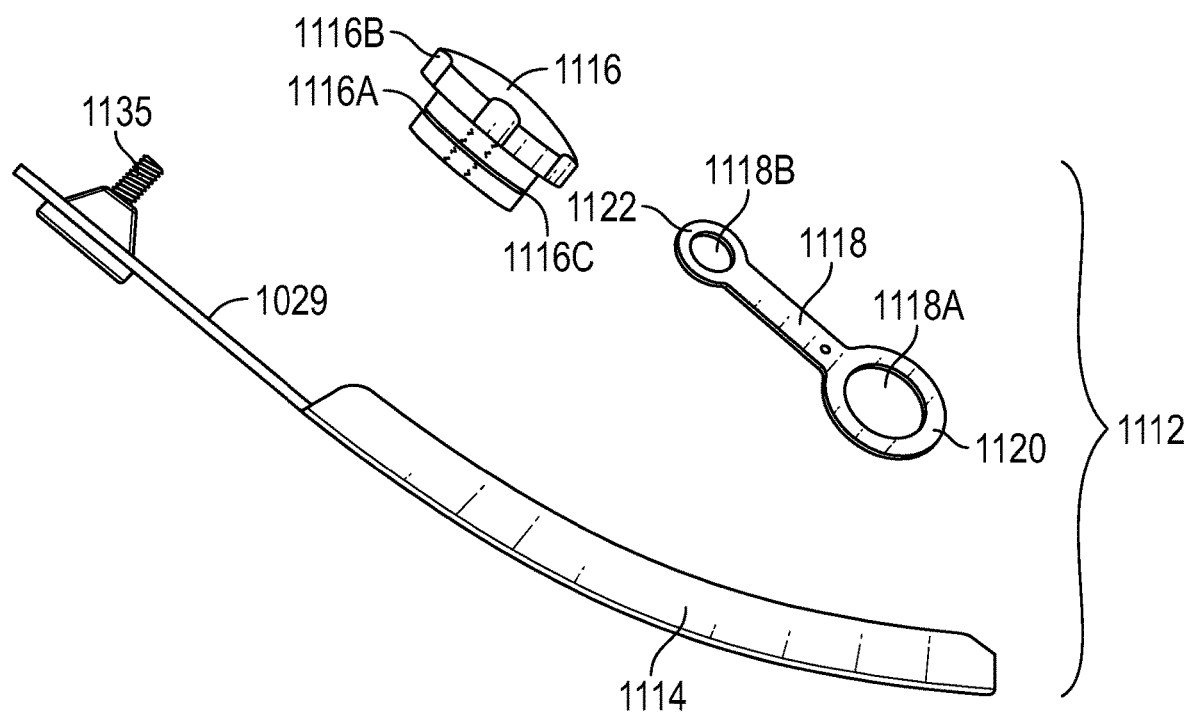
FIG. 37 is an exploded side view of a traction system for a prosthetic foot blade including a knob and a tether for the knob.

FIG. 37 is an exploded side view of a traction system 1112 for an ambulatory support (particularly in the form of a prosthetic foot blade 1110). The traction system 1112 includes a sole plate 1114 configured similarly to sole plate 14 except having an externally-threaded post 1135 extending from the top side 1029 of the sole plate 1014.

The traction system 1112 also includes at least one internally-threaded securing member, such as an internally-threaded knob 1116, and/or at least one tether 1118 to retain the knob to the prosthetic foot blade 1110. The sole plate 1114 is couplable to the distal end 38 of the prosthetic foot blade 1110 to extend under a bottom side of the prosthetic foot blade 1110 and forward of and partially over the distal end 38. The knob 1116 is securable to the externally-threaded post 1135 by threading an internally-threaded opening 1117 in a shank portion 1116A of the knob 1116 onto the post 1135 by turning the handle portion 1116B of the knob 1116 after the sole plate 1114 is coupled at the distal end 38.

The prosthetic foot blade 1110 defines at least one through hole 1113 extending through the prosthetic foot blade from the bottom side to a top side of the prosthetic foot blade 1110. The threaded post 1135 extends through the through hole 1113 and at least partly into the shank portion 1116A of the knob 1116 when the sole plate 1114 is coupled to the distal end 38 of the prosthetic foot blade 1110. The sole plate 1114 is retained against the bottom side of the prosthetic foot blade 1110 when the knob 1116 is secured to the threaded post 1135.

Figure 38:
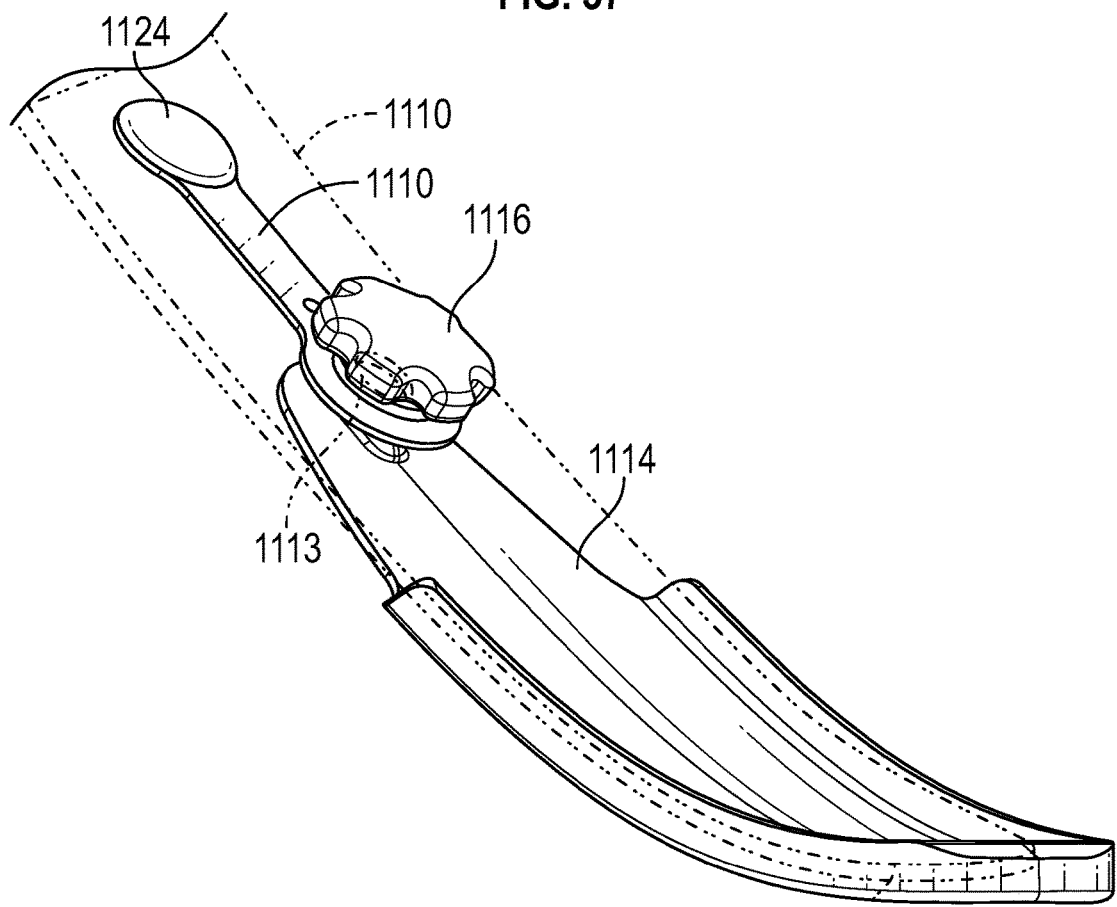
FIG. 38 is a top perspective view of the traction system of FIG. 37 secured to a prosthetic blade shown in phantom.

To help retain the knob 1116 to the prosthetic foot blade 1110, such as when fastening and unfastening the knob 1116, the traction system 1112 particularly includes a tether 1118 with a first aperture 1118A through which the shank portion 1116A of the knob 1116 extends. The ring 1120 formed by the tether 1118 around the aperture 1118A may be seated in an annular groove 1116C (see FIG. 37) in the exterior surface of the shank portion 1116A of the knob 1116. The ring 1122 formed by the tether 1118 around the aperture 1118B may be secured to the prosthetic foot blade 1110 with a fastener 1124 such as a bolt or snap that fastens to another fastener or fastener portion secured to the prosthetic foot blade 1110 as shown in FIG. 38. In this manner the tether 1118 is held to the prosthetic foot blade 1110 at the ring 1122, and the knob 1116 is held to the tether 1118, during securing and unsecuring of the knob 1116 to the threaded post 1135.

Figure 39:
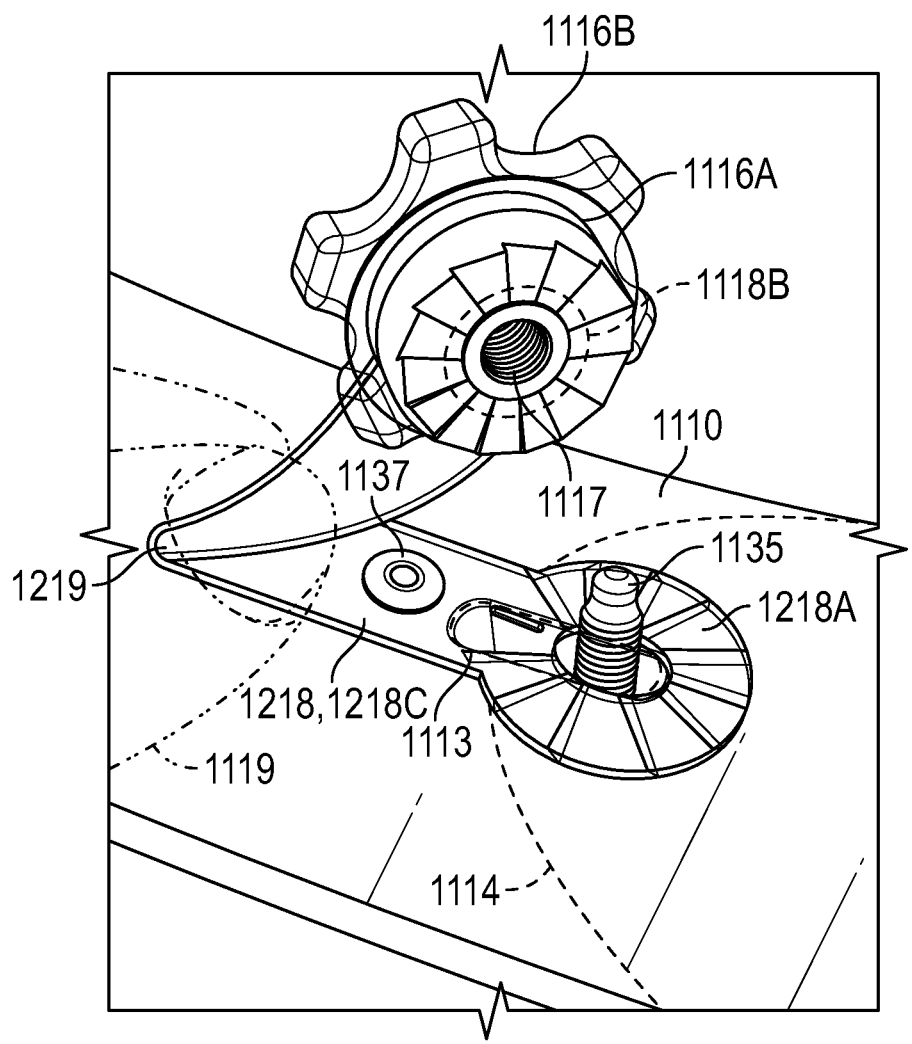
FIG. 39 is a top perspective and fragmentary view of the prosthetic foot blade and traction system of FIG. 38 with an alternative tether for the knob.

FIG. 39 shows another example of a tether 1218 that could be used with the knob 1116 of FIGS. 37-38 to secure the knob 1116 to the prosthetic foot blade 1110. The tether 1218 is fastened to the top side of the prosthetic foot blade 1110 with a fastener 1137 that extends through a strap portion 1218C of the tether 1218. The strap portion 1218C is configured with a permanent fold 1219 that doubles the strap portion 1218C back toward the threaded post 1135 so that the knob 1116 is retained in the vicinity of the post 1135. A ring 1218A shown has a gripping feature in the form of radially extending ribs that interfere with a similar gripping feature on the knob 1116 to help prevent unintentional loosening of the knob 1116. In FIG. 39, a portion of a hand 1119 is shown in phantom lifting the tether 1218 at the fold 1219.

Figure 40:
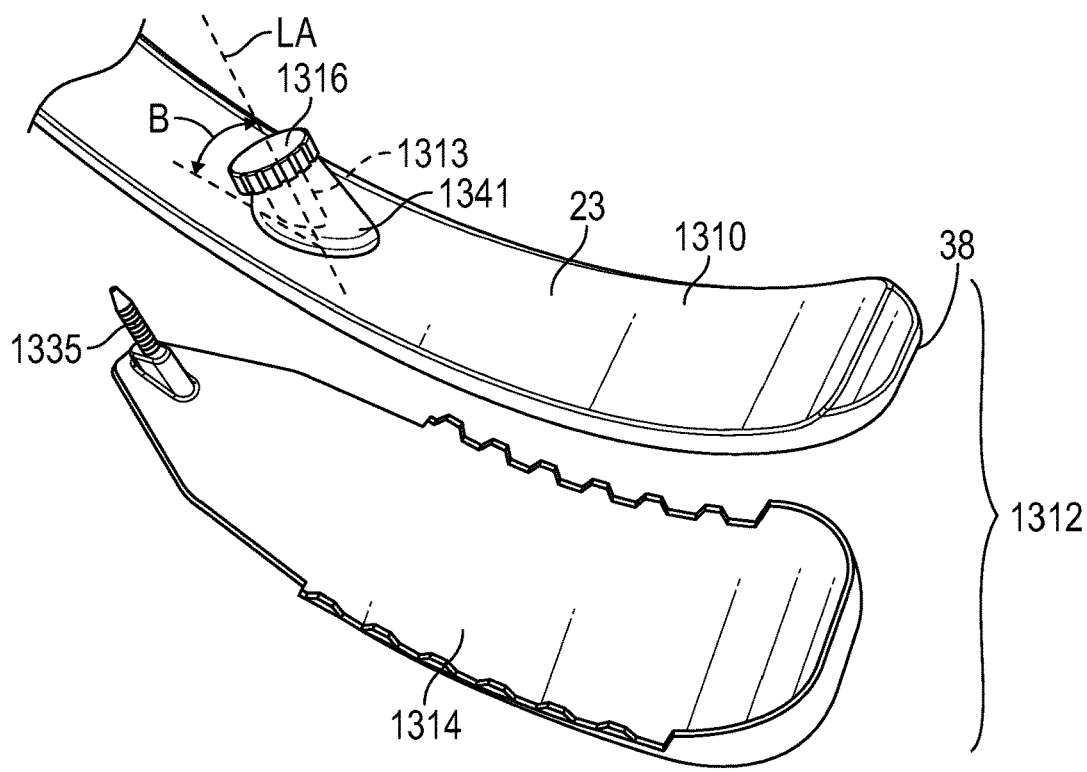
FIG. 40 is a perspective exploded top view of a prosthetic foot blade shown in fragmentary view and a sole plate of a traction system including an angled threaded tool and a knob fastenable to the tool.

FIG. 40 is a perspective exploded top view of an ambulatory support (particularly in the form of a prosthetic foot blade 1310) shown in fragmentary view and a sole plate 1314 of a traction system 1312 particularly including at least one angled threaded tool 1335, such as an externally-threaded post, and at least one internally-threaded securing member (such as internally-threaded knob 1316) fastenable to the tool 1335. A boss 1341 extends from the top side of the prosthetic foot blade 1310, and a through hole 1313 through the prosthetic foot blade 1310 also extends through the boss 1341, with a longitudinal axis LA of the through hole 1313 at an acute angle B to the top side 23 of the prosthetic foot blade 1310 (taken where the through hole 1313 extends past the top side 23). Stated differently, the through hole 1313 is tilted rearward relative to the prosthetic foot blade 1310 from the top side 23 of the prosthetic foot blade 1310 to the knob 1316.

Figure 41:
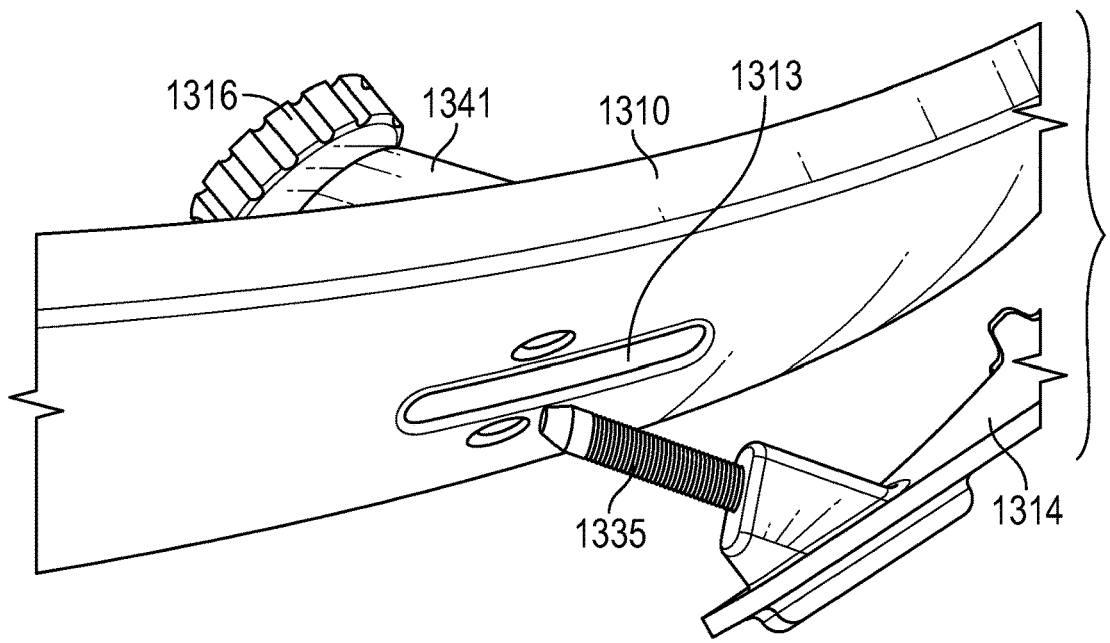
FIG. 41 is a perspective exploded bottom view of the prosthetic foot blade shown in fragmentary view and the sole plate of FIG. 40 showing the angled threaded tool.

As shown in FIG. 41, the through hole 1313 particularly is an elongated opening extending along the length of the prosthetic foot blade 1310, in order to enable easy insertion of the angled threaded tool 1335 into the through hole 1313. Because of the rearward tilt of the angled threaded tool 1335, when the knob 1316 is tightened on the tool 1335, the tool 1335 will pull the sole plate 1314 rearward (e.g., away from the distal end 38), tightening the sole plate 1314 against the distal end 38 and the bottom side of the blade 1310.

Figure 42:
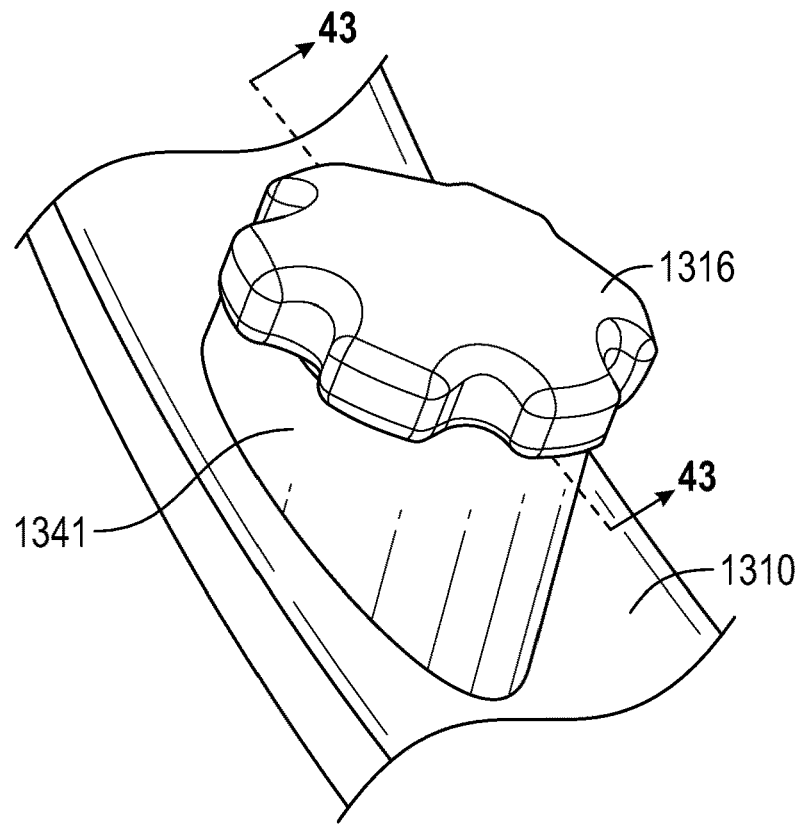
FIG. 42 is a fragmentary perspective top view of a prosthetic foot blade with a knob mount and a knob captive to the mount.
Figure 43:
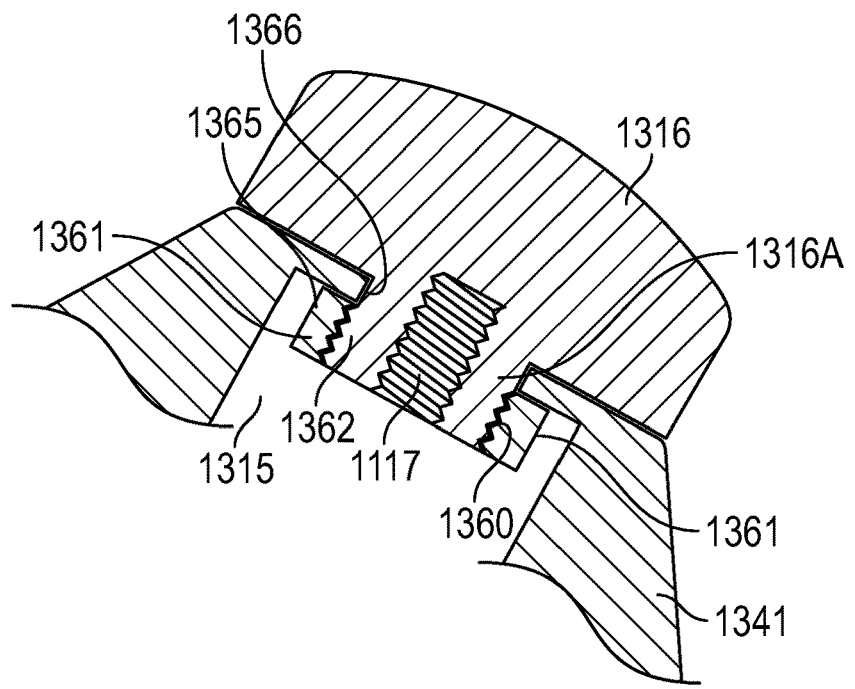
FIG. 43 is a fragmentary cross-sectional view taken at lines 43-43 in FIG. 42 showing the knob mount and the captive knob.

FIG. 42 is a fragmentary perspective top view of the prosthetic foot blade 1310 with the boss 1341 and the securing member (knob 1316) captive to the boss 1341. As best shown in FIG. 43, the shank portion 1316A of the knob 1316 has external threads 1360, and the knob 1316 includes a ring 1361 with internal threads 1362 that secure to the shank portion 1316A at the external threads 1360. The ring 1361 may be threaded to the knob 1316 from below the prosthetic foot blade 1310 through the through hole 1315, which is circular or shaped sufficiently large to allow insertion of the ring 1361. With the ring 1361 secured to the shank portion 1316A in the through hole 1315, the ring 1361 forms a flange 1365 that is larger than the knob opening 1366 to retain the knob 1316 to the boss 1341 even when a threaded tool such as threaded post 1135 is not threaded to the knob 1316 at the threaded opening 1117.

Figure 44:
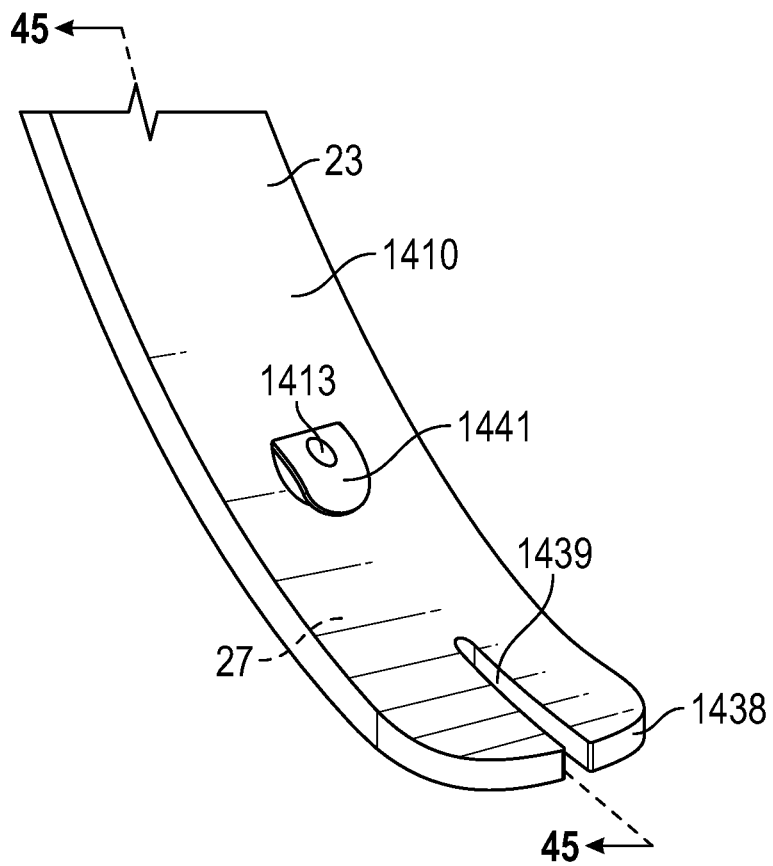
FIG. 44 is a top perspective and fragmentary view of a prosthetic foot blade with an internally-threaded boss for a fastener.

FIG. 44 is a top perspective and fragmentary view of an ambulatory support (particularly in the form of a prosthetic foot blade 1410). The prosthetic foot blade 1410 has at least one slot 1439 at a distal end 1438 particularly creating a split toe that enhances flexibility of the prosthetic foot blade 1410.

Figure 45:
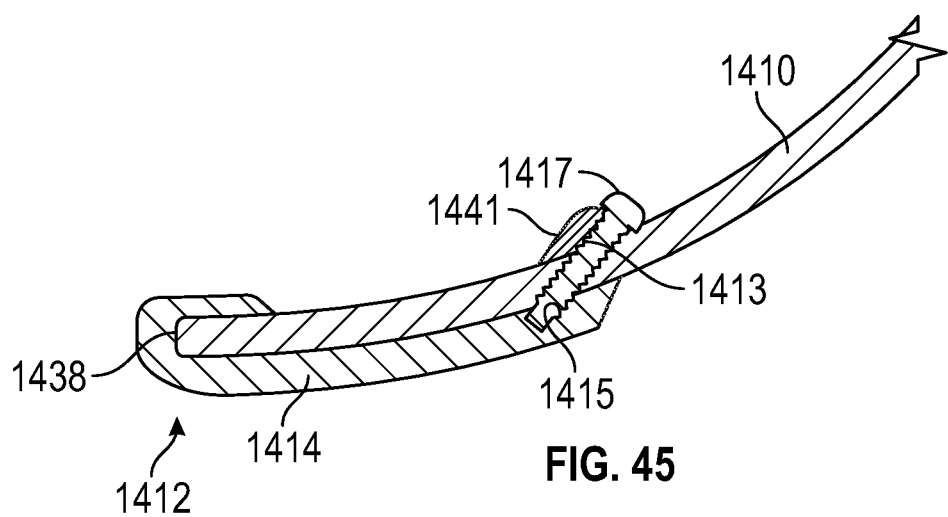
FIG. 45 is a fragmentary cross-sectional view taken along lines 45-45 in FIG. 44 showing a fastener extending through the boss and securing a sole plate to the prosthetic foot blade.

An internally-threaded boss 1441 is mounted or mountable to or integrally-formed at a top side 23 of the prosthetic foot blade 1410. The internally-threaded boss 1441 has a through hole 1413 that extends at an angle through the boss 1441 and forward from the top side 23 to the bottom side 27 of the prosthetic foot blade 1410, creating an oval-shaped opening at the boss 1441. A traction system 1412 for the prosthetic foot blade 1410 includes a sole plate 1414 that has an opening 1415 configured to align with the opening of the through hole 1413 at the bottom side 27 of the prosthetic foot blade 10 as shown in FIG. 45.

The opening 1415 receives an end of an externally-threaded fastener 1417 when the sole plate 1414 is fit over the distal end 1438, with the fastener 1417 engaging the boss 1441, the blade 1410, and the sole plate 1414 to secure the sole plate 1414 against the distal end 1438 and the bottom side 27 of the prosthetic foot blade 1410. The sole plate 1414 may have spike mounts at a bottom side to receive spikes, or an outsole that secures to the sole plate 1414 at the bottom side may have mounts that receive spikes. The fastener 1417 may be configured so that the same tool may be used to tighten and loosen the fastener 1417 as well as the spikes.

Figure 46:
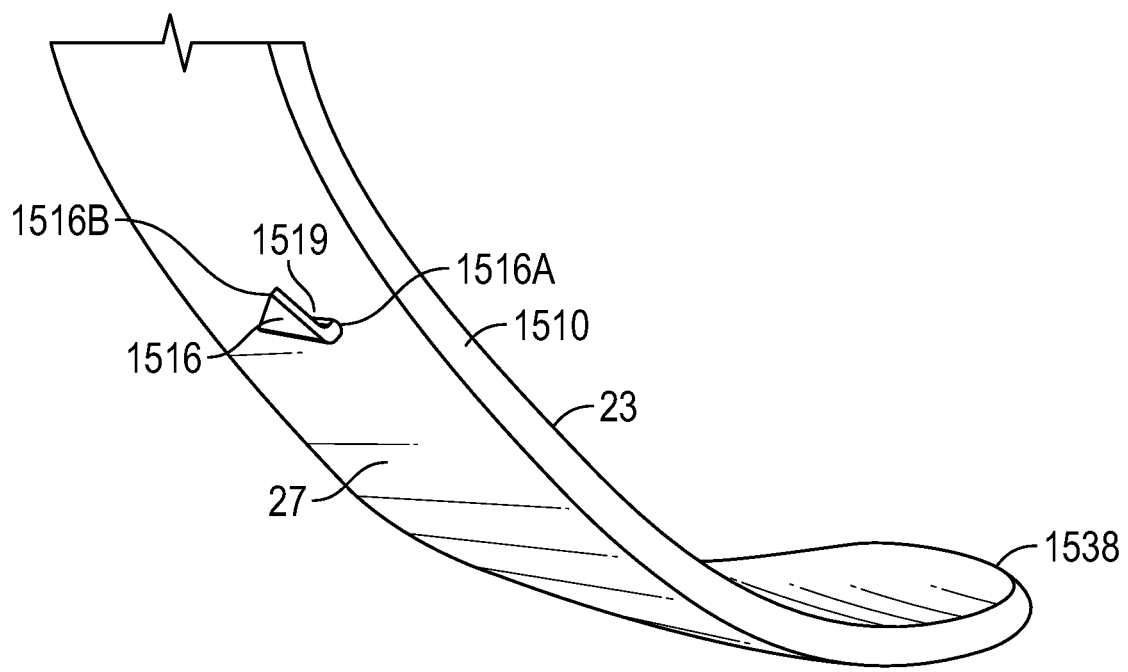
FIG. 46 is a rear perspective and fragmentary view of a prosthetic foot blade with a rear hook.

FIG. 46 is a rear perspective and fragmentary view of an ambulatory support (particularly in the form of a prosthetic foot blade 1510) that has at least one rear hook 1516 secured to or arranged at the bottom side 27 of the prosthetic foot blade 1510. A traction system 1512 for the prosthetic foot blade 1510 includes a sole plate 1514 and the rear hook 1516.

Figure 47:
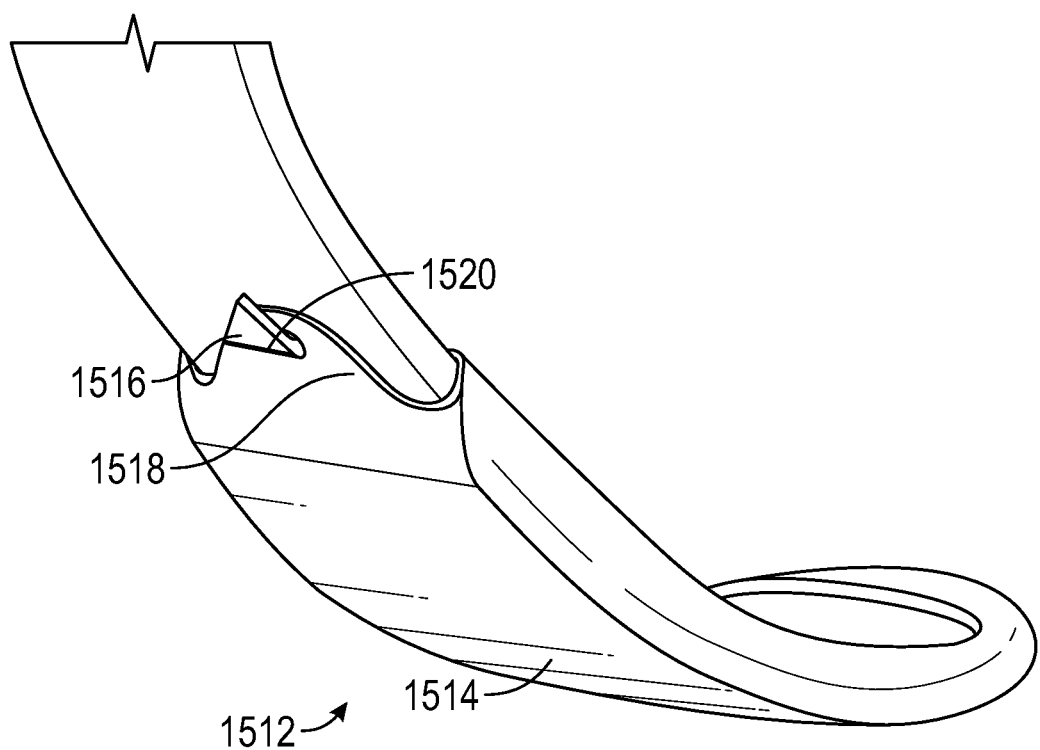
FIG. 47 is a rear perspective and fragmentary view of the prosthetic foot blade of FIG. 46 with a sole plate secured to the prosthetic foot blade at the rear hook.

As shown in FIG. 47, the sole plate 1514 is configured to fit over a distal end 1538 of the prosthetic foot blade 1510 with an attachment portion 1518 at a rear extent of the sole plate 1514 having at least one aperture 1520 at which the attachment portion 1518 fits over and hooks to the at least one respective rear hook 1516 to secure the sole plate 1514 against the distal end 1538 and/or against the bottom side 27 of the prosthetic foot blade 1510.

The rear hook 1516 particularly has a triangular or pointed shape mounted at its base 1516A closest to the distal end 1538 to create a gap 1519 disposed between the bottom side 27 of the prosthetic foot blade 1510 and the rear hook 1516 and extending from the apex 1516B to the base 1516A. The attachment portion 1518 at least partly fits in the gap 1519 and may be slightly elastic, for example, to stretch over the apex 1516B during attachment and removal of the sole plate 1514.

Figure 48:
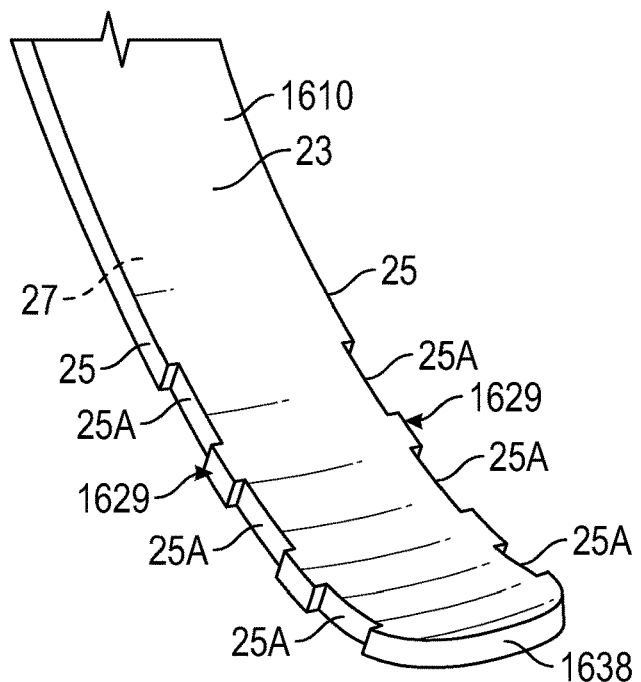
FIG. 48 is a top perspective and fragmentary view of a prosthetic foot blade with castellated side surfaces.

FIG. 48 is a top perspective and fragmentary view of an ambulatory support (particularly in the form of a prosthetic foot blade 1610) that has one or more castellated side surfaces 1629. More specifically, a series of regularly or irregularly spaced recesses 25A extend from the top side 23 to the bottom side 27 of the prosthetic foot blade 1610 at one or both sides, particularly at each of the sides 25, near the distal end 1638 of the prosthetic foot blade 1610.

Figure 49:
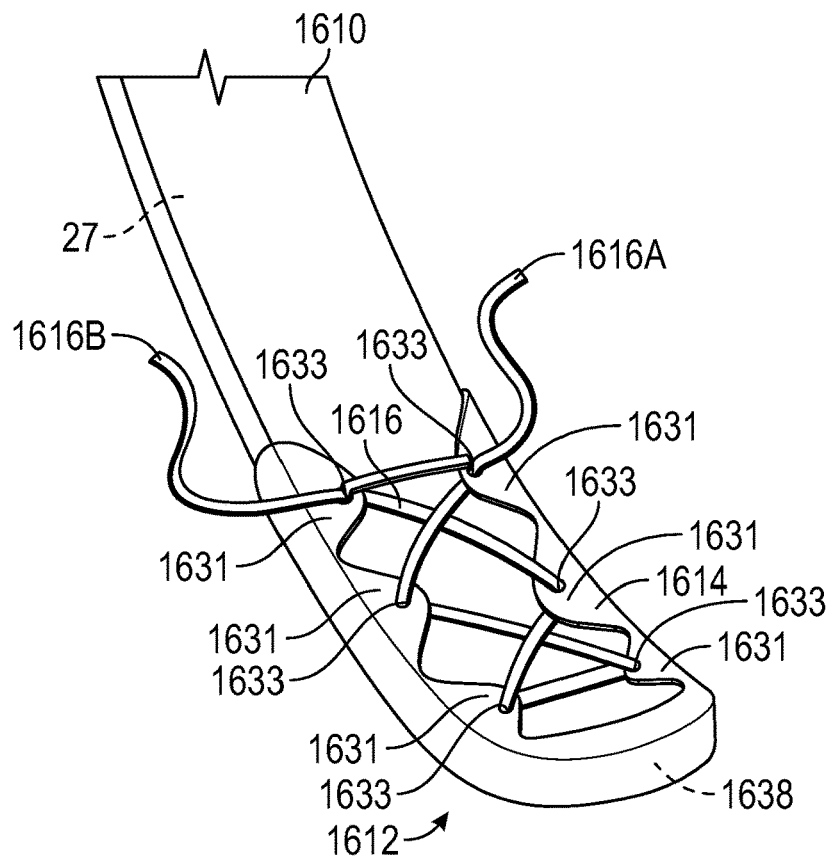
FIG. 49 is a top perspective and fragmentary view of the prosthetic foot blade of FIG. 48 with a sole plate secured to the prosthetic foot blade with a lace.

FIG. 49 shows a traction system 1612 for the prosthetic foot blade 1610 that includes a sole plate 1614 fit against the bottom side 27 and the distal end 1638 of the prosthetic foot blade 1610. The sole plate 1614 extends under the bottom side 27 and around the side surfaces 1629, terminating at top flanges 1631 that extend inward, creating a throat. Each flange 1631 has an aperture 1633.

At least one lace or other tensioning member 1616 is or may be routed through the apertures 1633 and has ends 1616A, 1616B that may be secured to the blade 1610 or tied to one another to secure the lace 1616 and tighten the sole plate 1614 against the prosthetic foot blade 1610.

Specifically, the flanges 1631 are generally aligned with the recesses 25A so that tightening the lace 1616 cinches the sole plate 1614 into the recesses 25A, the recesses functioning as waists that prevent the sole plate 1614 from slipping downward off of the distal end 1638 during use.

Figure 50:
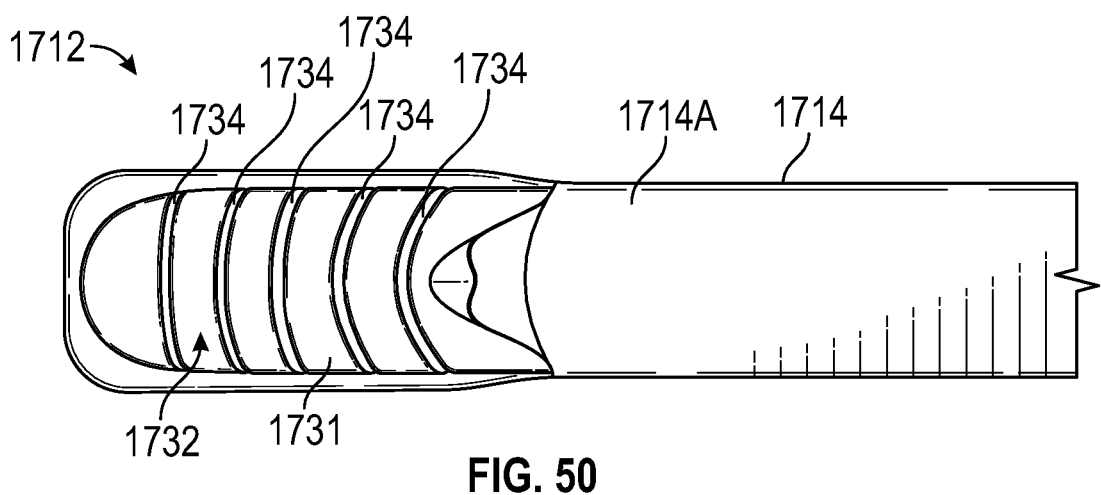
FIG. 50 is a top fragmentary view of a sole plate for a prosthetic foot blade.
Figure 51:
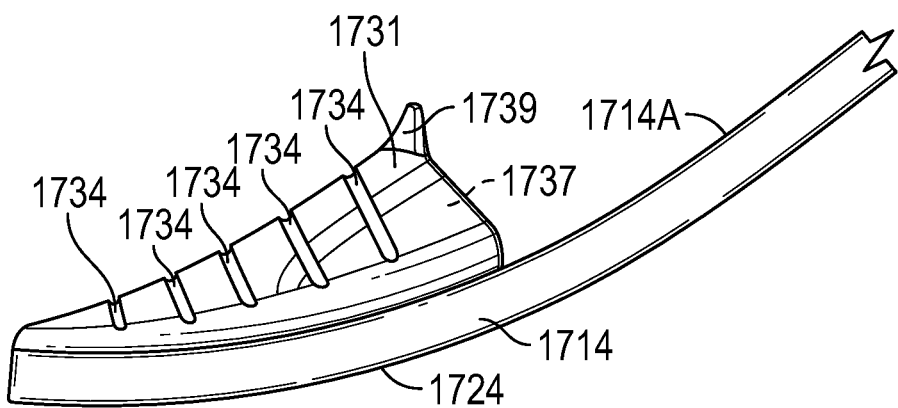
FIG. 51 is a fragmentary side view of the sole plate of FIG. 50.
Figure 52:
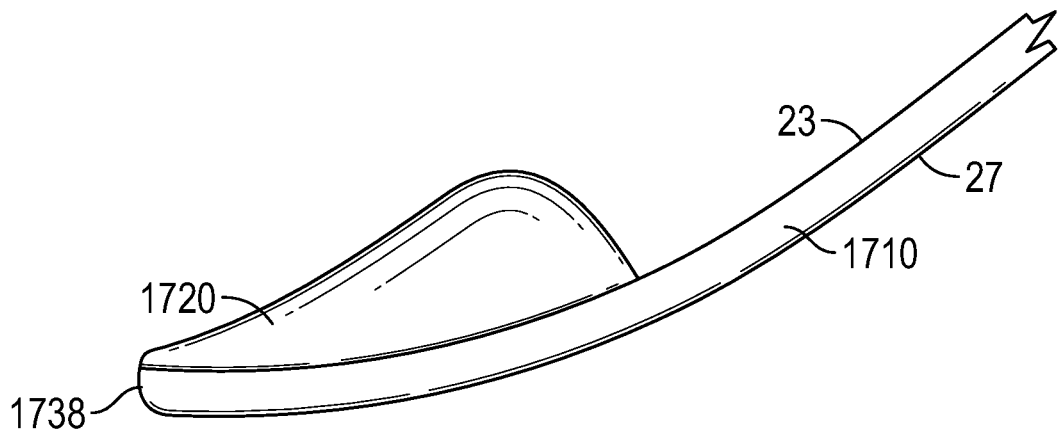
FIG. 52 is a fragmentary side view of a prosthetic foot blade configured to be used with the sole plate of FIGS. 50-51.

FIG. 50 is a top fragmentary view of a traction system 1712 with a sole plate 1714 configured to be secured at a distal end 1738 of the prosthetic foot blade 1710 of FIG. 52. The sole plate 1714 particularly includes a top cover portion 1731 that has an exterior surface 1732 with transverse flex grooves 1734. The top cover portion 1731 creates a cavity 1737 above a top side 1714A of the sole plate 1714. A bottom or exterior side of the sole plate 1714 serves as an outsole 1724 and/or may be configured with various protrusions for a desired tractive capability. As shown in FIG. 52, the prosthetic foot blade 1710 particularly has a form 1720 near the distal end 1638 that is configured to at least partly fit within the cavity 1737 indicated in FIG. 51.

The top cover portion 1731 may have some flexibility to fit over the form 1720 with a tension fit. The top side 1714A of the sole plate 1714 may have features that interfit with complementary features at the bottom side 27 of the prosthetic foot blade 1710. For example, the top side 1714A may have one or more protrusions that at least partly fit into one or more cavities at the bottom side 27 of the prosthetic foot blade 1710.

Specifically, a tip 1739 of the cover portion 1731 may be used for pulling the sole plate 1714 onto and off of the prosthetic foot blade 1710. The one or more flex grooves 1734 promote flexibility of the top cover portion 1731 in the longitudinal direction to match the flexing of the prosthetic foot blade 1710 during use.

FIG. 53 is a top fragmentary view and FIG. 54 is a fragmentary side view of a traction system 1812 with an alternative sole plate 1814 for an ambulatory support (particularly for an ambulatory support in the form of a prosthetic foot blade 1710 of FIG. 52). Like the sole plate 1714, the sole plate 1814 includes a top cover portion 1831. The top cover portion 1831 may include a rand 1831A of a relatively stiff material for extra support around a lower extent of the top cover portion 1831.

A bottom side of the sole plate 1814 serves as an outsole 1824 and/or may be configured with various protrusions for a desired tractive capability. The cover portion 1831 particularly defines a cavity 1837 similar to cavity 1737 over a top side 1814A of the sole plate 1814. The form 1720 of the prosthetic foot blade 1710 fits in the cavity 1837.

At least one tensioning member such as a lace 1816 particularly extends through one or more loops 1833 that form lace-receiving apertures. Specifically, a cord lock toggle fastener 1818 may lock the lace 1816 in place to secure the sole plate 1814 to the prosthetic foot blade 1710, and/or may be depressed to allow the lace 1816 to be loosened to release the sole plate 1814 from the prosthetic foot blade 1710.

Figure 55:
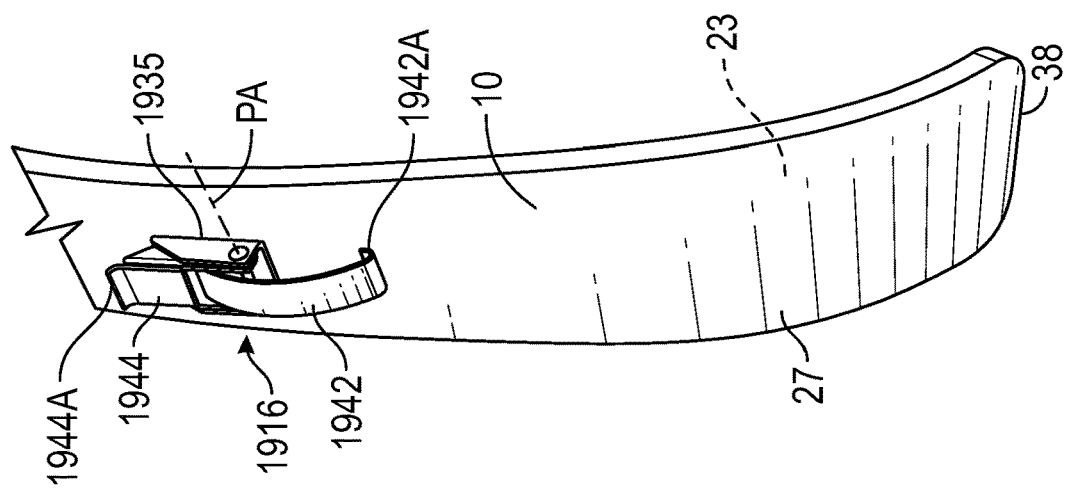
FIG. 55 is a rear perspective view of a prosthetic foot blade with a latch assembly.

FIG. 55 is a rear perspective view of the prosthetic foot blade 10 as described herein with at least one latch assembly 1916 mounted on the bottom side 27. The latch assembly 1916 particularly includes at least one latch mount 1935 mounted to the bottom side 27, a first latch body 1942 with a hooked end 1942A, and a second latch body 1944. Specifically, the latch assembly 1916 is shown in a latched position with the second latch body 1944 pivoted rearward. To unlatch the latch assembly 1916, the end 1944A of the second latch body 1944 can be lifted and pushed forward, pivoting the second latch body 1944 about a pivot axis PA, and causing the first latch body 1942 to move toward the distal end 38.

Figure 56:
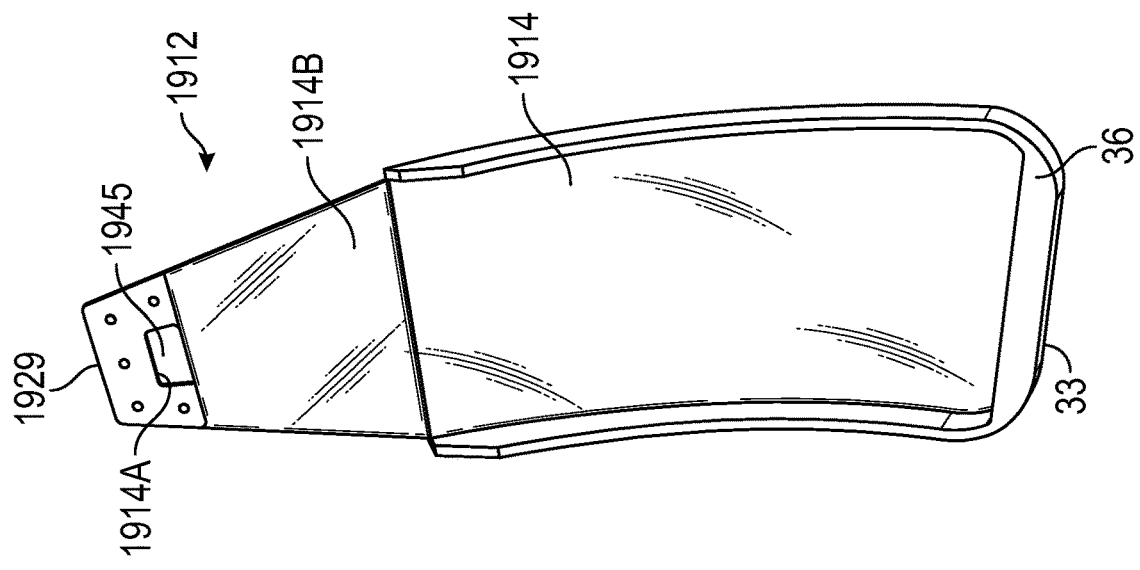
FIG. 56 is a front perspective view of a sole plate configured to latch to the prosthetic foot blade of FIG. 55.

A traction system 1912 for the prosthetic foot blade 10 includes the sole plate 1914 of FIG. 56 and the latch assembly 1916. The sole plate 1914 particularly has at least one aperture 1945 near a proximal end 1929 of the sole plate 1914, as shown in FIG. 56. Specifically, the sole plate 1914 is configured so that when the distal end 38 of the prosthetic foot blade 10 fits against the inner surface of the front wall 33 of the sole plate 1914 with the toe cap 36 extending partially over the top side 23, the hooked end 1942A can extend through the aperture 1945.

Figure 57:
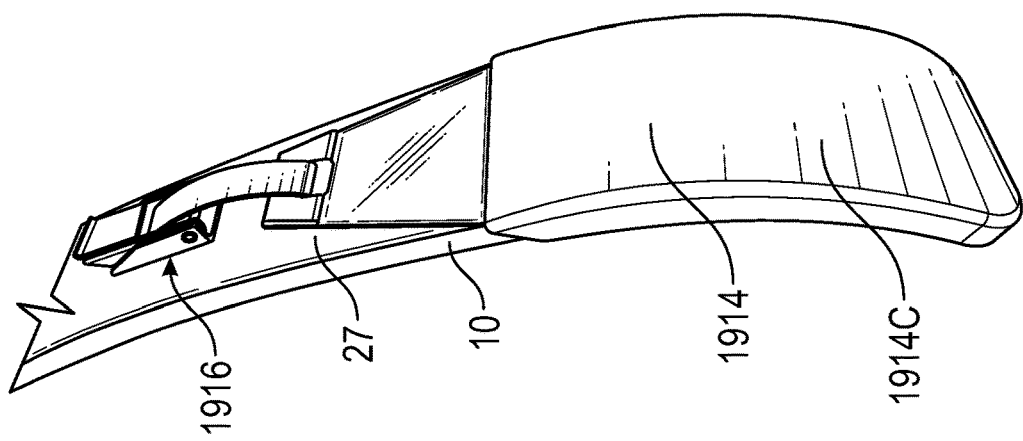
FIG. 57 is a rear perspective view of the prosthetic foot blade of FIG. 55 with the sole plate of FIG. 56 latched thereto.

When the second latch body 1944 is pivoted to or toward the latched position of FIG. 55, the hooked end 1942A catches an edge 1914A of the sole plate 1914 at the aperture 1945, substantially drawing the sole plate 1914 upward and against the bottom side 27 of the prosthetic foot blade 10 to secure the sole plate 1914 against the distal end 38 and the bottom side 27 of the prosthetic foot blade 10 as shown in FIG. 57.

A midportion 1914B of the sole plate 1914 may be thinner and/or more flexible than a portion 1914C to which an outsole (not shown) is attached in order to promote easy securement of the latch assembly 1916 to the sole plate 1914 and/or the ability of the sole plate 1914 to flex with the prosthetic foot blade 10 during use.

Figure 58:
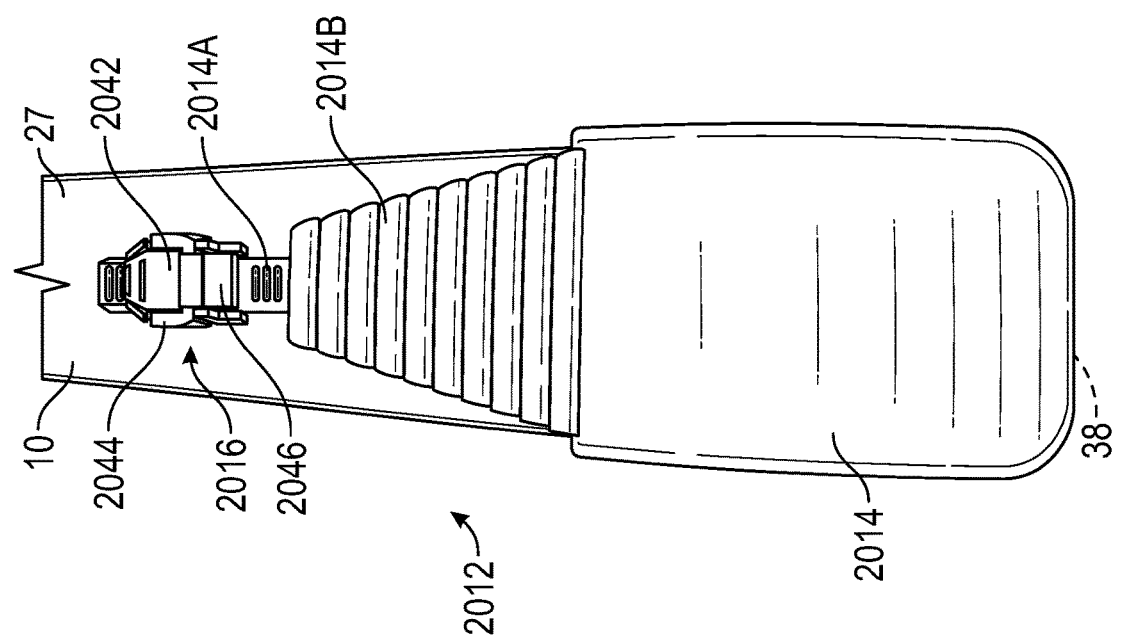
FIG. 58 is a rear view of a prosthetic foot blade with a sole plate latched thereto by a latch assembly.

FIG. 58 is a rear view of an ambulatory support (particularly in the form of a prosthetic foot blade 10) with a traction system 2012 that includes at least one latch assembly 2016 and a sole plate 2014. The latch assembly 2016 is mounted or mountable to the bottom side 27 of the prosthetic foot blade 10 and is shown in a latched position securing a sole plate 2014 and/or pulling the sole plate 2014 against the distal end 38 and the bottom side 27.

Specifically, the sole plate 2014 includes at least one ribbed strap portion 2014A at or near a proximal end. The latch assembly 2016 includes at least one latch body 2042 interfacing with the strap portion 2014A and/or that interfits with a latch body 2044 fixed to the prosthetic foot blade 10.

At least one release 2046 is depressible to release the strap portion 2014A from the latch assembly 2016. The sole plate 2014 includes at least one ribbed portion 2014B that increases the ability of the sole plate 2014 to flex with the prosthetic foot blade 10 during use.

Figure 59:
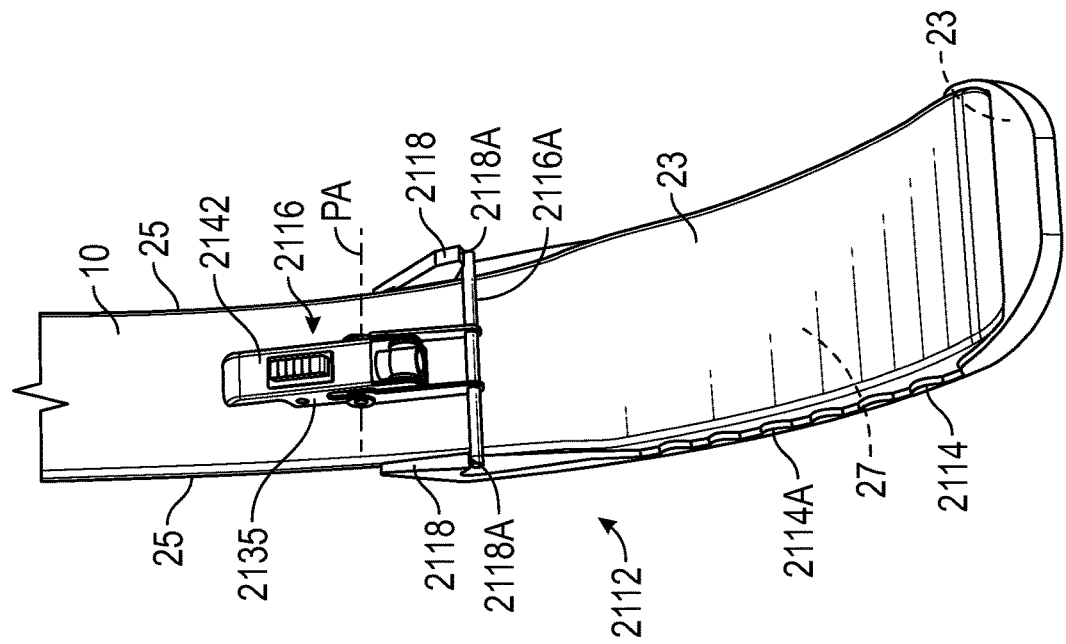
FIG. 59 is a front view of a prosthetic foot blade with a sole plate latched thereto by a latch assembly.

FIG. 59 is a front view of an ambulatory support (particularly in the form of a prosthetic foot blade 10) and a traction system 2112 for the prosthetic foot blade 10 that includes a sole plate 2114 and a latch assembly 2116 secured to the top side 23 of the prosthetic foot blade 10. The sole plate 2114 is shown latched to the prosthetic foot blade 10 by the latch assembly 2116.

Specifically, the latch assembly 2116 includes a transverse bar 2116A that is drawn substantially inward against the top side 23 and/or rearward when a latch body 2142 is pivoted rearward about a pivot axis PA relative to a latch mount 2135 to which the latch body 2142 is pivotably mounted. The sole plate 2114 has one or more stepped shoulders 2118 that extend at the sides 25 of the prosthetic foot blade 10 above the top side 23. The stepped shoulders 2118 particularly have one or more forward hooked portions 2118A that hook to the transverse bar 2116A so that the transverse bar 2116A pushes the sole plate 2114 rearward and upward against the distal end 38 and the bottom side 27 of the prosthetic foot blade 10. The sole plate 2114 also has castellated side walls 2114A.

Figure 60:
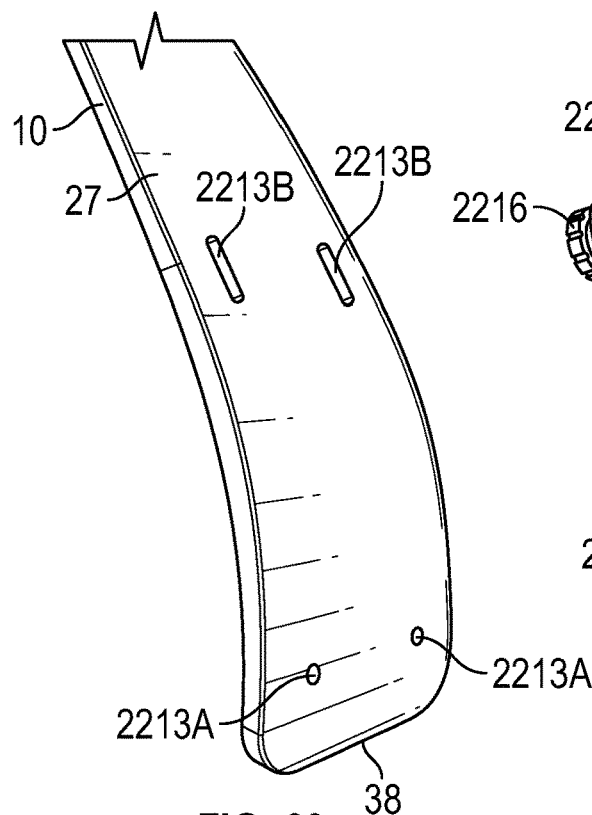
FIG. 60 is a fragmentary rear perspective view of a prosthetic foot blade.

FIG. 60 is a fragmentary rear perspective view of an ambulatory support (particularly in the form of a prosthetic foot blade 10) that has one or more circular through holes 2213A near the distal end 38 and/or one or more slotted through holes 2213B further from the distal end 38 than the through holes 2213B. The one or more slotted through holes 2213B are elongated in a direction along the length of the prosthetic foot blade 10.

Figure 61:
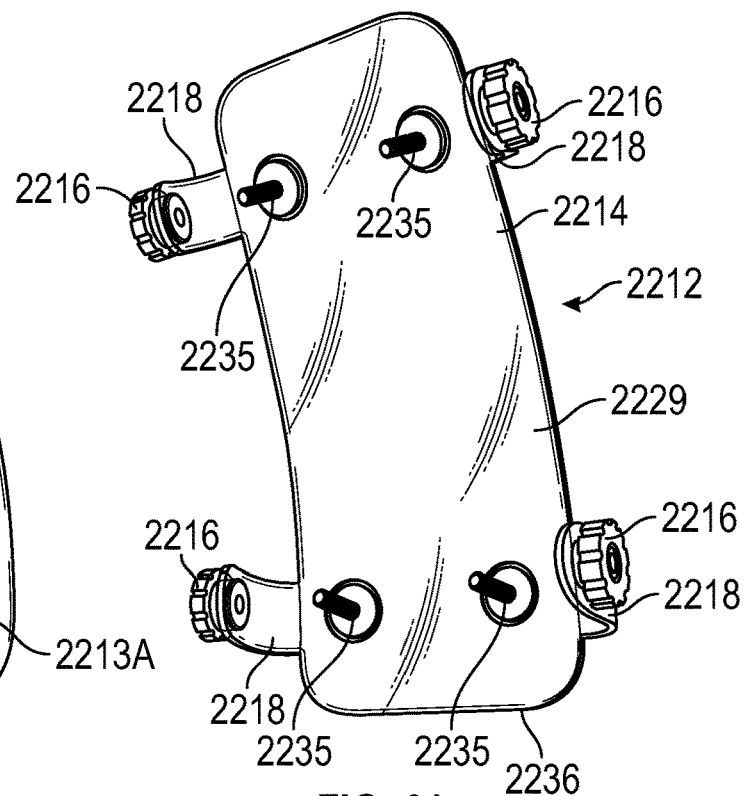
FIG. 61 is a front perspective view of a sole plate configured to secure to the prosthetic foot blade of FIG. 60.
Figure 62:
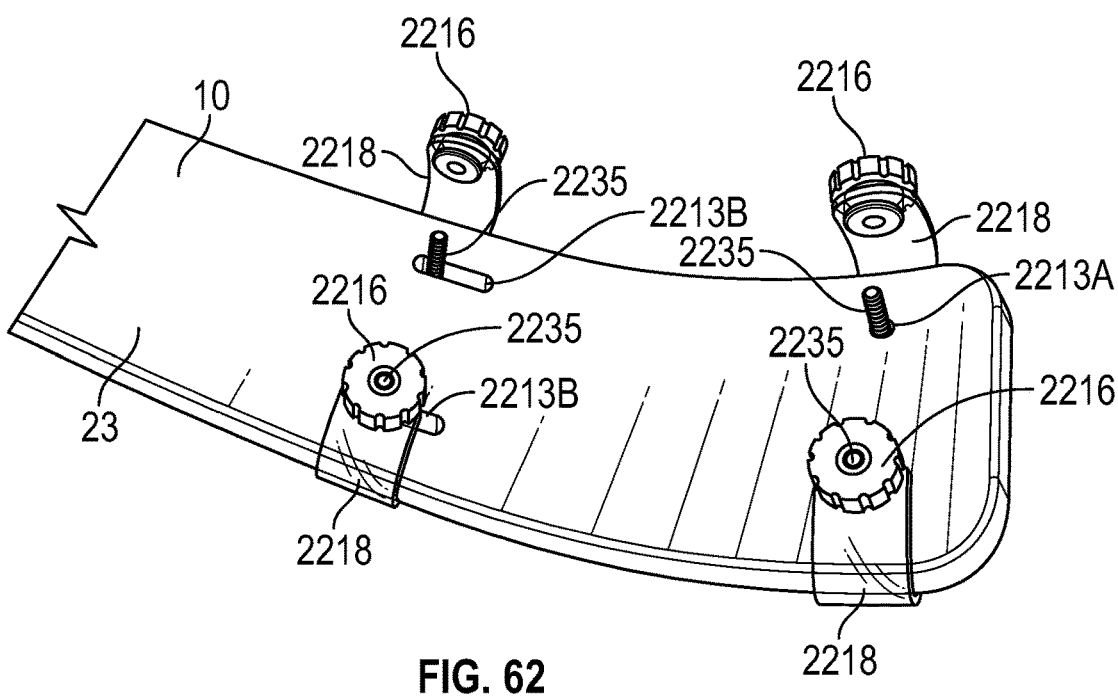
FIG. 62 is a top perspective view of the prosthetic foot blade of FIG. 60 with the sole plate of FIG. 61 partially secured thereto.

FIG. 61 is a front perspective view of a traction system 2212 for the prosthetic foot blade 10. The traction system 2212 includes a sole plate 2214 configured to secure to the prosthetic foot blade 10 of FIG. 60. The sole plate 2214 has externally-threaded posts 2235 extending from the top side 2229 of the sole plate 1014. Additionally, internally-threaded knobs 2216 are retained by tethers 2218 near each post 2235. The posts 2235 are spaced apart from one another in like spacing as the through holes 2213A, 2213B so that the posts 2235 extend through the through holes 2213A, 2213B when the sole plate 2214 is positioned at the bottom side 27 of the prosthetic foot blade 10 with a distal end 2236 of the sole plate 2214 aligned with the distal end 38 of the prosthetic foot blade 10. Alternatively, the distal end 2236 could be configured with a toe cap like toe cap 36 to fit over the distal end 38. The elongated through holes 2213B ease fitting of the sole plate 2214 to the prosthetic foot blade 10 given the curvature of the prosthetic foot blade 10 and the length of the posts 2235. FIG. 62 shows two of the four knobs 2216 threaded to respective posts 2235. When the knobs 2216 are threaded to their respective posts 2235, the sole plate 2214 is secured to the prosthetic foot blade 10 and is pulled against the bottom side 27 of the prosthetic foot blade 10.

Figure 63:
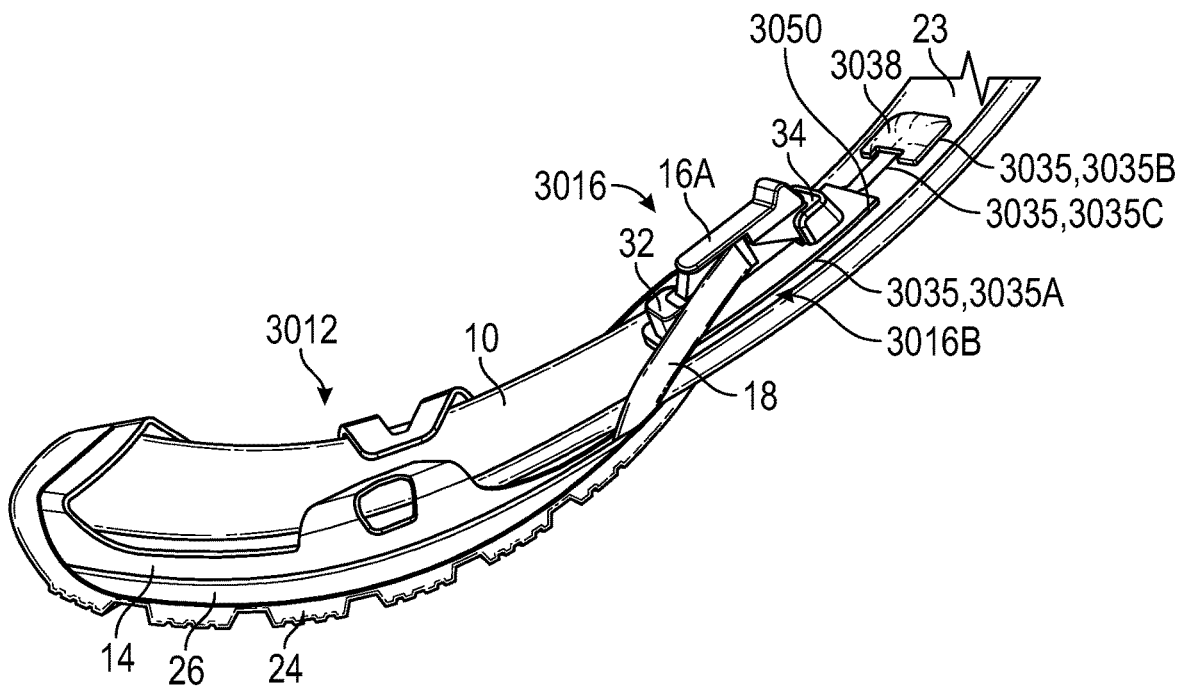
FIG. 63 is a fragmentary perspective view of a prosthetic foot blade shown in fragmentary view and in an unloaded state, and a traction system coupled to the prosthetic foot blade including an alternative latch assembly in a latched state.

FIG. 63 is a fragmentary perspective view of the prosthetic foot blade 10 shown in fragmentary view and in an unloaded state, and a traction system 3012 coupled to the prosthetic foot blade 10 via the strap 18 and an alternative latch assembly 3016. The traction system 3012 includes the sole plate 14, outsole 24, and midsole 26 as described herein. The alternative latch assembly 3016 is the same as latch assembly 16 of FIG. 2 except that an alternative latch mount 3016B is used in place of latch mount 16B and has an alternative latch base 3035 used in place of latch base 35. Because the latch base 3035 is disposed on the top side 23 of the prosthetic foot blade 10, it will be in compression when the prosthetic foot blade 10 experiences longitudinal bending during dynamic loading. This configuration of a latch base 3035 can flex in response to the compressive forces of the prosthetic foot blade 10, such as when a wearer is moving forward with the prosthetic foot blade 10 in contact with a ground surface, reducing the resistance to compression and associated shear forces on the latch base 3035 in comparison to a latch base 35 or another latch base of uniform width and/or flexibility along its length and of the same overall length.

Figure 64:
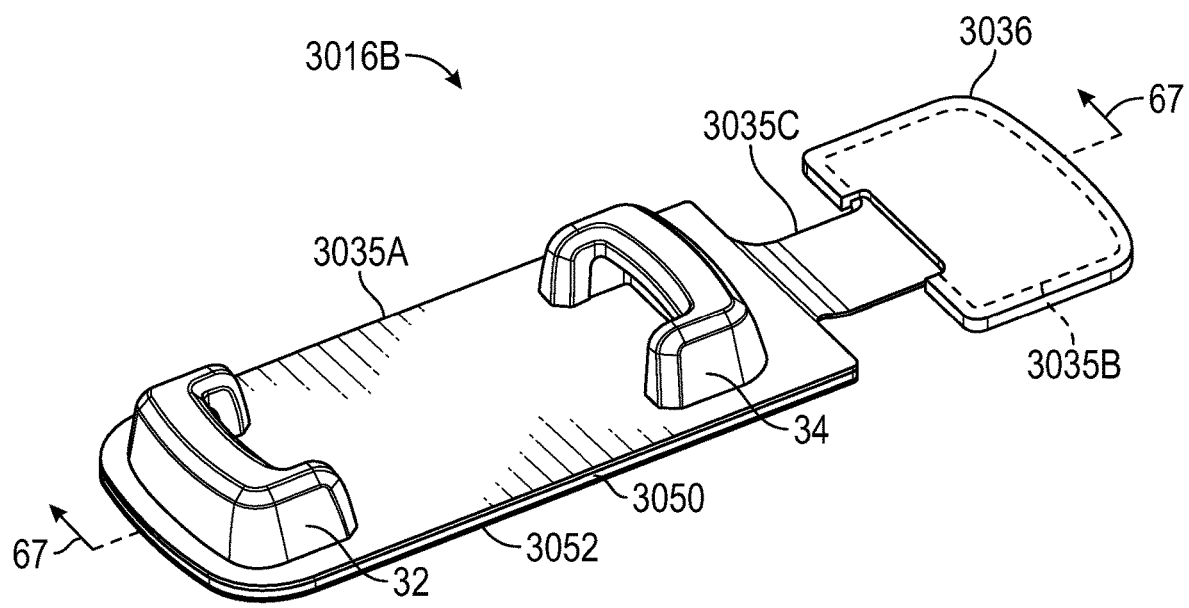
FIG. 64 is a perspective view of a latch mount of the latch assembly of FIG. 63 including a cover over an anchor portion of a latch base.

FIG. 64 is a perspective view of the latch mount 3016B. The latch base 3035 includes a plate portion 3035A, an anchor portion 3035B, and a hinge portion 3035C flexibly connecting the plate portion 3035A and the anchor portion 3035B. A cover 3036 (not shown in FIG. 63) covers the anchor portion 3035B for aesthetic purposes to hide adhesive 3038 (shown in FIG. 63) that may be applied to and mechanically secure the anchor portion 3035B to the prosthetic foot blade 10 as discussed herein.

The front and rear catches 32, 34 are secured to the plate portion 3035A via fasteners extending through fastener openings 114 (shown in FIG. 69) as described with respect to FIGS. 13 and 14. FIG. 69 shows the fastener openings 114 and alignment features 116B in the plate portion 3035A.

As shown in FIG. 63, the hinge portion 3035C extends rearward from the plate portion 3035A over the top side 23 of the prosthetic foot blade 10, and the anchor portion 3035B is disposed rearward of the hinge portion 3035C. The anchor portion 3035B is fixed relative to the top side 23 of the prosthetic foot blade 10 with adhesive 3038, as discussed herein, to mechanically secure the latch base 3035 to the prosthetic foot blade 10. The hinge portion 3035C is disposed above and is unfixed to the top side 23 of the prosthetic foot blade 10. In the example shown, the hinge portion 3035C is only a single strip connecting the plate portion 3035A and the anchor portion 3035B.

As shown in FIG. 69, the hinge portion 3035C is narrower than the plate portion 3035A and also narrower than the anchor portion 3035B. For example, the hinge portion 3035C has a width W1, the plate portion 3035A has width W2, and the anchor portion 3035B has width W3. Both widths W2 and W3 are greater than width W1, where widths are measured along the transverse axis T, perpendicular to the longitudinal axis L. Additionally, the anchor portion 3035B has a length L1 that is shorter than the length L2 of the plate portion 3035A, and both of which are less than the overall length L3 of the latch base 35.

The latch base 3035 may comprise a composite material, such as at least one of a carbon fiber composite, a glass fiber composite, or a carbon-glass fiber composite. In the example shown, the latch base 3035 comprises layers of composite material, with fewer layers at the hinge portion 3035C than at the plate portion 3035A and/or than at the anchor portion 3035B, at least partially accounting for its greater flexibility than the plate portion 3035A and/or the anchor portion 3035B. For example, the latch base 3035 may comprise at least one layer of composite sheet material at the hinge portion 3035C, and a greater number of layers of composite sheet material at the anchor portion 3035B and at the plate portion 3035A. Referring to FIG. 67, a single sheet 3039 of the composite sheet material may extend in each of the plate portion 3035A, the hinge portion 3035C, and the anchor portion 3035B, while additional layers 3041, 3042 of composite sheet material may be attached to the single sheet 3039 at the plate portion 3035A and at the anchor portion 3035B on the top side, the bottom side, or on both the top side and the bottom side of the single sheet 3039. FIG. 67 schematically represents the single sheet 3039, and additional layers 3041 and 3042.

These features enable the hinge portion 3035C to be relatively flexible and soft and enable relative movement of the plate portion 3035A and the anchor portion 3035B (by folding of the hinge portion 3035C, for example), and prevent compressive forces applied by the flexing prosthetic foot blade 10 from extending entirely through the latch base 3035 from the front of the plate portion 3035A to the rear of the anchor portion 3035B.

Figure 65:
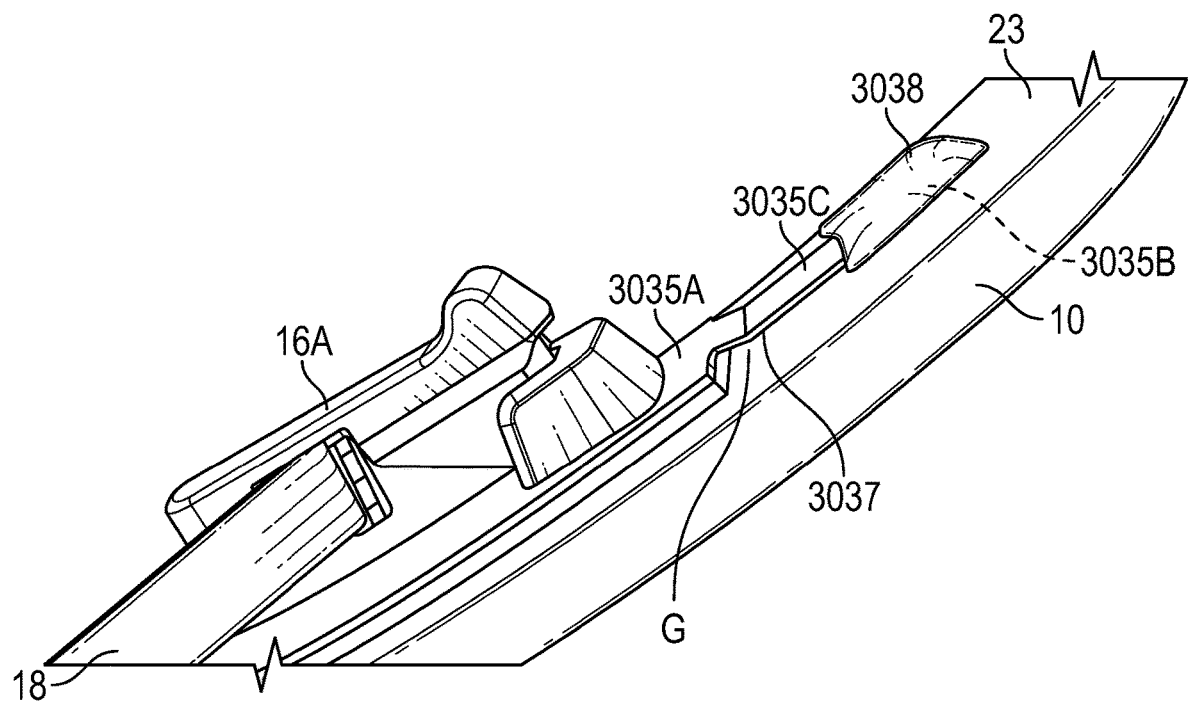
FIG. 65 is a fragmentary perspective view of the prosthetic foot blade and latch assembly of FIG. 63, with the prosthetic foot blade in a relatively unloaded state.
Figure 66:
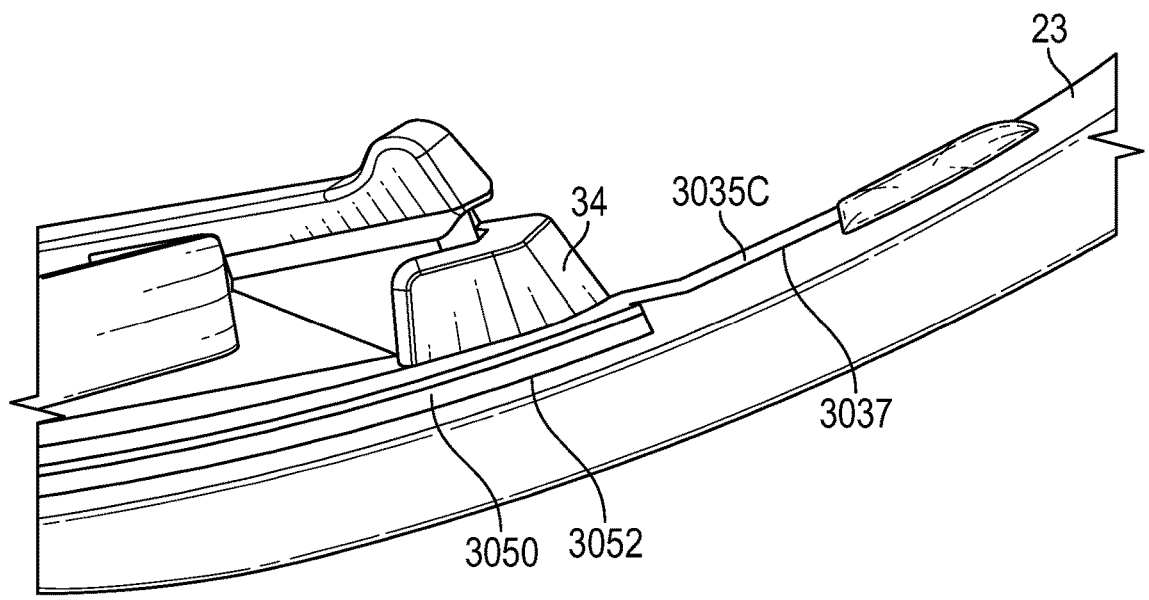
FIG. 66 is a fragmentary perspective view of the prosthetic foot blade and latch assembly of FIG. 63, with the prosthetic foot blade in a relatively loaded state.

FIG. 65 is a fragmentary perspective view with the prosthetic foot blade 10 in a relatively unloaded state, and FIG. 66 is a fragmentary perspective view with the prosthetic foot blade 10 in a relatively loaded state. For example, relatively unloaded state may be when worn by a wearer who is standing still, and the relatively loaded state may be when the wearer is moving forward with the prosthetic foot blade 10 in contact with a ground surface, resulting in higher loads. As shown in FIG. 65, the hinge portion 3035C is at least partially spaced apart from the top side 23 of the prosthetic foot blade 10 when the prosthetic foot blade 10 is in the relatively unloaded state. More specifically, a gap G exists between at least part of the bottom side 3037 of the hinge portion 3035C and the top side 23 of the prosthetic foot blade 10 in the relatively unloaded state of FIG. 65. The hinge portion 3035C flexes to move from being spaced apart by the gap G and into contact with the top side 23 of the prosthetic foot blade 10 in the relatively loaded state of FIG. 66 (e.g., the gap G disappears along the part of the bottom side 3037 that was spaced apart in FIG. 65). The hinge portion 3035C may still be spaced apart from the top side 23 immediately adjacent to the plate portion 3035A due to a height difference of the plate portion 3035A above the top side 23 (which may be due to the additional layers at the plate portion 3035A and/or due to a compressible layer 3050 discussed herein).

FIG. 67 is a cross-sectional view taken at lines 67-67 in FIG. 64 showing the latch base 3035, a compressible layer 3050 disposable between the plate portion 3035A and the top side 23 of the prosthetic foot blade 10, a double-sided adhesive layer 3052, such as double-sided adhesive tape 3052 secured to the bottom side 3055 of the compressible layer 3050 and securable to the top side 23 of the prosthetic foot blade 10 (see FIG. 66), the catches 32, 34, and the cover 3036.

FIG. 68 is an exploded view of a portion of the latch mount 3016B of FIG. 67, showing the latch base 3035, the compressible layer 3050, and the double-sided adhesive tape 3052 of FIG. 67. The compressible layer 3050 is secured to the bottom side 3040 of the plate portion 3035A and is disposed at the top side 23 of the prosthetic foot blade 10 when the latch base 3035 is secured to the prosthetic foot blade 10. For example, the compressible layer 3050 may comprise foam. The compressible layer 3050 allows the plate portion 3035A to effectively float above the top side 23 of the prosthetic foot blade 10 as the compressible layer 3050 can resiliently compress during longitudinal bending of the prosthetic foot blade 10, minimizing the compressive force of the prosthetic foot blade 10 transferred to the plate portion 3035A.

In another example, no double-sided adhesive tape 3052 or other adhesive fasteners or other securing features secure the compressible layer 3050 to the top side 23, with only the tensioned strap 18 holding the compressible layer 3050 against the top side 23. The compressible layer 3050 is thus unfixed to the prosthetic foot blade 10 in such an example, but held against the top side 23 by tension in the strap 18 when the lever 16A is latched to the latch mount 3016B. In still another example, instead of double-sided adhesive tape 3052, adhesive (such as liquid adhesive) may be applied between the top side 23 of the prosthetic foot blade 10 and the bottom side 3055 of the compressible layer 3050.

Because the compressible layer 3050 is not secured to and does not extend under the hinge portion 3035C, the plate portion 3035A is spaced further above the top side 23 than the hinge portion 3035C, creating a bend 3058. The bend 3058 may be referred to as a pre-bend, as it exists even when the prosthetic foot blade 10 is in the relatively unloaded state. The bend 3058 encourages flexing of the latch base 3035 to occur at the bend 3058 during dynamic loading of the prosthetic foot blade 10.

FIG. 69 is a plan view of the latch base 3035 of FIG. 68. The latch base 3035 includes through holes 3060 extending through the anchor portion 3035B. Referring to FIGS. 65 and 67, the adhesive 3038 extends on the top side 23 of the prosthetic foot blade 10 under the anchor portion 3035B, through the anchor portion 3035B at the through holes 3060, and over at least a portion of a top surface 3062 of the anchor portion 3035B when the latch base 3035 is secured to the prosthetic foot blade 10. Adhesive 3038 also extends on the bottom side 3043 of the latch base 3035 at the anchor portion 3035B (e.g., between the anchor portion 3035B and the top side 23 of the prosthetic foot blade 10). With the adhesive 3038 extending not only between the bottom side 3043 of the latch base 3035 and the top side 23 of the prosthetic foot blade 10, but also through the latch base 3035 and onto the top surface 3062 of the latch base 3035, the adhesive 3038 serves as a mechanical attachment, such as a fastener.

Figure 72:
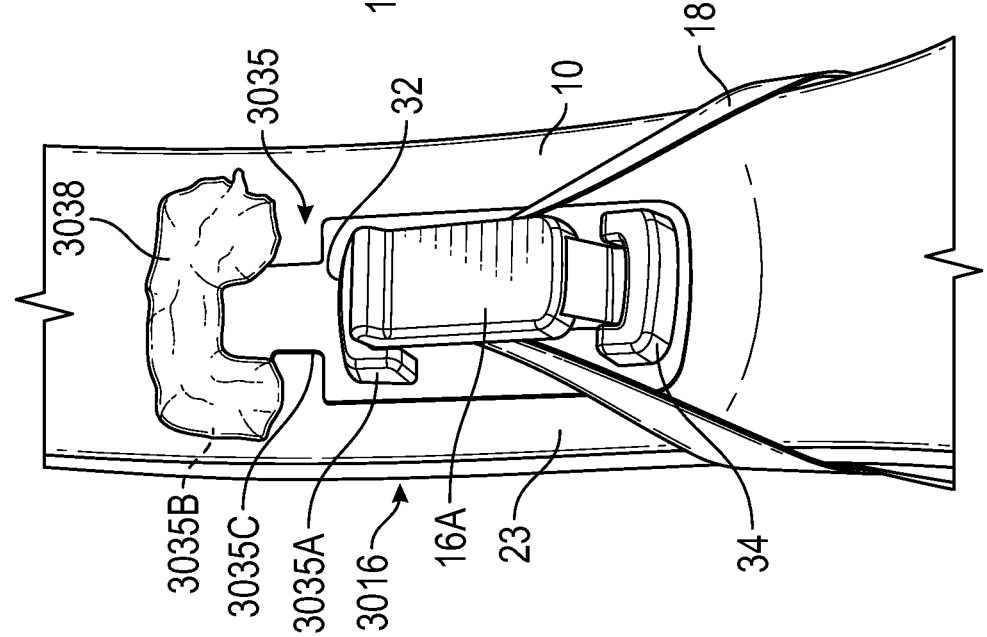
FIG. 72 is a fragmentary perspective view of the prosthetic foot blade and traction system of FIG. 63 with the latch assembly in a latched position and including adhesive in a first arrangement mechanically securing the anchor portion of the latch base to the prosthetic foot blade.

Referring to FIGS. 69 and 72, in another aspect, the adhesive 3038 may further extend around one or more outer edges 3066, 3068, and 3070 of the anchor portion 3035B, such as around a top edge 3066 and side edges 3068, 3070 (shown in FIG. 69 and covered by the adhesive 3038 in FIG. 72), the adhesive 3038 therefore forming a three-sided or T-stop. The adhesive 3038 serves as a mechanical end stop at the outer edges 3066, 3068, 3070 of the anchor portion 3035B. Additionally, the adhesive 3038 may extend over a top surface 3062 of the anchor portion 3035B, and may connect with the adhesive 3038 around the edges 3066, 3068, 3070. FIG. 72 is a fragmentary perspective view of the prosthetic foot blade 10 including adhesive 3038 in a first arrangement mechanically securing the anchor portion 3035B to the prosthetic foot blade 10.

Non-limiting examples of adhesive 3038 described herein include polyurethane adhesive and epoxy adhesive. For example, any of 3M™ Scotch-Weld™ Urethane Adhesive DP640, 3M™ Scotch-Weld™ Epoxy Adhesive DP420, or 3M™ Scotch-Weld™ Epoxy Adhesive DP125 may be used and are available from 3M Company of Saint Paul, Minn. USA.

Figure 73:
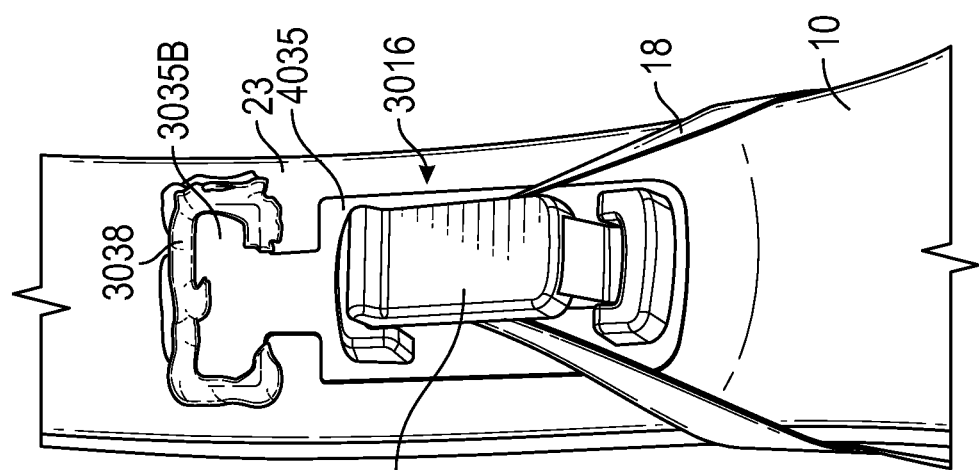
FIG. 73 is a fragmentary perspective view of the prosthetic foot blade and traction system of FIG. 63 including the alternative latch base of FIG. 70 with the latch assembly in a latched position and including adhesive in a second arrangement mechanically securing the anchor portion of the latch base to the prosthetic foot blade.

FIG. 70 is a plan view of an alternative latch base 4035 for the latch assembly 3016 of FIG. 63. The alternative latch base 4035 is alike in all aspects to latch base 3035, except that there are no through holes 3060. To secure the anchor portion 3035B of the latch base 4035 to the top side 23 of the prosthetic foot blade 10, adhesive 3038 may be disposed on the top side 23 along one or more outer edges of the anchor portion 3035B, such as a rear edge 3066 (also referred to as a top edge 3066) of the anchor portion 3035B rearward of the rear catch 34, as well as along the side edges 3068, 3070. The outer edges 3066, 3068, and 3070 shown in FIG. 70 are covered by the adhesive 3038 in FIG. 73, which is a fragmentary perspective view of the prosthetic foot blade 10 including the adhesive 3038 in a second arrangement mechanically securing the anchor portion 3035B to the prosthetic foot blade 10.

Figure 74:
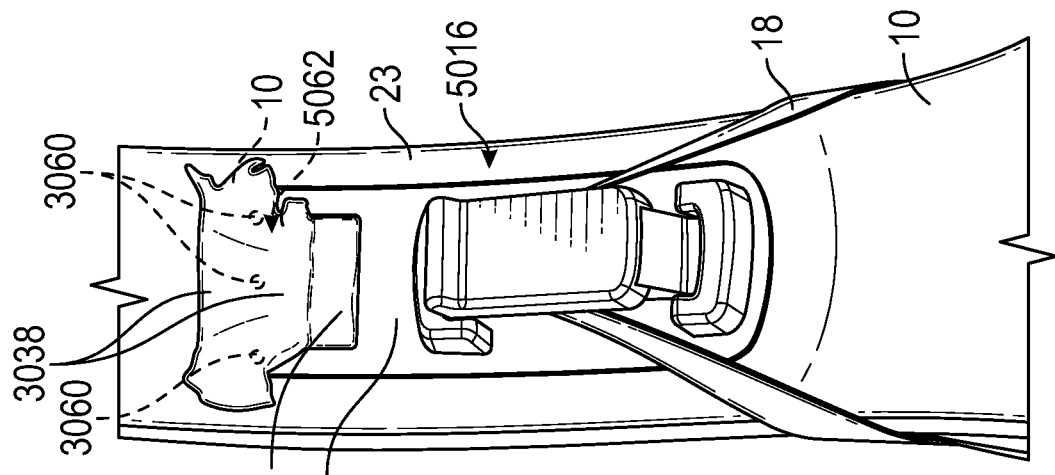
FIG. 74 is a fragmentary perspective view of the prosthetic foot blade and traction system of FIG. 63 including the alternative latch base of FIG. 71 with the latch assembly in a latched position and including adhesive mechanically securing the anchor portion of the latch base to the prosthetic foot blade.

FIG. 71 is a plan view of an alternative latch base 5035 for a latch assembly 5016 shown in FIG. 74, that is the same as the latch assembly 3016 of FIG. 63 except with an alternative latch base 5035. Instead of hinge portion 3035C configured as a single strip, the latch base 5035 has a hinge portion 5035C that includes two strips 5035C1 and 5035C2 spaced transversely apart from one another and connecting the plate portion 3035A and the anchor portion 3035B. An aperture 5068 is formed between and spaces apart the strips 5035C1 and 5035C2. Through holes 3060 like those of FIG. 67 may extend through the anchor portion 3035B. The through holes 3060 may be the same number as in the latch base 3035, or may be a greater number. Through holes 3060 are not shown in FIG. 71, but are added in FIG. 74, which shows the latch base 5035 secured to the top side 23 of the prosthetic foot blade 10 with adhesive 3038.

The adhesive 3038 is applied to and extends between the bottom side of the latch base 5035 and the top side 23 of the prosthetic foot blade 10, through the through holes 3060 of the latch base 5035 and onto the top surface 5062 of the latch base 5035. The adhesive 3038 also extends around the outer edges 3066, 3068, 3070, and 5072 of the anchor portion 3035B, such as around the top edge 3066, side edges 3068, 3070, and an edge 5072 at the aperture 5068 (shown in FIG. 71 and covered by the adhesive 3038 in FIG. 74). The adhesive 3038 therefore forms a four-sided stop and serves as a mechanical attachment, such as a fastener.

Figure 75:
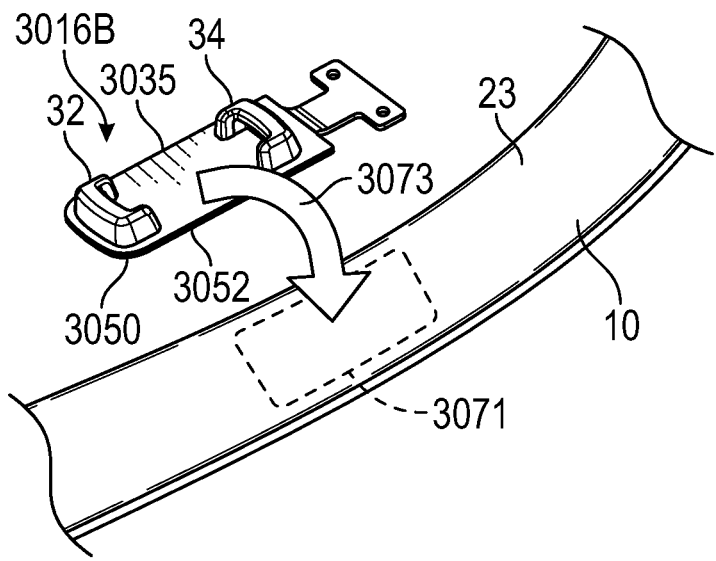
FIG. 75 is a schematic perspective fragmentary view of the prosthetic foot blade of FIG. 63 and the latch mount of FIGS. 67 and 68, showing a step of placing the latch mount at the prosthetic foot blade.

FIG. 75 is a schematic perspective fragmentary view of the prosthetic foot blade 10, showing a step of placing the latch mount 3016B at a location 3071 on the top side 23 of the prosthetic foot blade 10. For example, the latch mount 3016B is moved adjacent to the prosthetic foot blade 10 as indicated by arrow 3073 so that the double-sided adhesive tape 3052 is disposed on the top side 23 at the location 3071.

Figure 76:
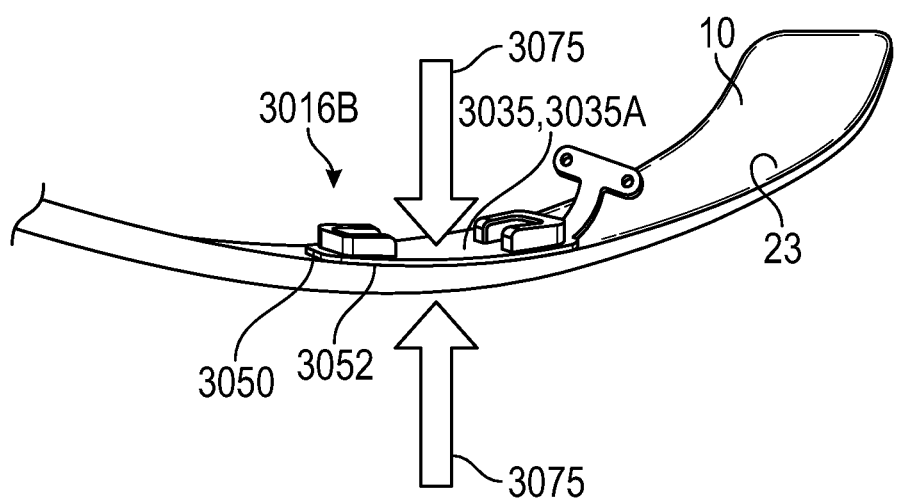
FIG. 76 is a schematic perspective fragmentary view of the prosthetic foot blade of FIG. 63 showing another step of securing the latch mount of FIG. 75 to the prosthetic foot blade by pressing the adhesive tape against the foot blade.

FIG. 76 is a schematic perspective fragmentary view of the prosthetic foot blade 10 showing another step of securing the latch mount 3016B to the prosthetic foot blade 10 by pressing the latch mount 3016B and the prosthetic foot blade 10 together, as shown by arrows 3075, thereby pressing the double-sided adhesive tape 3052 against the top side 23 of the prosthetic foot blade 10.

Figure 77:
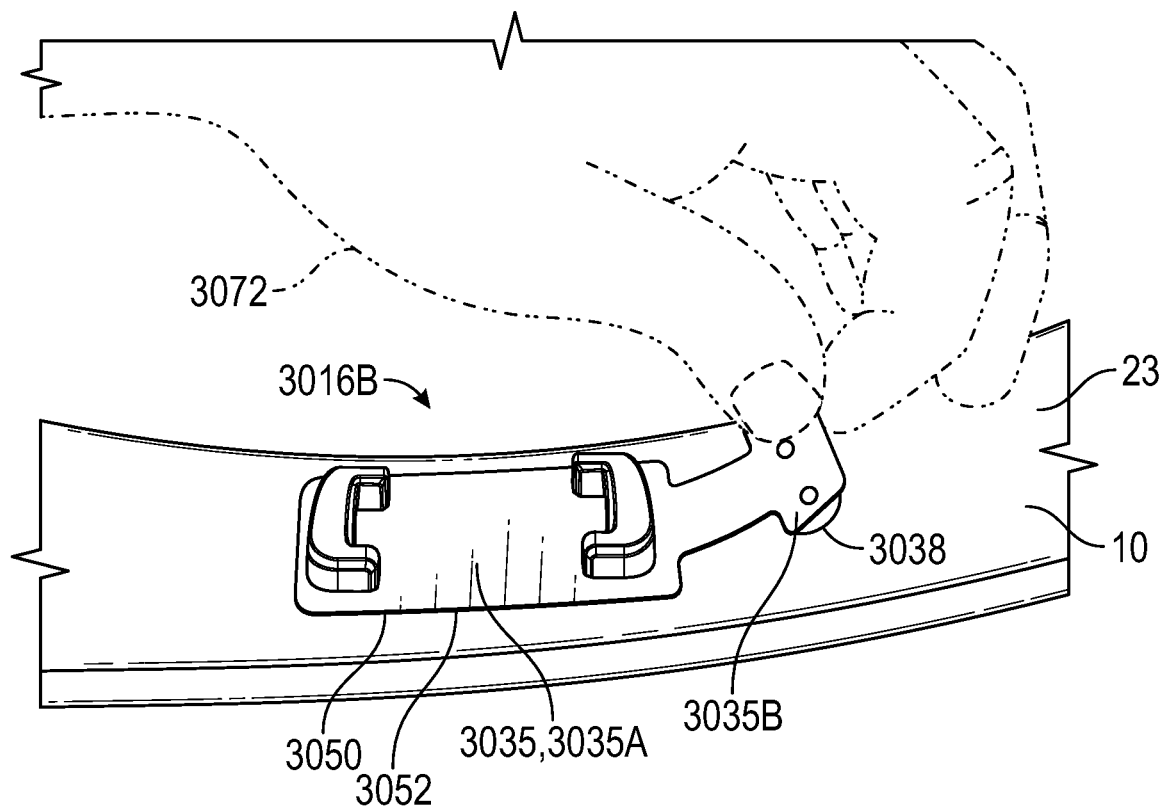
FIG. 77 is a schematic perspective fragmentary view of the prosthetic foot blade of FIG. 63 showing another step of securing the latch mount of FIG. 75 to the prosthetic foot blade by mechanically securing the anchor portion of the latch body to the prosthetic foot blade with adhesive, with a hand shown in phantom.

FIG. 77 is a schematic perspective fragmentary view of the prosthetic foot blade 10 showing another step of securing the latch mount 3016B to the prosthetic foot blade 10 by mechanically securing the anchor portion 3035B of the latch base 3035 to the prosthetic foot blade 10 with adhesive 3038 disposed on the bottom side of the anchor portion 3035B to be disposed on the top side 23 of the prosthetic foot blade 10 as discussed herein, with a hand 3072 shown in phantom.

Figure 78:
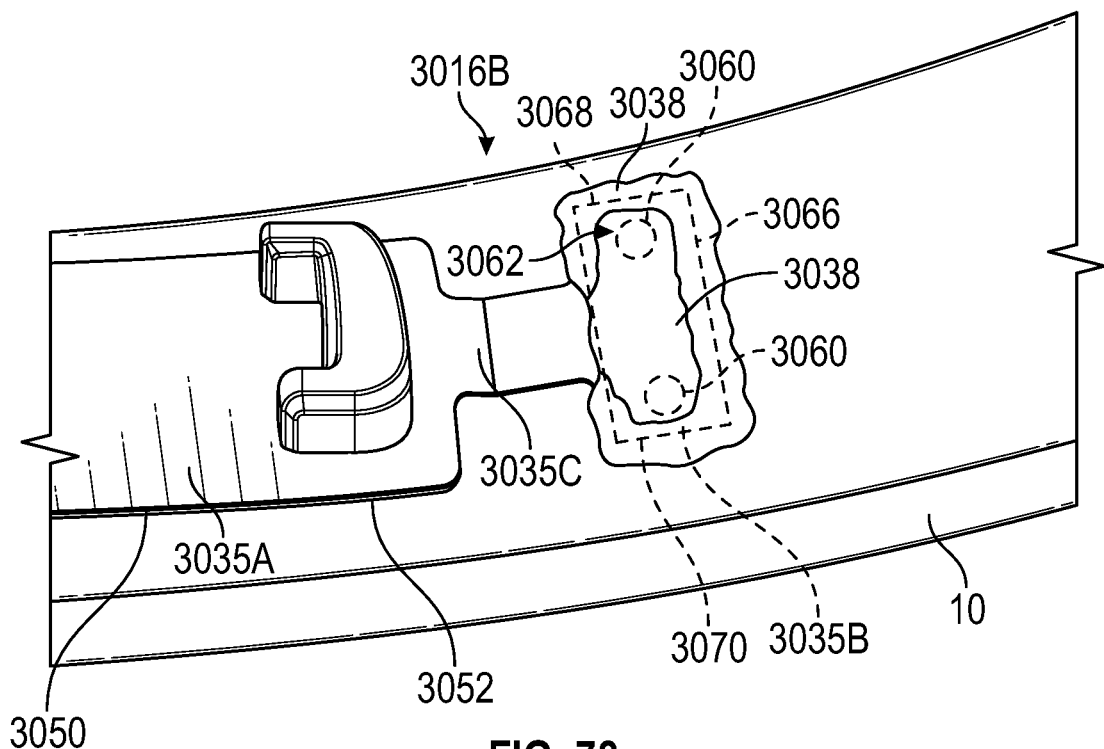
FIG. 78 is a schematic perspective fragmentary view of the prosthetic foot blade of FIG. 63 showing another step of securing the latch mount of FIG. 75 to the prosthetic foot blade by further mechanically securing the anchor portion of the latch body to the prosthetic foot blade by disposing adhesive along edges of the anchor portion.

FIG. 78 is a schematic perspective fragmentary view of the prosthetic foot blade 10 showing another step of securing the latch mount 3016B to the prosthetic foot blade 10 by further mechanically securing the anchor portion 3035B of the latch base 3035 to the prosthetic foot blade 10 by disposing adhesive 3038 along the outer edges 3066, 3068, and 3070 of the anchor portion 3035B. The adhesive 3038 placed on the bottom side of the anchor portion 3035B also extends through the through holes 3060 onto the top surface 3062 and/or additional adhesive 3038 may be placed on the top surface 3062.

Figure 79:
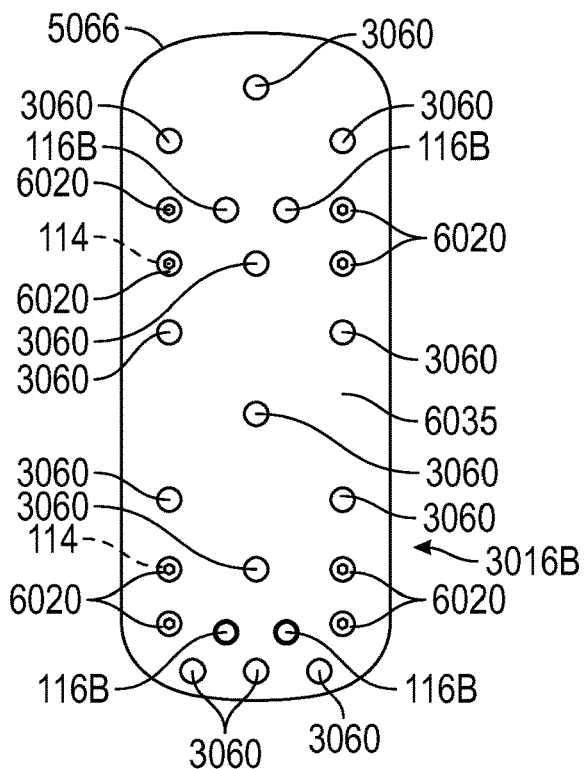
FIG. 79 is a plan view of an alternative latch base for a latch assembly of FIG. 80.
Figure 80:
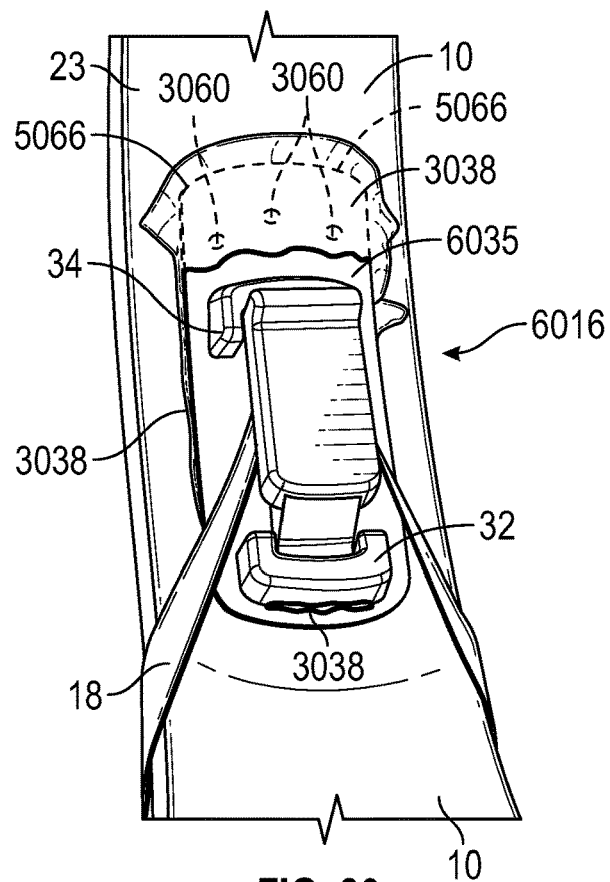
FIG. 80 is a fragmentary perspective view of the prosthetic foot blade and traction system of FIG. 63 including a latch assembly in a latched position with the alternative latch base of FIG. 79 secured to the prosthetic foot blade.

FIG. 79 is a plan view of the bottom side of an alternative latch base 6035 for a latch assembly 6016 that is the same as the latch assembly 16 of FIG. 2 except with the latch base 6035 replacing the latch base 35. The latch base 6035 is a flat plate identical to latch base 35 of FIG. 14, except with added through holes 3060. Fasteners 6020 are disposed at the fastener openings 114 (only some of which are labeled). The catches 32, 34 are fastened to the latch base 6035 at the fastener openings 114 by the fasteners 6020 and are indicated in FIG. 80. Some of the through holes 3060 are disposed forward of the front catch 32 and some of the through holes are disposed rearward of the rear catch 34.

Adhesive 3038 is disposed at the bottom side of the latch base 6035 (e.g., between the latch base 6035 and the top side 23 of the prosthetic foot blade 10). The adhesive 3038 extends through the through holes 3060 to the top side of the latch base 6035. Adhesive 3038 is also disposed around an outer edge 5066 of the latch base 6035 as shown in FIG. 80, rearward of the rear catch 34. Adhesive 3038 disposed in these positions mechanically secures the latch base 6035 to the prosthetic foot blade 10 and acts as a mechanical stop. Accordingly, by adding the through holes 3060 and adhesive 3038 as described, the flat plate latch base 6035 better withstands the compressive forces due to dynamic loading of the prosthetic foot blade 10.

Figure 81:
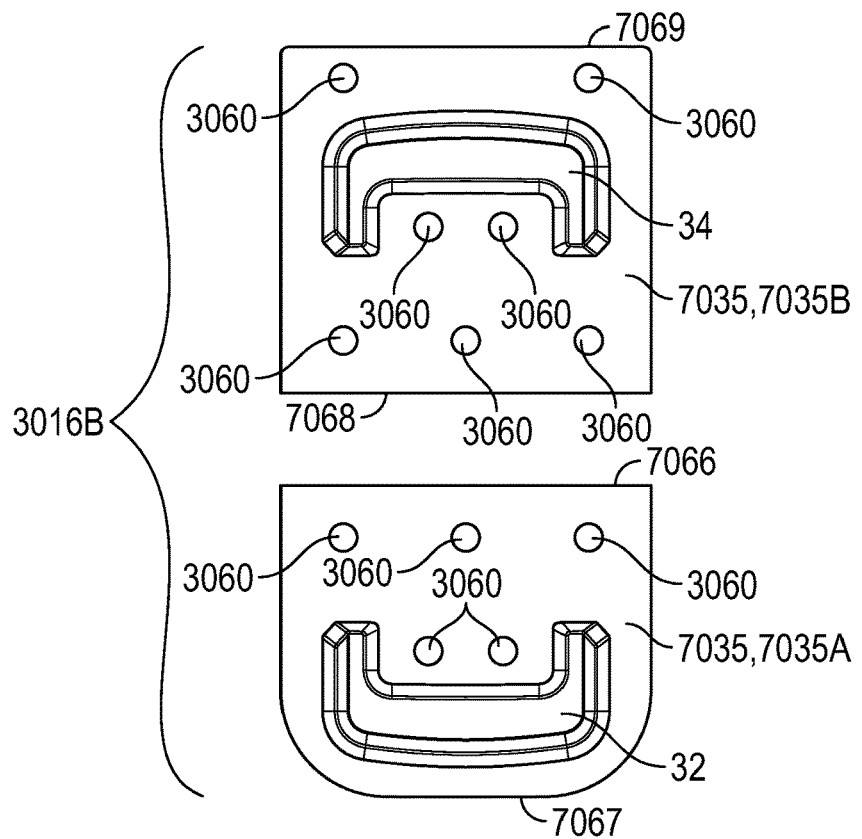
FIG. 81 is a plan view of an alternative latch mount for a latch assembly of FIG. 82 including a split latch base shown with the front and rear catches.
Figure 82:
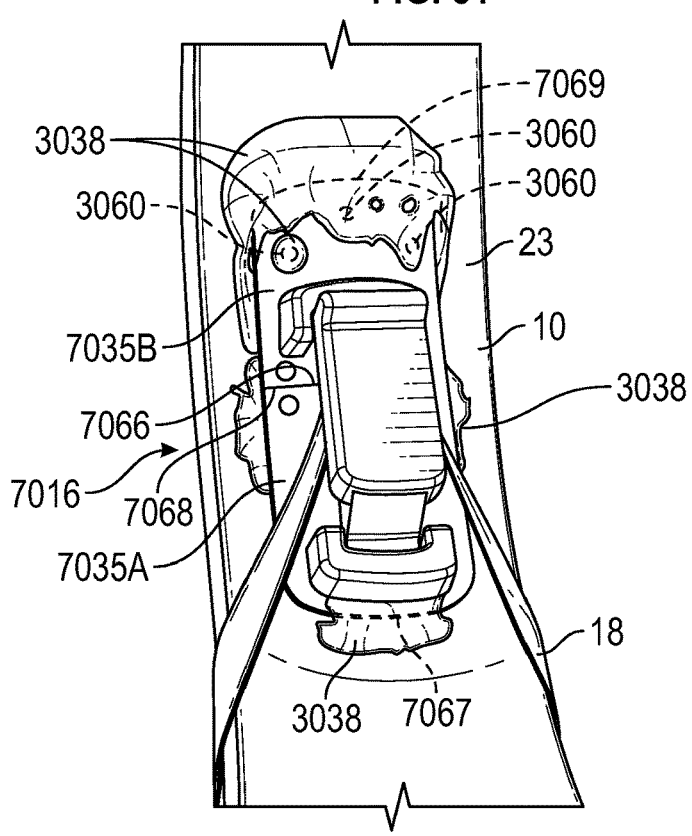
FIG. 82 is a fragmentary perspective view of the prosthetic foot blade and traction system of FIG. 63 with a latch assembly in a latched position with the alternative latch base of FIG. 81 secured to the prosthetic foot blade.

FIG. 81 is a plan view of an alternative latch base 7035 for a latch assembly 7016 shown in FIG. 82. The latch assembly 7016 is the same as latch assembly 16 of FIG. 2 except for the alternative latch base 7035 replacing latch base 35. The latch base 7035 is referred to as a split latch base because it includes a front section 7035A and a rear section 7035B, with a rear edge 7066 of the front section 7035A physically split from a front edge 7068 of the rear section 7035B. Sectioning the latch base 7035 with a transverse split lessens the length along the prosthetic foot blade 10 along which each section of the latch base 7035 extends. Although the overall length of the latch base 7035 may be the same as if there was no transverse split (e.g., as if the sections 7035A, 7035B were unitary), a shorter section is subjected to lower compressive forces than would be a longer section during dynamic loading of the prosthetic foot blade 10, for example. The latch base 7035 also includes a plurality of through holes 3060.

FIG. 82 is a fragmentary perspective view of the prosthetic foot blade 10 and the latch assembly 7016 in a latched position and including the alternative latch base 7035. The sections 7035A, 7035B are adhered to the top side 23 of the prosthetic foot blade 10 with the edges 7066, 7068 abutting as shown. Alternatively, the edges 7066 and 7068 may be slightly spaced apart from one another. Adhesive 3038 is disposed at the bottom side of the latch base 7035 (e.g., between the sections 7035A, 7035B and the top side 23 of the prosthetic foot blade 10), and extends through the through holes 3060 to the top side of the sections 7035A, 7035B, mechanically securing the latch base 7035 to the prosthetic foot blade 10. Adhesive 3038 is also disposed around a front edge 7067 of the latch base 7035 forward of the front catch 32 and around a rear edge 7069 of the latch base 7035 rearward of the rear catch 34. The adhesive 3038 creates mechanical stops at the edges 7067 and 7069, as shown in FIG. 82.

The following Clauses provide example configurations of a prosthetic blade traction system disclosed herein.

Clause 1. A traction system for an ambulatory support, the traction system comprising: a sole plate couplable to a distal end of the ambulatory support to extend under a bottom side of the ambulatory support; a latch assembly including: a front catch and a rear catch both fixable at a top side of the ambulatory support with the front catch nearer to the distal end of the ambulatory support than the rear catch, and a lever having a front end and a rear end, the front end releasably latchable to the front catch and the rear end releasably latchable to the rear catch when the lever is pivoted about the latched front end; and a strap secured to the lever and to the sole plate and placed in tension when the sole plate is coupled to the distal end of the ambulatory support and the lever is latched at the front end and the rear end, the strap pulling the sole plate against the distal end and the bottom side of the ambulatory support.

Clause 2. The traction system of clause 1, wherein the strap extends through the lever between the front end and the rear end.

Clause 3. The traction system of any of clauses 1-2, further comprising: at least one sole layer secured at the bottom side of the sole plate and including a ground-engaging traction surface; and wherein the strap is secured to the bottom side of the sole plate between the sole plate and the at least one sole layer.

Clause 4. The traction system of any of clauses 1-3, wherein the sole plate has a front wall disposed forward of the distal end of the ambulatory support and a toe cap extending rearward from the front wall over the top side of the ambulatory support when the sole plate is coupled to the ambulatory support.

Clause 5. The traction system of any of clauses 1-4, wherein a bottom wall of the sole plate is sufficiently flexible to move from a relatively flat state to a relatively curved state to conform with a curvature of the bottom side of the ambulatory support when the strap is placed in tension.

Clause 6. The traction system of any of clauses 1-5, wherein the front catch defines a front pocket opening toward the rear catch and the rear catch defines a rear pocket opening toward the front catch; and the front end of the lever includes a front lip captured in the front pocket when the front end latches to the front catch and the rear end of the lever includes a rear lip captured in the rear pocket when the rear end latches to the rear catch.

Clause 7. The traction system of any of clauses 1-6, wherein the lever includes: a first latch body including the front end of the lever; a second latch body coupled to the first latch body and including the rear end of the lever; and a biasing member engaging the first latch body and the second latch body and biasing the front end apart from the rear end, the front end movable toward the rear end to release the lever from the rear catch under a force opposing a force of the biasing member.

Clause 8. The traction system of clause 7, wherein the first latch body includes an intermediate wall disposed rearward of the front end, the second latch body includes a protrusion disposed between the front end and the intermediate wall, the biasing member is disposed between the rear end and the intermediate wall and forces the intermediate wall against the protrusion.

Clause 9. The traction system of clause 7, wherein: the first latch body includes side walls; the second latch body includes side walls disposed adjacent to the side walls of the first latch body; and the side walls of one of the first latch body and the second latch body include flanges, and the side walls of the other of the first latch body and the second latch body include slots, and the flanges fit within the slots.

Clause 10. The traction system of any of clauses 1-9, further comprising: an adjustment screw extending longitudinally within the lever and interfacing with the strap; and wherein a position of the adjustment screw is adjustable to adjust tension in the strap when the lever is latched at the front end and the rear end.

Clause 11. The traction system of any of clauses 1-10, wherein: the latch assembly further includes a latch base securable to the top side of the ambulatory support; and the front and rear catches are secured to the latch base.

Clause 12. The traction system of clause 11, wherein a portion of the latch base extends forward of the front catch along the top side of the ambulatory support.

Clause 13. The traction system of clause 11, wherein: the latch base includes a plate portion, an anchor portion, and a hinge portion flexibly connecting the plate portion and the anchor portion; the front and rear catches are secured to the plate portion; the anchor portion is fixed relative to the top side of the ambulatory support, and the hinge portion is unfixed to the top side of the ambulatory support when the latch base is secured to the ambulatory support.

Clause 14. The traction system of clause 13, wherein: the hinge portion is at least partially spaced apart from the top side of the ambulatory support when the ambulatory support is in relatively unloaded state and, optionally, is in contact with the top side of the ambulatory support as the ambulatory support flexes in a relatively loaded state.

Clause 15. The traction system of any of clauses 13-14, wherein the hinge portion extends rearward from the plate portion over the top side of the ambulatory support, and the anchor portion is disposed rearward of the hinge portion when the latch base is secured to the ambulatory support.

Clause 16. The traction system of any of clauses 13-15, further comprising: a compressible layer secured to a bottom side of the plate portion and disposed at the top side of the ambulatory support when the latch base is secured to the ambulatory support.

Clause 17. The traction system of clause 16, wherein the compressible layer comprises foam.

Clause 18. The traction system of any of clauses 16-17, wherein the compressible layer is unfixed to the top side of the ambulatory support and held against the top side of the ambulatory support by tension in the strap when the lever is latched.

Clause 19. The traction system of any of clauses 16-17, further comprising: a double-sided adhesive layer disposed between the compressible layer and the top side of the ambulatory support and further securing the latch base to the ambulatory support.

Clause 20. The traction system of any of clauses 13-19, wherein the hinge portion is either or both of narrower and thinner than the plate portion and the anchor portion.

Clause 21. The traction system of any of clauses 13-20, wherein the anchor portion is shorter than the plate portion.

Clause 22. The traction system of any of clauses 13-21, wherein the latch base comprises at least one of a carbon fiber composite, a glass fiber composite, or a carbon-glass fiber composite.

Clause 23. The traction system of any of clauses 13-22, wherein the latch base includes at least one layer of composite sheet material at the hinge portion, and a greater number of layers of composite sheet material at the anchor portion and at the plate portion.

Clause 24. The traction system of any of clauses 13-23, wherein the hinge portion comprises only a single strip connecting the plate portion and the anchor portion, or comprises two or more strips spaced transversely apart from one another and connecting the plate portion and the anchor portion.

Clause 25. The traction system of any of clauses 13-24, wherein the anchor portion includes through holes, and further comprising: adhesive extending between the anchor portion and the top side of the ambulatory support, through the through holes, and over at least a portion of a top surface of the anchor portion when the latch base is secured to the ambulatory support.

Clause 26. The traction system of any of clauses 13-25, further comprising: adhesive extending between the anchor portion and the top side of the ambulatory support, and around an outer edge of the anchor portion when the latch base is secured to the ambulatory support.

Clause 27. The traction system of any of clauses 13-26, further comprising: a cover secured over the anchor portion.

Clause 28. The traction system of any of clauses 11-27, wherein the latch base has through holes extending through the latch base, and further comprising: adhesive extending through the through holes, and over at least a portion of a top surface of latch base when the latch base is secured to the ambulatory support.

Clause 29. The traction system of any of clauses 11-28, wherein at least some of the through holes are disposed forward of the front catch and/or at least some of the through holes are disposed rearward of the rear catch.

Clause 30. The traction system of any of clauses 11-29, further comprising: adhesive disposed along a front edge of the latch base forward of the front catch and/or along a rear edge of the latch base rearward of the rear catch when the latch base is secured to the ambulatory support.

Clause 31. The traction system of any of clauses 11-30, wherein the latch base includes a front section and a rear section with a rear edge of the front section split from a front edge of the rear section.

Clause 32. The traction system of any of clauses 1-31, wherein the latch assembly is a spring-loaded, off-center draw latch.

Clause 33. The traction system of any of clauses 1-32, wherein the lever includes a grip protruding at the rear end.

Clause 34. The traction system of any of clauses 1-33, wherein the sole plate defines integral side clamps that extend around opposing sides of the ambulatory support and over the top side of the ambulatory support when the sole plate is coupled to the ambulatory support.

Clause 35. The traction system of any of clauses 1-34, wherein the ambulatory support is one of a prosthetic foot blade or a crutch.

Clause 36. A traction system for an ambulatory support in particular according to any one of the preceding clauses, the traction system comprising: a sole plate couplable to a distal end of the ambulatory support to extend under a bottom side of the ambulatory support; an attachment system including a threaded post extending from the sole plate and a knob securable to an end of the threaded post; wherein the ambulatory support defines a through hole extending through the ambulatory support from the bottom side to a top side of the ambulatory support; and wherein the threaded post extends through the through hole when the sole plate is coupled to the distal end of the ambulatory support, and the sole plate is retained against the bottom side of the ambulatory support when the knob is secured to the threaded post.

Clause 37. The traction system of clause 36, further comprising: a tether secured to the knob and securable to the top side of the ambulatory support to secure the knob to the ambulatory support.

Clause 38. The traction system of clause 36, further comprising: a boss extending from the top side of the ambulatory support; and wherein the through hole extends through the boss with a longitudinal axis of the through hole at an acute angle to the top side of the ambulatory support.

Clause 39. The traction system of clause 36, further comprising: a boss extending from the top side of the ambulatory support; wherein the through hole extends through the boss; and wherein the knob has a flange larger than a knob opening of the boss so that the knob is retained by the boss regardless of whether the knob is secured to the end of the threaded post.

Clause 40. A traction system for an ambulatory support in particular according to any one of the preceding clauses, the traction system comprising: a latch assembly operable to latch a sole plate to a distal end of the ambulatory support, the latch assembly including: a latch base fixable at a top side of the ambulatory support; wherein the latch base includes a plate portion, an anchor portion, and a hinge portion flexibly connecting the plate portion and the anchor portion; and wherein the anchor portion is fixable relative to the top side of the ambulatory support and the hinge portion is disposed above and unfixed to the top side of the ambulatory support when the latch base is secured to the ambulatory support.

Clause 41. The traction system of clause 40, further comprising: a compressible layer disposed between the plate portion and the top side of the ambulatory support when the latch base is secured to the ambulatory support.

Clause 42. The traction system of clause 40 or clause 41, further comprising: a front catch and a rear catch both secured to the plate portion of the latch base with the front catch nearer to the distal end of the ambulatory support than the rear catch; and a lever having a front end and a rear end, the front end releasably latchable to the front catch and the rear end releasably latchable to the rear catch when the lever is pivoted about the latched front end.

To assist and clarify the description of various embodiments, various terms are defined herein. Unless otherwise indicated, the following definitions apply throughout this specification (including the claims). Additionally, all references referred to are incorporated herein in their entirety.

"A", "an", "the", "at least one", and "one or more" are used interchangeably to indicate that at least one of the items is present. A plurality of such items may be present unless the context clearly indicates otherwise. All numerical values of parameters (e.g., of quantities or conditions) in this specification, unless otherwise indicated expressly or clearly in view of the context, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, a disclosure of a range is to be understood as specifically disclosing all values and further divided ranges within the range.

The terms "comprising", "including", and "having" are inclusive and therefore specify the presence of stated features, steps, operations, elements, or components, but do not preclude the presence or addition of one or more other features, steps, operations, elements, or components. Orders of steps, processes, and operations may be altered when possible, and additional or alternative steps may be employed. As used in this specification, the term "or" includes any one and all combinations of the associated listed items. The term "any of" is understood to include any possible combination of referenced items, including "any one of" the referenced items. The term "any of" is understood to include any possible combination of referenced claims of the appended claims, including "any one of" the referenced claims.

For consistency and convenience, directional adjectives may be employed throughout this detailed description corresponding to the illustrated embodiments. Those having ordinary skill in the art will recognize that terms such as "above", "below", "upward", "downward", "top", "bottom", etc., may be used descriptively relative to the figures, without representing limitations on the scope of the invention, as defined by the claims.

The term "longitudinal" refers to a direction extending along a length of a component. The term "forward" or "anterior" is used to refer to the general direction from a rear toward a front of a component or system, and the term "rearward" or "posterior" is used to refer to the opposite direction, i.e., the direction from the front toward the rear. In some cases, a component may be identified with a longitudinal axis as well as a forward and rearward longitudinal direction along that axis. The longitudinal direction or axis may also be referred to as an anterior-posterior direction or axis.

The term "transverse" refers to a direction extending along a width of a component. For example, a transverse direction of a shoe extends between a lateral side and a medial side of the shoe. The transverse direction or axis may also be referred to as a lateral direction or axis or a mediolateral direction or axis.

The term "vertical" refers to a direction generally perpendicular to both the lateral and longitudinal directions. For example, in cases where a sole is planted flat on a ground surface, the vertical direction may extend from the ground surface upward. It will be understood that each of these directional adjectives may be applied to individual components of a sole. The term "upward" or "upwards" refers to the vertical direction toward a top of the component. The term "downward" or "downwards" refers to the vertical direction opposite the upward direction, toward the bottom of a component.

The "inner side" of a component refers to the side or surface of the component that is (or will be) oriented toward the interior of the component or an assembly that includes the component. The "outer side" or "exterior" of a component refers to the side or surface of the component that is (or will be) oriented away from the interior of the component or an assembly including the component. In some cases, other components may be between the inner side of a component and the interior in the assembly. Similarly, other components may be between an outer side of a component and the space external to the assembly. Further, the terms "inward" and "inwardly" refer to the direction toward the interior of the component or assembly, and the terms "outward" and "outwardly" refer to the direction toward the exterior of the component or assembly. In addition, the term "proximal" refers to a direction that is nearer a body part on which a component or assembly is worn or to which it is attached. Likewise, the term "distal" refers to a relative position that is further away from a body part on which the component is worn or to which it is attached. Thus, the terms proximal and distal may be understood to provide generally opposing terms to describe relative spatial positions.

While various embodiments have been described, the description is intended to be exemplary, rather than limiting and it will be apparent to those of ordinary skill in the art that many more embodiments and implementations are possible that are within the scope of the embodiments. Any feature of any embodiment may be used in combination with or substituted for any other feature or element in any other embodiment unless specifically restricted. Accordingly, the embodiments are not to be restricted except in light of the attached claims and their equivalents. Also, various modifications and changes may be made within the scope of the attached claims.

While several modes for carrying out the many aspects of the present teachings have been described in detail, those familiar with the art to which these teachings relate will recognize various alternative aspects for practicing the present teachings that are within the scope of the appended claims. It is intended that all matter contained in the above description or shown in the accompanying drawings shall be interpreted as illustrative and exemplary of the entire range of alternative embodiments that an ordinarily skilled artisan would recognize as implied by, structurally and/or functionally equivalent to, or otherwise rendered obvious based upon the included content, and not as limited solely to those explicitly depicted and/or described embodiments.

What is claimed is:

1. A traction system for an ambulatory support, the traction system comprising:
    a sole plate couplable to a distal end of the ambulatory support to extend under a bottom side of the ambulatory support;
    a latch assembly including:
        a front catch and a rear catch both fixable at a top side of the ambulatory support with the front catch nearer to the distal end of the ambulatory support than the rear catch, and
        a lever having a front end and a rear end, the front end releasably latchable to the front catch and the rear end releasably latchable to the rear catch when the lever is pivoted about the latched front end; and
    a strap secured to the lever and to the sole plate and placed in tension when the sole plate is coupled to the distal end of the ambulatory support and the lever is latched at the front end and the rear end, the strap pulling the sole plate against the distal end and the bottom side of the ambulatory support.

2. The traction system of claim 1, wherein the strap extends through the lever between the front end and the rear end.

3. The traction system of claim 1, further comprising:
    at least one sole layer secured at the bottom side of the sole plate and including a ground-engaging traction surface; and
    wherein the strap is secured to the bottom side of the sole plate between the sole plate and the at least one sole layer.

4. The traction system of claim 1, wherein the sole plate has a front wall disposed forward of the distal end of the ambulatory support and a toe cap extending rearward from the front wall over the top side of the ambulatory support when the sole plate is coupled to the ambulatory support.

5. The traction system of claim 1, wherein the front catch defines a front pocket opening toward the rear catch and the rear catch defines a rear pocket opening toward the front catch; and
    the front end of the lever includes a front lip captured in the front pocket when the front end latches to the front catch and the rear end of the lever includes a rear lip captured in the rear pocket when the rear end latches to the rear catch.

6. The traction system of claim 1, wherein the lever includes:
    a first latch body including the front end of the lever;
    a second latch body coupled to the first latch body and including the rear end of the lever; and
    a biasing member engaging the first latch body and the second latch body and biasing the front end apart from the rear end, the front end movable toward the rear end to release the lever from the rear catch under a force opposing a force of the biasing member.

7. The traction system of claim 6, wherein the first latch body includes an intermediate wall disposed rearward of the front end, the second latch body includes a protrusion disposed between the front end and the intermediate wall, the biasing member is disposed between the rear end and the intermediate wall and forces the intermediate wall against the protrusion.

8. The traction system of claim 7, wherein:
    the first latch body includes side walls;
    the second latch body includes side walls disposed adjacent to the side walls of the first latch body; and
    the side walls of one of the first latch body and the second latch body include flanges, and the side walls of the other of the first latch body and the second latch body include slots, and the flanges fit within the slots.

9. The traction system of claim 1, further comprising:
    an adjustment screw extending longitudinally within the lever and interfacing with the strap; and wherein a position of the adjustment screw is adjustable to adjust tension in the strap when the lever is latched at the front end and the rear end.

10. The traction system of claim 1, wherein:
    the latch assembly further includes a latch base securable to the top side of the ambulatory support; and
    the front and rear catches are secured to the latch base.

11. The traction system of claim 10, wherein:
    the latch base includes a plate portion, an anchor portion, and a hinge portion flexibly connecting the plate portion and the anchor portion;
    the front and rear catches are secured to the plate portion;
    the anchor portion is fixed relative to the top side of the ambulatory support, and the hinge portion is unfixed to the top side of the ambulatory support when the latch base is secured to the ambulatory support.

12. The traction system of claim 11, wherein:
the hinge portion is at least partially spaced apart from the top side of the ambulatory support when the ambulatory support is in relatively unloaded state.

13. The traction system of claim 11, wherein the hinge portion extends rearward from the plate portion over the top side of the ambulatory support, and the anchor portion is disposed rearward of the hinge portion when the latch base is secured to the ambulatory support.

14. The traction system of claim 11, further comprising:
a compressible layer secured to a bottom side of the plate portion and disposed at the top side of the ambulatory support when the latch base is secured to the ambulatory support.

15. The traction system of claim 11, wherein the hinge portion is either or both of narrower and thinner than the plate portion and the anchor portion.

16. The traction system of claim 11, wherein the anchor portion includes through holes, and further comprising:
adhesive extending between the anchor portion and the top side of the ambulatory support, through the through holes, and over at least a portion of a top surface of the anchor portion when the latch base is secured to the ambulatory support.

17. The traction system of claim 11, further comprising:
adhesive extending between the anchor portion and the top side of the ambulatory support, and around an outer edge of the anchor portion when the latch base is secured to the ambulatory support.

18. The traction system of claim 11, further comprising:
a cover secured over the anchor portion.

19. The traction system of claim 1, wherein the latch assembly is a spring-loaded, off-center draw latch.

20. A traction system for an ambulatory support, the traction system comprising:
a latch assembly operable to latch a sole plate to a distal end of the ambulatory support, the latch assembly including:
a latch base fixable at a top side of the ambulatory support; wherein the latch base includes a plate portion, an anchor portion, and a hinge portion flexibly connecting the plate portion and the anchor portion;
wherein the latch base includes layers of composite material, with fewer of the layers at the hinge portion than at the plate portion and/or at the anchor portion;
wherein one of the layers extends continuously in each of the plate portion, the hinge portion, and the anchor portion; and
wherein the anchor portion is fixable relative to the top side of the ambulatory support and the hinge portion is disposed above and unfixed to the top side of the ambulatory support when the latch base is secured to the ambulatory support.

\* \* \* \* \*